United States Patent
Kaneko et al.

(10) Patent No.: US 8,653,304 B2
(45) Date of Patent: Feb. 18, 2014

(54) 2,3-DIHYDRO-1H-INDENE-2-YL UREA DERIVATIVE AND PHARMACEUTICAL APPLICATION OF SAME

(75) Inventors: Hiroaki Kaneko, Kamakura (JP); Hideki Kawai, Tokyo (JP); Yosuke Iura, Tokyo (JP); Hideki Inoue, Nagoya (JP); Mie Kaino, Kamakura (JP); Hiroyuki Meguro, Kamakura (JP); Tazuru Uchida, Kamakura (JP)

(73) Assignee: Toray Industries, Inc. (JP)

( * ) Notice: Subject to any disclaimer, the term of this patent is extended or adjusted under 35 U.S.C. 154(b) by 145 days.

(21) Appl. No.: 13/497,819

(22) PCT Filed: Sep. 30, 2010

(86) PCT No.: PCT/JP2010/067047
§ 371 (c)(1),
(2), (4) Date: Mar. 23, 2012

(87) PCT Pub. No.: WO2011/040509
PCT Pub. Date: Apr. 7, 2011

(65) Prior Publication Data
US 2012/0184735 A1   Jul. 19, 2012

(30) Foreign Application Priority Data

Sep. 30, 2009  (JP) .................. 2009-227411
Mar. 31, 2010  (JP) .................. 2010-083722

(51) Int. Cl.
*C07C 275/26* (2006.01)
*C07C 275/28* (2006.01)
*A61K 31/17* (2006.01)

(52) U.S. Cl.
USPC ............... 564/52; 564/48; 549/426; 548/577; 546/206; 544/166; 540/611; 514/212.01; 514/237.8; 514/331; 514/429; 514/451; 514/596

(58) Field of Classification Search
USPC ....... 564/48, 52; 549/426; 548/577; 546/206; 544/166; 540/611; 514/212.01, 237.8, 514/331, 429, 451, 596
See application file for complete search history.

(56) References Cited

U.S. PATENT DOCUMENTS

| | | |
|---|---|---|
| 6,451,804 B1 | 9/2002 | Dunn et al. |
| 2005/0065195 A1 | 3/2005 | Angell et al. |

FOREIGN PATENT DOCUMENTS

| | | |
|---|---|---|
| JP | 03-261755 A | 11/1991 |
| JP | 2001-526276 A | 12/2001 |
| JP | 2002-517486 A | 6/2002 |
| JP | 2003-512378 A | 4/2003 |
| JP | 2005-508357 A | 3/2005 |
| JP | 2006-528986 A | 12/2006 |
| JP | 2007-145819 A | 6/2007 |
| WO | 93/14081 A1 | 7/1993 |
| WO | 99/00357 A1 | 1/1999 |
| WO | 99/32463 A1 | 7/1999 |
| WO | 99/64400 A1 | 12/1999 |
| WO | 00/43384 A1 | 7/2000 |
| WO | 02/083642 A1 | 10/2002 |
| WO | 2004/082687 A1 | 9/2004 |
| WO | 2005/000284 A2 | 1/2005 |
| WO | 2007/073503 A2 | 6/2007 |
| WO | 2007/103468 A2 | 9/2007 |

OTHER PUBLICATIONS

Charles A. Dinarello, "Interleukin-1," *Reviews of Infectious Diseases*, vol. 6, No. 1, Jan.-Feb. 1984, pp. 51-95.
Aleksander Koj, "Initiation of acute phase response and synthesis of cytokines," *Biochimica et Biophysica Acta*, vol. 1317, 1996, pp. 84-94.

*Primary Examiner* — Shailendra Kumar
(74) *Attorney, Agent, or Firm* — DLA Piper LLP (US)

(57) ABSTRACT

A 2,3-dihydro-1H-indene-2-yl urea represented by Formula (Ia) or a pharmaceutically acceptable salt thereof:

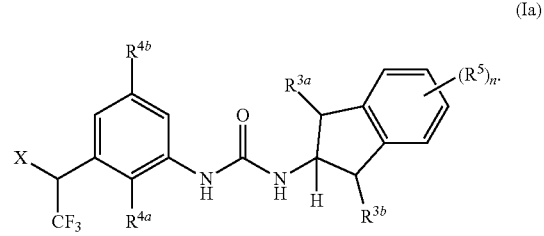

(Ia)

21 Claims, 2 Drawing Sheets

2,3-DIHYDRO-1H-INDENE-2-YL UREA DERIVATIVE AND PHARMACEUTICAL APPLICATION OF SAME

RELATED APPLICATIONS

This is a §371 of International Application No. PCT/JP2010/067047, with an international filing date of Sep. 30, 2010 (WO 2011/040509 A1, published Apr. 7, 2011), which is based on Japanese Patent Application Nos. 2009-227411, filed Sep. 30, 2009, and 2010-083722, filed Mar. 31, 2010, the subject matter of which is incorporated by reference.

TECHNICAL FIELD

This disclosure relates to 2,3-dihydro-1H-indene-2-yl urea derivatives and medical uses thereof.

BACKGROUND

Inflammatory cytokines are biological factors that play important roles in suppressing pathogenic infectious diseases and the like, but inflammatory cytokines can cause inflammatory diseases such as toxic shock syndrome, osteoarthropathy, diabetes or inflammatory bowel disease when they are produced excessively.

Concerning these inflammatory diseases, biologics focusing on the functional antagonism of tumor necrosis factor α (hereinafter referred to as "TNFα"), which is one of inflammatory cytokines, have been actively studied. For example, infliximab, which is a monoclonal antibody against TNFα, has been developed as a therapeutic agent for inflammatory diseases such as uveitis by Behcet's disease or Crohn's disease, since it acts potently in the body as a functional antagonist of TNFα (Koj, Biochim. Biophys. Acta, 1996, Vol. 1317, pp. 84-94 and Dinarello, Rev. Infect. Disease, 1984, Vol. 6, pp. 51-95).

On the other hand, it is known that p38 MAPK, which is a homolog of Mitogen-Activated Protein Kinase (hereinafter referred to as "MAPK"), is activated by stimulation by ultraviolet radiation, lipopolysaccharide (hereinafter referred to as "LPS"), inflammatory cytokines or the like, thereby promoting production of inflammatory cytokines such as TNFα.

WO 99/00357, Japanese Unexamined Patent Application Publication No. 2001-526276, WO 02/083642, WO 07/103,468, Japanese Unexamined Patent Application Publication Nos. 2007-145819, 2006-528986, 2005-508357, 2003-512378 and 2002-517486, WO 00/043384 and WO 93/014081 disclose low molecular weight compounds having a p38 MAPK inhibitory activity, and WO 07/073,503, WO 04/082687 and Japanese Unexamined Patent Application Publication (JP-A) No. 1991-261755 disclose compounds having a 2,3-dihydro-1H-indene-2-yl urea structure. However, there is no disclosure or suggestion as to relationship between a 2,3-dihydro-1H-indene-2-yl urea structure and a p38 MAPK inhibitory activity, and there is no report as to 2,3-dihydro-1H-indene-2-yl urea derivatives having a p38 MAPK inhibitory activity.

Allergic dermatitis is a disease caused due to an allergic reaction and characterized by chronic itching and/or rash on the face, neck, elbow and/or knee. Due to increase of allergens and/or change in dietary habits, etc., the number of patients suffering from allergic dermatitis is increasing year by year and their symptoms tend to be more serious. Treatment of allergic dermatitis is performed mainly by pharmacotherapy and, as therapeutic agents in that case, adrenocortical steroids, immunosuppressive agents, antihistaminic agents and so on are used.

Inflammatory bowel disease is a generic term of diseases mainly causing inflammation and/or ulcer on mucosa of the colon, as typified by ulcerative colitis and Crohn's disease, and this disease is an intractable chronic disease of unknown etiology. A large number of patients are juvenile onset. Diarrhea, blood stool and so on continue for a long period of time, and relapse and remission are repeated. Hence, influence on QOL (Quality of life) of patients is large. Nevertheless, the number of patients is rapidly increasing in recent years. Treatment of inflammatory bowel disease is performed mainly by elemental diet therapy and/or pharmacotherapy. As therapeutic agents in case of pharmacotherapy, 5-aminosalicylic acid preparations, steroids, immunosuppressive agents, antibody preparations and so on are used.

Pain is classified into two types: acute pain which is physiological pain and chronic pain as typified by inflammatory pain and neuropathic pain. In chronic pain, pain lasts for a long time even after disappearance of the substantial tissue damage that caused the initial pain, and the causes thereof are thought to be abnormalities in pain transmission, control or recognition mechanism. Chronic pain is often resistant to opioid analgesics and so on, and is intractable. In addition, pain lasts for a long time, and dysesthesia such as hyperalgesia and/or allodynia occurs. Hence, QOL of patients is markedly reduced. Treatment of chronic pain is performed mainly by pharmacotherapy. As therapeutic agents in that case, Non-Steroidal Anti-Inflammatory Drugs (NSAIDs) are used for inflammatory pain; and anticonvulsants, antidepressants and so on are used for neuropathic pain.

However, in treatment of inflammatory diseases caused by increase in TNFα, biologics such as infliximab may be expected to have a marked therapeutic effect as a functional antagonist, but are necessary to be administered as an injection solution, and therefore the burden on patients is heavy. In addition, such biologics have a risk that their efficacy may be greatly reduced in cases where they are recognized as foreign substances in the body when administered. Accordingly, development of a low molecular weight compound suppressing the TNFα production is desired, but a low molecular weight compound that has no possibility of side effects such as hepatotoxicity has not yet been discovered.

In treatment of allergic dermatitis, dermatitis symptoms are alleviated by using adrenocortical steroids, immunosuppressive agents and/or antihistaminic agents. However, at present, the effect is transient and the use of them is associated with a risk of infectious diseases and/or serious side effects.

In treatment of inflammatory bowel disease, elemental diet therapy has few side effects but greatly affects QOL of patients when the therapy is continued for a long period of time. On the other hand, in case of pharmacotherapy, there are poor response cases and many problems such as infectious diseases and complications.

In treatment of inflammatory pain, nonsteroidal anti-inflammatory agents, as typified by diclofenac sodium, are useful, but they have side effects such as gastrointestinal disorders. On the other hand, in treatment of neuropathic pain, gabapentin, which is an anticonvulsant, is useful, but it also has side effects such as pretty strong drowsiness and staggering.

Thus, it could be helpful to provide a low molecular weight compound which has a p38 MAPK inhibitory activity and a TNFα production suppressing activity associated therewith, and in which a good in vivo pharmacokinetic profile as a pharmaceutical and decrease in hepatotoxicity have been achieved, and a medical use thereof. It could also be helpful to provide a therapeutic or prophylactic agent for allergic dermatitis, inflammatory bowel disease or pain, comprising this low molecular weight compound as an effective ingredient.

SUMMARY

We discovered that a novel 2,3-dihydro-1H-indene-2-yl urea derivative or a pharmaceutically acceptable salt thereof has a marked p38 MAPK inhibitory activity and a TNFα production suppressing activity associated therewith, and has both of an excellent in vivo pharmacokinetic profile and low toxicity, and has an excellent efficacy on allergic dermatitis, inflammatory bowel disease and pain.

We thus provide a 2,3-dihydro-1H-indene-2-yl urea derivative represented by Formula (I) or a pharmaceutically acceptable salt thereof and a pharmaceutical comprising them as an effective ingredient.

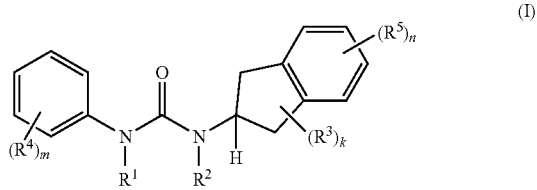

(I)

wherein, k represents an integer of 1 to 4; m represents an integer of 2 to 5; n represents an integer of 0 to 4; $R^1$ and $R^2$ each independently represents hydrogen or alkyl of 1 to 6 carbon atoms; $R^3$ each independently represents alkyl of 1 to 6 carbon atoms (which may be substituted with 1 or more halogen, $R^6O$— and/or $(R^6)_2N$—), $R^6O$—, $(R^6)_2N$— or halogen; $R^4$ and $R^5$ each independently represent alkyl of 1 to 6 carbon atoms (which may be substituted with 1 or more halogen, $R^6O$— and/or $(R^6)_2N$—), cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom), $R^6O$—, $(R^6)_2N$—, $R^6C(O)NH$—, $R^6S(O)_2NH$—, $R^6C(O)$—, $R^6OC(O)$—, $(R^6)_2NC(O)$—, cyano or halogen; and $R^6$ each independently represents hydrogen or alkyl of 1 to 6 carbon atoms (which may be substituted with 1 or more halogen).

Among these, we provide a 2,3-dihydro-1H-indene-2-yl urea derivative represented by Formula (Ia) or a pharmaceutically acceptable salt thereof and a pharmaceutical comprising them as an effective ingredient.

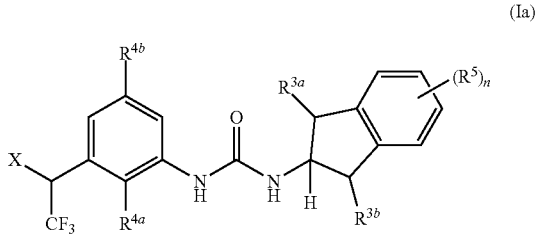

(Ia)

wherein, n represents an integer of 0 to 4; $R^{3a}$ represents $R^6O$— or $(R^6)_2N$—; $R^{3b}$ represents hydrogen, $R^6O$— or $(R^6)_2N$—; $R^{4a}$ represents alkyl of 1 to 6 carbon atoms (which may be substituted with 1 or more halogen, $R^6O$— and/or $(R^6)_2N$—), $R^6O$—, $(R^6)_2N$— or halogen; $R^{4b}$ represents alkyl of 1 to 6 carbon atoms (which may be substituted with 1 or more halogen, $R^6O$— and/or $(R^6)_2N$—)$_5$ cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom), $R^6O$—, $(R^6)_2N$— or halogen; $R^5$ each independently represents alkyl of 1 to 6 carbon atoms (which may be substituted with 1 or more halogen, $R^6O$— and/or $(R^6)_2N$—)$_5$ cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom), $R^6O$—, $(R^6)_2N$—, $R^6C(O)NH$—, $R^6S(O)_2NH$—, $R^6C(O)$—, $R^6OC(O)$—, $(R^6)_2NC(O)$—, cyano or halogen; $R^6$ each independently represents hydrogen or alkyl of 1 to 6 carbon atoms (which may be substituted with 1 or more halogen); and X represents $R^6O$— or $(R^6)_2N$—.

We also provide a therapeutic or prophylactic agent for allergic dermatitis, inflammatory bowel disease or pain, comprising the above-described 2,3-dihydro-1H-indene-2-yl urea derivative or the pharmaceutically acceptable salt thereof as an effective ingredient.

Our 2,3-dihydro-1H-indene-2-yl urea derivative and a pharmaceutically acceptable salt thereof have a p38 MAPK inhibitory activity and a TNFα production suppressing activity associated therewith, and therein a good in vivo pharmacokinetic profile and decrease in hepatotoxicity have been achieved. Therefore, they are useful as a therapeutic drug for inflammatory diseases based on p38 MAPK activation and TNFα production. Our derivatives can be used also as a therapeutic or prophylactic agent for allergic dermatitis, inflammatory bowel disease or pain, having decreased side effects.

DETAILED DESCRIPTION

Figure 1:
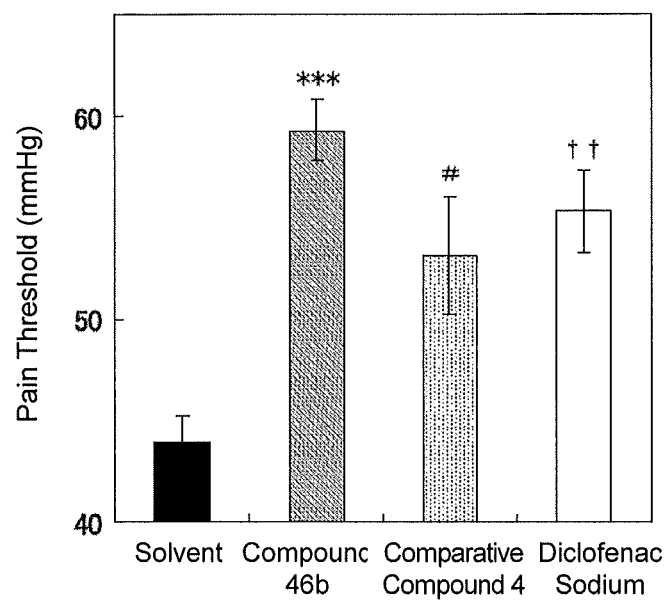
FIG. 1 is a diagram showing the effect of Compound 46b on hyperalgesia in an inflammatory pain model (a carrageenin paw edema pain model).

Unless otherwise specified, the 2,3-dihydro-1H-indene-2-yl urea derivatives (hereinafter referred to as "Compound (I)") and the pharmaceutically acceptable salts thereof include all of isomers due to existence of asymmetric carbons (R-isomers, S-isomers, α-isomers, β-isomers, enantiomers and diastereomers), optical isomers having an optical rotation (D-isomers, L-isomers, d-isomers, l-isomers, (+)-isomers and (−)-isomers), polarity isomers in chromatographic separation (high polarity isomers and low polarity isomers), mixtures thereof at an optional ratio and racemic mixtures.

The following terms used herein are defined as described below unless otherwise specified.

The term "halogen" means fluoro, chloro, bromo, or iodo.

The term "alkyl of 1 to 6 carbon atoms" represents a group of linear or branched saturated hydrocarbon, consisting of 1 to 6 carbon atoms, and, in cases where the phrase "(which may be substituted with 1 or more halogen, $R^6O$— and/or $(R^6)_2N$—)" is added, includes groups wherein a part or all of hydrogen atoms on the alkyl group is substituted with halogen, $R^6O$— and/or $(R^6)_2N$— (wherein $R^6$ represents hydrogen or alkyl of 1 to 6 carbon atoms (which may be substituted with 1 or more halogen).). Therefore, examples of "alkyl of 1 to 6 carbon atoms" or "alkyl of 1 to 6 carbon atoms (which may be substituted with 1 or more halogen, $R^6O$— and/or $(R^6)_2N$—)" include, for example, methyl, ethyl, 1-propyl, 2-propyl, 1-butyl, 2-butyl, 2-methyl-2-propyl, 2-methyl-1-propyl, 1-pentyl, 2-pentyl, 3-pentyl, 2,2-dimethyl-1-propyl, trifluoromethyl, 2,2,2-trifluoroethyl, pentafluoroethyl, trichloromethyl, 2,2,2-trichloroethyl, hydroxymethyl, methoxymethyl, 1-hydroxyethyl, 2-hydroxyethyl, 1-hydroxy-2-methyl-2-propyl, 1,3-dihydroxy-2-methyl-2-propyl, 1-amino-2-methyl-2-propyl, 2,2,2-trifluoro-1-hydroxyethyl, 2,2,2-trifluoro-1-methoxyethyl, 1-amino-2,2,2-trifluoroethyl and 2,2,2-trifluoro-1-(methylamino)ethyl.

The term "cycloalkyl of 3 to 8 carbon atoms" represents a group of monocyclic or polycyclic saturated hydrocarbon, consisting of 3 to 8 carbon atoms, and, in cases where the phrase "(which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom)" is added, includes groups wherein 1 up to 3 hydrogen atoms on the alkyl group are substituted with $R^6$, groups wherein 1 to 3 methylenes constituting a ring are each independently substituted with —O—, —S—, —C(O)— or —N($R^6$)— and groups wherein a carbon atom directly bound to a phenyl group is substituted with a nitrogen atom. Therefore, examples of "cycloalkyl of 3 to 8 carbon atoms" or "cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom)" includes, for example, cyclopropyl, methylcyclopropyl, cyclobutyl, methylcyclobutyl, cyclopentyl, cyclohexyl, cycloheptyl, cyclooctyl, norbornanyl, oxiranyl, oxetanyl, tetrahydrofuranyl, aziridinyl, azetidinyl, pyrrolidinyl, piperidinyl, morpholinyl, azepanyl, tetrahydro-2H-pyran-4-yl and 4-methyltetrahydro-2H-pyran-4-yl.

Our derivatives include all the pharmaceutically acceptable salts of Compound (I). Compounds having substituents that can be salified in Compound (I) can be converted to corresponding salts by known methods.

The acids to be added are preferably non-toxic and water-soluble, and more preferably inorganic acids such as hydrochloric acid, sulfuric acid, nitric acid, hydrobromic acid or phosphoric acid; organic carboxylic acids such as acetic acid, lactic acid, citric acid, maleic acid, benzoic acid, oxalic acid, glutaric acid, malic acid, tartaric acid, fumaric acid, mandelic acid or succinic acid; or organic sulfonic acids such as methanesulfonic acid, p-toluenesulfonic acid or camphorsulfonic acid.

The bases to be added are preferably non-toxic and water-soluble, and more preferably inorganic bases such as sodium hydroxide or potassium hydroxide.

In Formula (I), k is preferably 1 or 2, more preferably 1.
In Formula (I), m is preferably 2 or 3, more preferably 3.
In Formula (I), n is preferably 0 to 2.
In Formula (I), both $R^1$ and $R^2$ are preferably hydrogen.
In Formula (I), $R^3$ is each independently preferably $R^6O$— or $(R^6)_2N$—, more preferably $R^6O$—, still more preferably hydroxy.

In Formula (I), $R^4$ is each independently preferably alkyl of 1 to 6 carbon atoms (which may be substituted with 1 or more halogen, $R^6O$— and/or $(R^6)_2N$—), cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom bound to a benzene ring may be substituted with a nitrogen atom), $R^6O$—, $(R^6)_2N$— or halogen; more preferably methoxy, ethoxy, 2-propyl, 2-butyl, 2-methyl-2-propyl, 2-methyl-2-butyl, pyrrolidino, piperidino, azepanyl, morpholino, bromo, 2,2,2-trifluoro-1-hydroxyethyl, 1-amino-2,2,2-trifluoroethyl, 2,2,2-trifluoro-1-(methylamino)ethyl or 2,2,2-trifluoro-1-(dimethylamino)ethyl; and, still more preferably methoxy, 2-methyl-2-propyl or 2,2,2-trifluoro-1-hydroxyethyl.

In Formula (I), $R^5$ is each independently preferably $R^6O$— or halogen, more preferably hydroxy, methoxy, ethoxy, fluoro, chloro or bromo.

In Formula (Ia), $R^{3a}$ is preferably $R^6O$—, more preferably hydroxy.

$R^{3b}$ is preferably hydrogen.

In Formula (Ia), $R^{4a}$ is preferably $R^6O$—, more preferably methoxy or ethoxy, still more preferably methoxy. $R^{4b}$ is preferably alkyl of 3 to 6 carbon atoms, cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom) or halogen; more preferably 2-propyl, 2-butyl, 2-methyl-2-propyl, 2-methyl-2-butyl, pyrrolidinyl, piperidinyl, azepanyl, morpholinyl or bromo; and still more preferably 2-methyl-2-propyl.

In Formula (Ia), $R^5$ is each independently preferably $R^6O$— or halogen, more preferably hydroxy, methoxy, ethoxy, fluoro, chloro or bromo.

In Formula (Ia), X is preferably hydroxy, amino, methylamino or dimethylamino, more preferably hydroxy.

Examples of Compound (I) include, for example, compounds represented by Formula (Ib) which are listed in Table 1. In the Tables, the wavy lines in the structural formulae mean that those are substituted at the position of the line.

TABLE 1

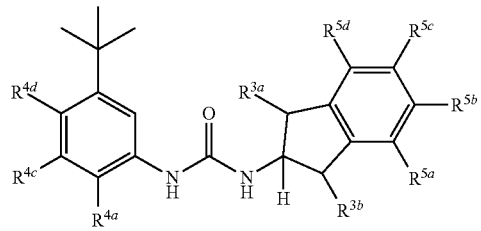

(Ib)

| Compound | $R^{3a}$ | $R^{3b}$ | $R^{4a}$ | $R^{4c}$ | $R^{4d}$ | $R^{5a}$ | $R^{5b}$ | $R^{5c}$ | $R^{5d}$ |
|---|---|---|---|---|---|---|---|---|---|
| 1 | OH | H | CH$_3$O | HOCH$_2$ | H | H | H | H | H |
| 2 | OH | H | CH$_3$O | HOCH$_2$ | H | CH$_3$ | H | H | H |
| 3 | OH | H | CH$_3$O | HOCH$_2$ | H | F | H | H | H |
| 4 | OH | H | CH$_3$O | HOCH$_2$ | H | Cl | H | H | H |
| 5 | OH | H | CH$_3$O | HOCH$_2$ | H | CH$_3$O | H | H | H |
| 6 | OH | H | CH$_3$O | HOCH$_2$ | H | OH | H | H | H |
| 7 | OH | H | CH$_3$O | HOCH$_2$ | H | H | CH$_3$ | H | H |

TABLE 1-continued (Ib)

| Compound | $R^{3a}$ | $R^{3b}$ | $R^{4a}$ | $R^{4c}$ | $R^{4d}$ | $R^{5a}$ | $R^{5b}$ | $R^{5c}$ | $R^{5d}$ |
|---|---|---|---|---|---|---|---|---|---|
| 8 | OH | H | CH$_3$O | HOCH$_2$ | H | H | F | H | H |
| 9 | OH | H | CH$_3$O | HOCH$_2$ | H | H | CH$_3$O | H | H |
| 10 | OH | H | CH$_3$O | HOCH$_2$ | H | H | H | CH$_3$ | H |
| 11 | OH | H | CH$_3$O | HOCH$_2$ | H | H | H | F | H |
| 12 | OH | H | CH$_3$O | HOCH$_2$ | H | H | H | CH$_3$O | H |
| 13 | OH | H | CH$_3$O | HOCH$_2$ | H | H | H | H | CH$_3$ |
| 14 | OH | H | CH$_3$O | HOCH$_2$ | H | H | H | H | F |
| 15 | OH | H | CH$_3$O | HOCH$_2$ | H | H | H | H | CH$_3$O |
| 16 | OH | H | CH$_3$O | morpholin-4-yl | H | H | H | H | H |
| 17 | OH | H | CH$_3$O | H$_2$N | H | H | H | H | H |
| 18 | OH | H | CH$_3$O | CH$_3$NH | H | H | H | H | H |
| 19 | OH | H | CH$_3$O | (CH$_3$)$_2$N | H | H | H | H | H |
| 20 | OH | H | CH$_3$O | HO(CH$_3$)CH | H | H | H | H | H |
| 21 | OH | H | CH$_3$O | H$_3$CC(O) | H | H | H | H | H |
| 22 | OH | H | CH$_3$O | HO(CH$_3$)$_2$C | H | H | H | H | H |
| 23 | OH | H | CH$_3$O | CH$_3$S(O)$_2$NH | H | H | H | H | H |
| 24 | OH | H | CH$_3$O | (CH$_3$)$_2$NCH$_2$ | H | H | H | H | H |
| 25 | OH | H | CH$_3$O | CH$_3$NHCH$_2$ | H | H | H | H | H |
| 26 | OH | H | CH$_3$O | 2-(morpholin-4-yl)ethyl | H | H | H | H | H |
| 27 | OH | H | CH$_3$O | HO(CH$_2$CH$_3$)CH | H | H | H | H | H |
| 28 | OH | H | CH$_3$O | F | H | H | H | H | H |
| 29 | OH | H | CH$_3$O | CH$_3$C(O)NH | H | H | H | H | H |
| 30 | OH | H | HOCH$_2$ | H | H | H | H | H | H |
| 31 | OH | H | C$_2$H$_5$O | HOCH$_2$ | H | H | H | H | H |
| 32 | OH | H | (CH$_3$)$_2$CHO | HOCH$_2$ | H | H | H | H | H |
| 33 | OH | H | CH$_3$O | CH$_3$OCH$_2$ | H | H | H | H | H |
| 34 | OH | H | CH$_3$O | HOCH(CH(CH$_3$)$_2$) | H | H | H | H | H |
| 35 | OH | H | CH$_3$O | C$_2$H$_5$OCH$_2$ | H | H | H | H | H |
| 36 | OH | H | CH$_3$O | H | HOCH$_2$ | H | H | H | H |
| 37 | OH | H | CH$_3$O | HO(C$_2$H$_5$)CH | H | H | H | H | H |
| 38 | OH | H | CH$_3$O | CH$_3$NHCH(CH$_3$) | H | H | H | H | H |
| 39 | OH | H | CH$_3$O | F$_2$CH | H | H | H | H | H |
| 40 | OH | H | CH$_3$O | H$_2$NC(O) | H | H | H | H | H |
| 41 | OH | H | CH$_3$O | H$_2$NC(CH$_3$)$_2$ | H | H | H | H | H |
| 42 | OH | H | CH$_3$O | CH$_3$NHC(O) | H | H | H | H | H |
| 43 | OH | H | CH$_3$O | (CH$_3$)$_2$NC(O) | H | H | H | H | H |
| 44 | OH | H | CH$_3$O | CF$_3$C(O) | H | H | H | H | H |
| 45 | OH | H | H | HO(CF$_3$)CH | H | H | H | H | H |
| 46 | OH | H | CH$_3$O | HO(CF$_3$)CH | H | H | H | H | H |
| 47 | OH | H | CH$_3$O | H$_2$N(CF$_3$)CH | H | H | H | H | H |
| 48 | OH | H | CH$_3$O | CH$_3$NH(CF$_3$)CH | H | H | H | H | H |
| 49 | OH | H | CH$_3$O | HO(CF$_3$)CH | H | CH$_3$ | H | H | H |
| 50 | OH | H | CH$_3$O | HO(CF$_3$)CH | H | F | H | H | H |
| 51 | OH | H | CH$_3$O | HO(CF$_3$)CH | H | Cl | H | H | H |
| 52 | OH | H | CH$_3$O | HO(CF$_3$)CH | H | CH$_3$O | H | H | H |
| 53 | OH | H | CH$_3$O | HO(CF$_3$)CH | H | OH | H | H | H |
| 54 | OH | H | CH$_3$O | HO(CF$_3$)CH | H | H | CH$_3$ | H | H |
| 55 | OH | H | CH$_3$O | HO(CF$_3$)CH | H | H | F | H | H |
| 56 | OH | H | CH$_3$O | HO(CF$_3$)CH | H | H | Cl | H | H |
| 57 | OH | H | CH$_3$O | HO(CF$_3$)CH | H | H | CH$_3$O | H | H |
| 58 | OH | H | CH$_3$O | HO(CF$_3$)CH | H | H | OH | H | H |

TABLE 1-continued (Ib)

[Structure of Formula (Ib): a urea linking a 4-tert-butyl-substituted phenyl ring (bearing R4a, R4c, R4d) to an indane (bearing R3a, R3b, R5a, R5b, R5c, R5d).]

| Compound | R3a | R3b | R4a | R4c | R4d | R5a | R5b | R5c | R5d |
|---|---|---|---|---|---|---|---|---|---|
| 59 | OH | H | CH3O | HO(CF3)CH | H | H | H | CH3 | H |
| 60 | OH | H | CH3O | HO(CF3)CH | H | H | H | F | H |
| 61 | OH | H | CH3O | HO(CF3)CH | H | H | H | Cl | H |
| 62 | OH | H | CH3O | HO(CF3)CH | H | H | H | CH3O | H |
| 63 | OH | H | CH3O | HO(CF3)CH | H | H | H | OH | H |
| 64 | OH | H | CH3O | HO(CF3)CH | H | H | H | H | CH3 |
| 65 | OH | H | CH3O | HO(CF3)CH | H | H | H | H | F |
| 66 | OH | H | CH3O | HO(CF3)CH | H | H | H | H | Cl |
| 67 | OH | H | CH3O | HO(CF3)CH | H | H | H | H | CH3O |
| 68 | OH | H | CH3O | HO(CF3)CH | H | H | H | H | OH |
| 69 | OH | H | CH3O | HO(CF3)CH | H | H | H | H | NH2 |
| 70 | OH | H | CH3O | HO(CF3)CH | H | H | H | H | CH3NH |
| 71 | OH | H | CH3O | HO(CF3)CH | H | H | H | H | CN |
| 72 | OH | H | CH3O | HO(CF3)CH | H | H | H | H | CH3S(O)2NH |
| 73 | OH | H | CH3O | HO(CF3)CH | H | F | H | H | F |
| 74 | OH | H | OH | HO(CF3)CH | H | H | H | H | H |
| 75 | OH | H | OH | HO(CF3)CH | H | F | H | H | H |
| 76 | OH | H | OH | HO(CF3)CH | H | H | F | H | H |
| 77 | OH | H | OH | HO(CF3)CH | H | H | H | F | H |
| 78 | OH | H | OH | HO(CF3)CH | H | H | H | H | F |
| 79 | CH3O | H | CH3O | HO(CF3)CH | H | H | H | H | H |
| 80 | OH | OH | CH3O | HO(CF3)CH | H | H | H | H | H |
| 81 | F | H | CH3O | HO(CF3)CH | H | H | H | H | H |

In addition, examples of Compound (I) include, for example, compounds represented by Formula (Ic) which are listed in Table 2. In the Tables, the wavy lines in the structural formulae mean that those are substituted at the position of the line.

TABLE 2

(Ic)

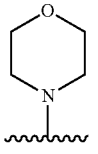 [SMILES: *N1CCOCC1]

| Compound | X | R3a | R3b | R4a | R4b | R5a | R5b | R5c | R5d |
|---|---|---|---|---|---|---|---|---|---|
| 82 | OH | OH | H | CH3O | Br | H | H | H | H |
| 83 | OH | OH | H | CH3O | ![morpholine] | H | H | H | H |
| 84 | OH | OH | H | CH3O | ![morpholine] | F | H | H | H |
| 85 | OH | OH | H | CH3O | ![morpholine] | CH3O | H | H | H |

TABLE 2-continued

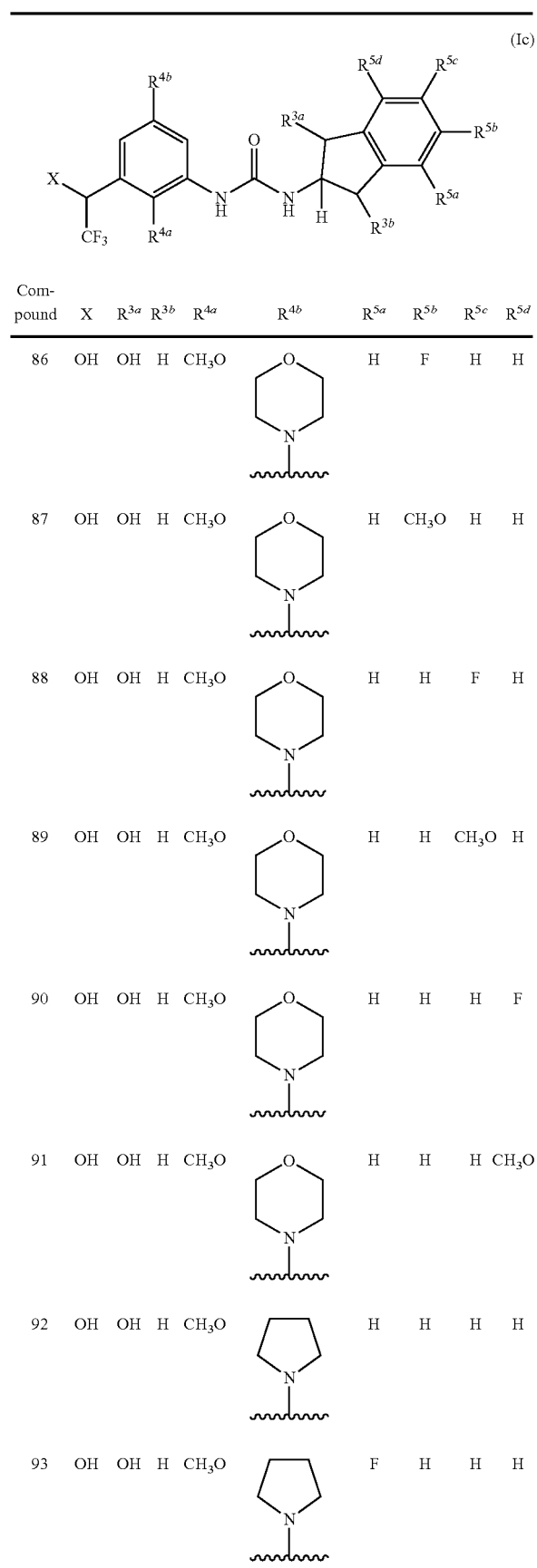

| Compound | X | $R^{3a}$ | $R^{3b}$ | $R^{4a}$ | $R^{4b}$ | $R^{5a}$ | $R^{5b}$ | $R^{5c}$ | $R^{5d}$ |
|---|---|---|---|---|---|---|---|---|---|
| 86 | OH | OH | H | $CH_3O$ | morpholino | H | F | H | H |
| 87 | OH | OH | H | $CH_3O$ | morpholino | H | $CH_3O$ | H | H |
| 88 | OH | OH | H | $CH_3O$ | morpholino | H | H | F | H |
| 89 | OH | OH | H | $CH_3O$ | morpholino | H | H | $CH_3O$ | H |
| 90 | OH | OH | H | $CH_3O$ | morpholino | H | H | H | F |
| 91 | OH | OH | H | $CH_3O$ | morpholino | H | H | H | $CH_3O$ |
| 92 | OH | OH | H | $CH_3O$ | pyrrolidinyl | H | H | H | H |
| 93 | OH | OH | H | $CH_3O$ | pyrrolidinyl | F | H | H | H |

TABLE 2-continued

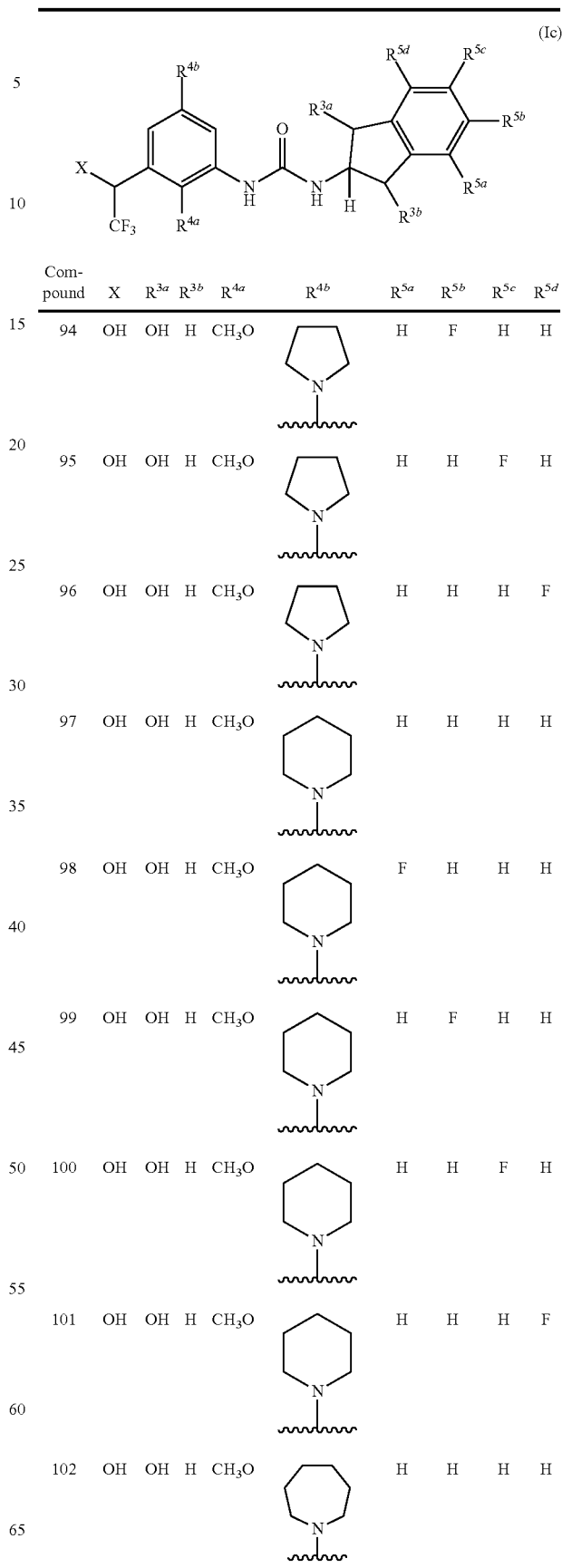

| Compound | X | $R^{3a}$ | $R^{3b}$ | $R^{4a}$ | $R^{4b}$ | $R^{5a}$ | $R^{5b}$ | $R^{5c}$ | $R^{5d}$ |
|---|---|---|---|---|---|---|---|---|---|
| 94 | OH | OH | H | $CH_3O$ | pyrrolidinyl | H | F | H | H |
| 95 | OH | OH | H | $CH_3O$ | pyrrolidinyl | H | H | F | H |
| 96 | OH | OH | H | $CH_3O$ | pyrrolidinyl | H | H | H | F |
| 97 | OH | OH | H | $CH_3O$ | piperidinyl | H | H | H | H |
| 98 | OH | OH | H | $CH_3O$ | piperidinyl | F | H | H | H |
| 99 | OH | OH | H | $CH_3O$ | piperidinyl | H | F | H | H |
| 100 | OH | OH | H | $CH_3O$ | piperidinyl | H | H | F | H |
| 101 | OH | OH | H | $CH_3O$ | piperidinyl | H | H | H | F |
| 102 | OH | OH | H | $CH_3O$ | azepanyl | H | H | H | H |

TABLE 2-continued

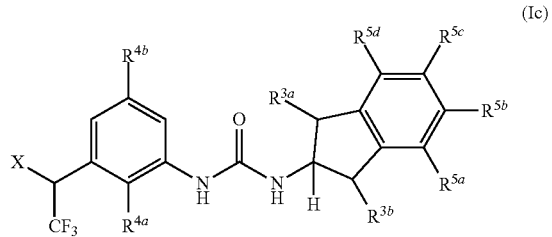 (Ic)

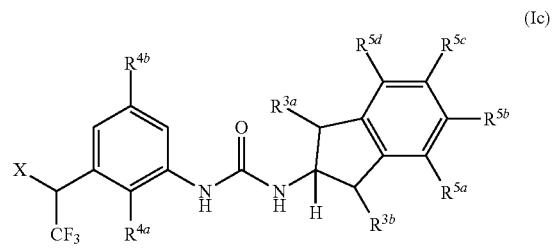 (Ic)

| Compound | X | R3a | R3b | R4a | R4b | R5a | R5b | R5c | R5d |
|---|---|---|---|---|---|---|---|---|---|
| 103 | OH | OH | H | CH3O | azepan-1-yl | F | H | H | H |
| 104 | OH | OH | H | CH3O | azepan-1-yl | H | F | H | H |
| 105 | OH | OH | H | CH3O | azepan-1-yl | H | H | F | H |
| 106 | OH | OH | H | CH3O | azepan-1-yl | H | H | H | F |
| 107 | OH | OH | H | CH3O | tetrahydropyran-4-yl | H | H | H | H |
| 108 | OH | OH | H | CH3O | 4-methyltetrahydropyran-4-yl | H | H | H | H |
| 109 | OH | OH | H | CH3O | 4-methyltetrahydropyran-4-yl | F | H | H | H |
| 110 | OH | OH | H | CH3O | 4-methyltetrahydropyran-4-yl | H | F | H | H |
| 111 | OH | OH | H | CH3O | 4-methyltetrahydropyran-4-yl | H | H | F | H |
| 112 | OH | OH | H | CH3O | 4-methyltetrahydropyran-4-yl | H | H | H | F |
| 113 | NH2 | OH | H | CH3O | morpholin-4-yl | H | H | H | H |
| 114 | NH2 | OH | H | CH3O | morpholin-4-yl | F | H | H | H |
| 115 | NH2 | OH | H | CH3O | morpholin-4-yl | H | F | H | H |
| 116 | NH2 | OH | H | CH3O | morpholin-4-yl | H | H | F | H |
| 117 | NH2 | OH | H | CH3O | morpholin-4-yl | H | H | H | F |
| 118 | NH2 | OH | H | CH3O | pyrrolidin-1-yl | H | H | H | H |
| 119 | NH2 | OH | H | CH3O | piperidin-1-yl | H | H | H | H |

TABLE 2-continued

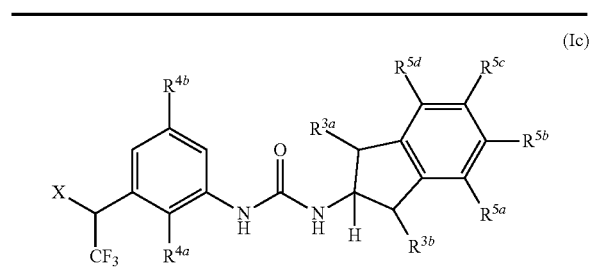

(Ic)

| Compound | X | R3a | R3b | R4a | R4b | R5a | R5b | R5c | R5d |
|---|---|---|---|---|---|---|---|---|---|
| 120 | NH2 | OH | H | CH3O | azepan-1-yl | H | H | H | H |
| 121 | NH2 | OH | H | CH3O | tetrahydropyran-4-yl | H | H | H | H |
| 122 | NH2 | OH | H | CH3O | 4-methyltetrahydropyran-4-yl | H | H | H | H |
| 123 | OH | OH | H | CH3O | 2-methylbutan-2-yl | H | H | H | H |
| 124 | OH | OH | H | CH3O | 2-methylbutan-2-yl | F | H | H | H |
| 125 | OH | OH | H | CH3O | 2-methylbutan-2-yl | H | F | H | H |
| 126 | OH | OH | H | CH3O | 2-methylbutan-2-yl | H | H | F | H |
| 127 | OH | OH | H | CH3O | 2-methylbutan-2-yl | H | H | H | F |
| 128 | OH | OH | H | CH3O | cyclopropyl | H | H | H | H |
| 129 | OH | OH | H | CH3O | 1-methylcyclopropyl | H | H | H | H |
| 130 | OH | OH | H | CH3O | 1-methylcyclopropyl | F | H | H | H |

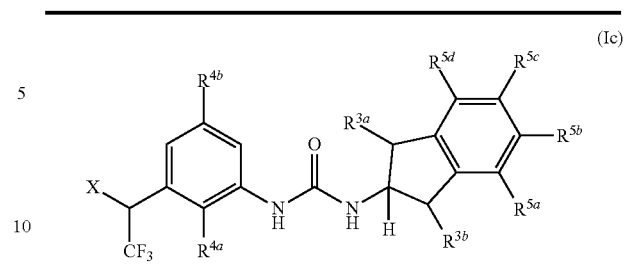

(Ic)

| Compound | X | R3a | R3b | R4a | R4b | R5a | R5b | R5c | R5d |
|---|---|---|---|---|---|---|---|---|---|
| 131 | OH | OH | H | CH3O | 1-methylcyclopropyl | H | F | H | H |
| 132 | OH | OH | H | CH3O | 1-methylcyclopropyl | H | H | F | H |
| 133 | OH | OH | H | CH3O | 1-methylcyclopropyl | H | H | H | F |
| 134 | OH | OH | H | CH3O | cyclobutyl | H | H | H | H |
| 135 | OH | OH | H | CH3O | 1-methylcyclobutyl | H | H | H | H |
| 136 | OH | OH | H | CH3O | 1-methylcyclobutyl | F | H | H | H |
| 137 | OH | OH | H | CH3O | 1-methylcyclobutyl | H | F | H | H |
| 138 | OH | OH | H | CH3O | 1-methylcyclobutyl | H | H | F | H |
| 139 | OH | OH | H | CH3O | 1-methylcyclobutyl | H | H | H | F |
| 140 | OH | OH | H | CH3O | cyclopentyl | H | H | H | H |
| 141 | OH | OH | H | CH3O | 1-methylcyclopentyl | H | H | H | H |

TABLE 2-continued

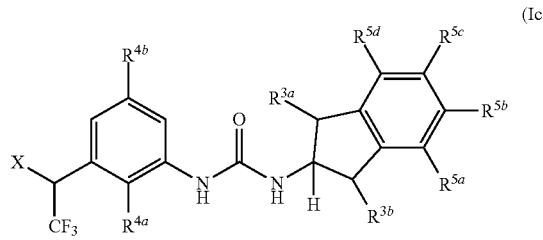

(Ic)

| Compound | X | R³ᵃ | R³ᵇ | R⁴ᵃ | R⁴ᵇ | R⁵ᵃ | R⁵ᵇ | R⁵ᶜ | R⁵ᵈ |
|---|---|---|---|---|---|---|---|---|---|
| 142 | OH | OH | H | CH₃O | cyclohexylmethyl | H | H | H | H |
| 143 | OH | OH | H | CH₃O | 1-methylcyclohexyl | H | H | H | H |
| 144 | OH | OH | H | CH₃O | -C(CH₃)₂CH₂OH | H | H | H | H |
| 145 | OH | OH | H | CH₃O | -C(CH₃)₂CH₂OH | F | H | H | H |
| 146 | OH | OH | H | CH₃O | -C(CH₃)₂CH₂OH | H | F | H | H |
| 147 | OH | OH | H | CH₃O | -C(CH₃)₂CH₂OH | H | H | F | H |
| 148 | OH | OH | H | CH₃O | -C(CH₃)₂CH₂OH | H | H | H | F |
| 149 | NH₂ | OH | H | CH₃O | -CH(CH₃)CH₂CH₃ | H | H | H | H |
| 150 | NH₂ | OH | H | CH₃O | cyclopropyl | H | H | H | H |
| 151 | NH₂ | OH | H | CH₃O | 1-methylcyclopropyl | H | H | H | H |
| 152 | NH₂ | OH | H | CH₃O | cyclobutyl | H | H | H | H |
| 153 | NH₂ | OH | H | CH₃O | 1-methylcyclobutyl | H | H | H | H |
| 154 | NH₂ | OH | H | CH₃O | cyclopentylmethyl | H | H | H | H |
| 155 | NH₂ | OH | H | CH₃O | 1-methylcyclopentyl | H | H | H | H |
| 156 | NH₂ | OH | H | CH₃O | cyclohexylmethyl | H | H | H | H |
| 157 | NH₂ | OH | H | CH₃O | 1-methylcyclohexyl | H | H | H | H |
| 158 | NH₂ | OH | H | CH₃O | -C(CH₃)₂CH₂OH | H | H | H | H |

For example, Compound (I) can be synthesized according to Scheme 1. The meanings of the symbols in each reaction formula are as defined above unless otherwise specified.

In the production method described below, in cases where the raw material compound has a hydroxyl group(s), it may be protected by a commonly used protective group(s); and the protective group(s) can be removed as required after the reaction to obtain the desired compound. Examples of the protective group for the hydroxyl group include, for example, an alkyl group, a phenyl group, a triphenylmethyl group, an aralkyl group, an acyl group and a substituted silyl group.

The method for removing the above-described protective group is appropriately selected depending on the type of the protective group, and known methods such as the method described in PROTECTIVE GROUPS IN ORGANIC SYNTHESIS (WILEY-INTERSCIENCE) may be used.

In the production method described below, the raw material compound may be used as a salt. Examples of the acid or base to be added include the same acids or bases as described above as to the salification of Compound (I).

Compound (I) obtained by the production method described below may be isolated and purified by known means. Examples of the method for the isolation and purification include, for example, solvent extraction, recrystallization and chromatography.

In cases where Compound (I) has optical isomers and/or stereoisomers, each isomer can be obtained as a single compound by a known method.

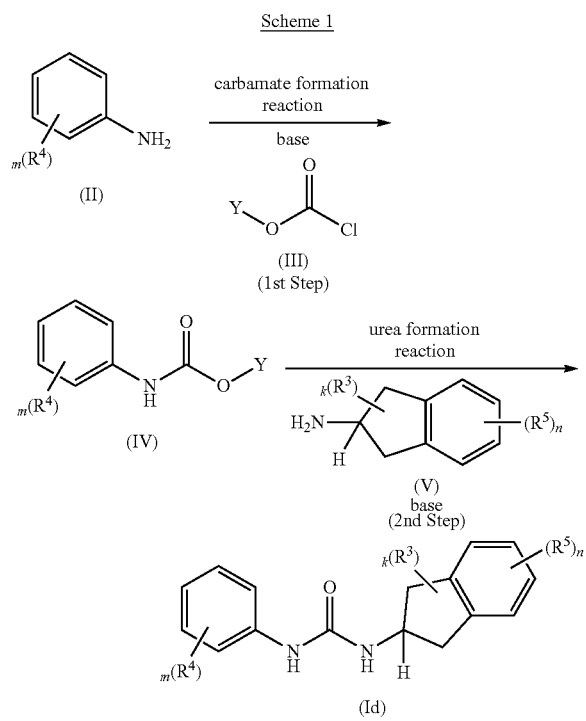

In Scheme 1, Y represents alkyl group of 1 to 6 carbon atoms (which may be substituted with 1 or more halogen) or an aryl group of 6 to 10 carbon atoms (which may be appropriately substituted).

1st Step

The carbamate compound represented by Formula (IV) can be synthesized by reacting the aniline derivative represented by Formula (II) and the chloroformate represented by Formula (III) in the presence of a base in an appropriate solvent.

Examples of the above-mentioned chloroformate include those that have a leaving group with which the reaction of urea formation in the Second Step can be proceeded smoothly, for example, methyl chloroformate, ethyl chloroformate, 2,2,2-trichloroethyl chloroformate, phenyl chloroformate, 4-chlorophenyl chloroformate, 4-nitrophenyl chloroformate and 1-naphthyl chloroformate, but 2,2,2-trichloroethyl chloroformate or phenyl chloroformate is preferable.

The amount of the above-mentioned chloroformate to be used is preferably 0.5 to 5 mol, more preferably 0.8 to 3 mol, with respect to 1 mol of the aniline derivative represented by Formula (II).

Examples of the base to be made to coexist include, for example, alkali metal hydrogen carbonates such as sodium hydrogen carbonate and potassium hydrogen carbonate; alkali metal carbonates such as potassium carbonate and cesium carbonate; amines such as triethylamine, N,N-diisopropylethylamine and pyridine; alkali metal alkoxides such as potassium tert-butoxide; and hydrides of alkali metals such as sodium hydride, but sodium hydrogen carbonate, triethylamine or N,N-diisopropylethylamine is preferable.

The amount of the base to be used to be made to coexist is preferably 0.5 to 6 mol, more preferably 0.8 to 3 mol, with respect to 1 mol of the aniline derivative represented by Formula (II).

Usually, the reaction solvent is appropriately selected from solvents that do not inhibit the reaction. Examples of the reaction solvent include, for example, ether solvents such as tetrahydrofuran (hereinafter referred to as THF), 1,4-dioxane and ethylene glycol dimethyl ether; halogenated solvents such as dichloromethane, chloroform and 1,2-dichloroethane; aromatic hydrocarbon solvents such as benzene and toluene; aprotic polar solvents such as N,N-dimethylformamide (hereinafter referred to as DMF) and dimethyl sulfoxide (hereinafter referred to as DMSO); ketone solvents such as acetone and methyl ethyl ketone; nitrile solvents such as acetonitrile and propionitrile; and water, and mixed solvents thereof, but an ether solvent is preferable.

The concentration of the aniline derivative represented by Formula (II) in the reaction solution is preferably 0.01 to 5 mol/L, more preferably 0.1 to 2 mol/L.

The reaction temperature is preferably −78 to 200° C., more preferably −20 to 100° C.

The reaction time is appropriately selected depending on the conditions such as reaction temperature, and satisfactory results are usually obtained when the selected reaction time is about 10 to 30 hours.

2nd Step

The urea compound represented by Formula (Id) can be synthesized by reacting the carbamate compound represented by Formula (IV) and the 2-amino-2,3-dihydro-1H-indene compound represented by Formula (V) in the presence of a base in an appropriate solvent.

Examples of the base to be made to coexist include, for example, alkaline metal hydroxides such as sodium hydroxide and potassium hydroxide; trialkylamines such as triethylamine and N,N-diisopropylethylamine; cyclic amidines such as diazabicyclo[5.4.0]undecene; and aromatic amines such as pyridine and N,N-dimethylaminopyridine, but trialkylamines are preferable.

The amount of the base to be used to be made to coexist is preferably 0.5 to 10 mol, more preferably 0.8 to 5 mol, with respect to 1 mol of the carbamate compound represented by Formula (IV).

Usually, the reaction solvent is appropriately selected from solvents that do not inhibit the reaction. Examples of the reaction solvent include, for example, ether solvents such as THF, 1,4-dioxane and ethylene glycol dimethyl ether; halogenated solvents such as dichloromethane, chloroform and 1,2-dichloroethane; aromatic hydrocarbon solvents such as benzene and toluene; aprotic polar solvents such as DMF and DMSO; ketone solvents such as acetone and methyl ethyl ketone; nitrile solvents such as acetonitrile and propionitrile; and water, and mixed solvents thereof, but an ether solvent, a nitrile solvent or a mixed solvent of an ether solvent or a nitrile solvent with water is preferable.

The concentration of the carbamate compound represented by Formula (IV) in the reaction solution is preferably 0.01 to 5 mol/L, more preferably 0.1 to 2 mol/L.

The reaction temperature is preferably −20 to 200° C., more preferably 0 to 150° C.

The reaction time is appropriately selected depending on the conditions such as reaction temperature, and satisfactory results are usually obtained when the selected reaction time is about 30 minutes to about 48 hours.

Among the aniline derivatives that are a raw material in Scheme 1, aniline derivatives having a 2,2,2-trifluoro-1-hydroxyethyl group as represented by Formula (IX) can be produced by the method shown in Scheme 2.

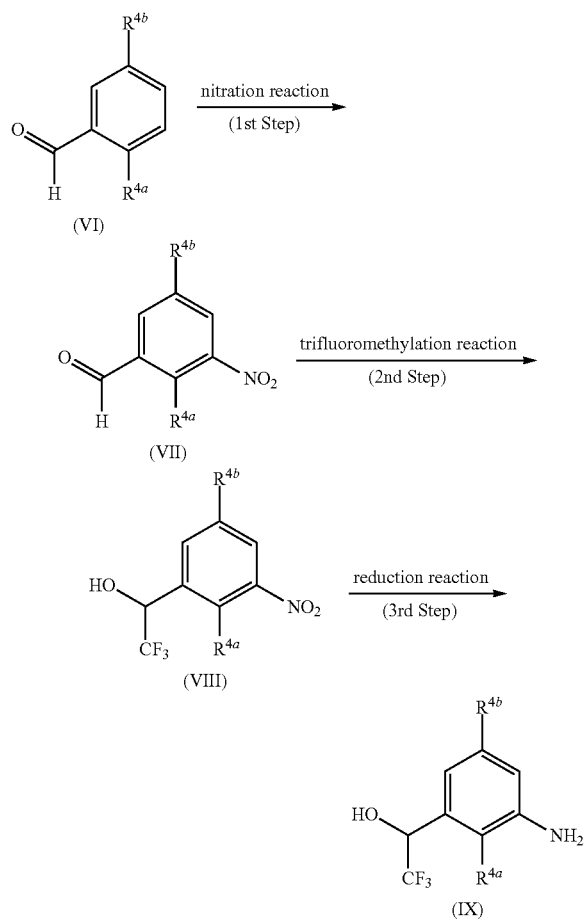

Scheme 2

1st Step

The nitro compound represented by Formula (VII) can be synthesized by reacting a nitrating agent to the benzaldehyde derivative represented by Formula (VI) in an appropriate solvent.

Examples of the benzaldehyde derivative represented by Formula (VI) include commercially available compounds or derivatives from commercially available compounds. Examples of the method for deriving a commercially available product include, for example, the methods described in *Bioorganic & Medicinal Chemistry* (2008, Vol. 16, No. 15, pp. 7193-7205) and *Synthesis* (1998, Vol. 7, pp. 1029-1032).

Examples of the above-mentioned nitrating agent include, for example, nitronium cation generated from a combination such as nitric acid and sulfuric acid or nitric acid and acetic anhydride in a reaction system; and a nitronium salt such as nitronium tetrafluoroborate, but a nitronium salt is preferable.

The amount of the above-mentioned nitrating agent to be used is preferably 0.5 to 5 mol, more preferably 0.8 to 3 mol, with respect to 1 mol of the benzaldehyde derivative represented by Formula (VI).

As the reaction solvent, a solvent that does not inhibit the reaction is appropriately selected. Examples thereof include, for example, ester solvents such as ethyl acetate and n-propyl acetate; nitrile solvents such as acetonitrile and propionitrile; ether solvents such as THF, 1,4-dioxane and ethylene glycol dimethyl ether; and halogenated solvents such as dichloromethane, chloroform and 1,2-dichloroethane, and mixed solvents thereof, but an ester solvent or a nitrile solvent is preferable.

The concentration of the benzaldehyde derivative represented by Formula (VI) in the reaction solution is preferably 0.01 to 5 mol/L, more preferably 0.05 to 2 mol/L.

The reaction temperature is preferably −78 to 50° C., more preferably −40 to 30° C.

The reaction time is appropriately selected depending on the conditions such as reaction temperature, and satisfactory results are usually obtained when the selected reaction time is about 30 minutes to about 6 hours.

2nd Step

The trifluoroethanol derivative represented by Formula (VIII) can be synthesized by reacting the benzaldehyde derivative represented by Formula (VII) and a agent for trifluoromethylation in an appropriate solvent, and as required, in the presence of a fluoride salt.

Examples of the fluoride salt to be made to coexist include, for example, alkali metal salts such as sodium fluoride and potassium fluoride; and ammonium salts such as tetramethylammonium fluoride and tetra n-butylammonium fluoride, but an ammonium salt is preferable.

The amount of the fluoride salt to be used to be made to coexist is preferably 0.01 to 2 mol, more preferably 0.05 to 1 mol, with respect to 1 mol of the benzaldehyde derivative represented by Formula (VII).

Examples of the above-mentioned agent for trifluoromethylation include, for example, trifluoromethyl iodide and trimethyl(trifluoromethyl)silane, but trimethyl(trifluoromethyl)silane is preferable.

The amount of the above-mentioned agent for trifluoromethylation to be used is preferably 0.5 to 10 mol, more preferably 0.8 to 5 mol, with respect to 1 mol of the benzaldehyde derivative represented by Formula (VII).

Usually, as the reaction solvent, a solvent that does not inhibit the reaction is appropriately selected. Examples thereof include, for example, ether solvents such as THF, 1,4-dioxane and ethylene glycol dimethyl ether; and aromatic hydrocarbon solvents such as benzene and toluene, and mixed solvents thereof, but an ether solvent is preferable.

The concentration of the benzaldehyde derivative represented by Formula (VII) in the reaction solution is preferably 0.001 to 5 mol/L, more preferably 0.05 to 1 mol/L.

The reaction temperature is preferably −78 to 50° C., more preferably −30 to 30° C.

The reaction time is appropriately selected depending on the conditions such as reaction temperature, and satisfactory results are usually obtained when the selected reaction time is about 30 minutes to about 12 hours.

3rd Step

The aniline derivative represented by Formula (IX) can be synthesized by reducing the nitro group of the nitro compound represented by Formula (VIII) in an appropriate solvent. Examples of the method for the reduction include, for example, catalytic hydrogenation and one-electron reduction.

Catalytic Hydrogenation

Examples of a metal catalyst to be used include, for example, palladium/activated charcoal, palladium hydroxide/activated charcoal and platinum oxide, but palladium/activated charcoal is preferable.

The amount of the above-mentioned metal catalyst to be used is preferably 0.5 to 200% by weight, more preferably 5 to 100% by weight, with respect to the weight of 1 mol of the nitro compound represented by Formula (VIII).

The pressure of hydrogen gas is preferably 1 to 10 atm, more preferably 1 to 3 atm.

Usually, as the reaction solvent, a solvent that does not inhibit the reaction is appropriately selected. Examples thereof include, for example, alcohol solvents such as methanol, ethanol and 2-propanol; ester solvents such as ethyl acetate and n-propyl acetate; ether solvents such as THF, 1,4-dioxane and ethylene glycol dimethyl ether; halogenated solvents such as dichloromethane, chloroform and 1,2-dichloroethane; and water, and mixed solvents thereof, but an alcohol solvent or an ester solvent is preferable.

The concentration of the nitro compound represented by Formula (VIII) in the reaction solution is preferably 0.001 to 5 mol/L, more preferably 0.05 to 2 mol/L.

The reaction temperature is preferably 0 to 100° C., more preferably 10 to 60° C.

The reaction time is appropriately selected depending on the conditions such as reaction temperature, and satisfactory results are usually obtained when the selected reaction time is about 30 minutes to about 48 hours.

One-Electron Reduction

Examples of a reducing agent to be used include, for example, metals of simple substance such as iron, nickel and tin; and metal chlorides such as iron chloride and tin chloride, but iron is preferable.

The amount of the above-mentioned reducing agent to be used is preferably 1 to 20 mol, more preferably 1 to 10 mol, with respect to 1 mol of the nitro compound represented by Formula (VIII).

In the reaction solution, an activating agent is preferably made to coexist. Examples of the activating agent include, for example, inorganic acids such as hydrochloric acid and sulfuric acid; and ammonium salts such as ammonium chloride, but an ammonium salt is preferable.

The amount of the above-mentioned activating agent is preferably 1 to 20 mol, more preferably 1 to 10 mol, with respect to 1 mol of the nitro compound represented by Formula (VIII).

Usually, as the reaction solvent, a solvent that does not inhibit the reaction is appropriately selected. Examples thereof include, for example, alcohol solvents such as methanol, ethanol and 2-propanol; ether solvents such as THF, 1,4-dioxane and ethylene glycol dimethyl ether; and water, and mixed solvents thereof, but a mixed solvent of an alcohol solvent and water, a mixed solvent of an ether solvent and water or a mixed solvent of an alcohol solvent, an ether solvent and water is preferable.

The concentration of the nitro compound represented by Formula (VIII) in the reaction solution is preferably 0.005 to 5 mol/L, more preferably 0.1 to 2 mol/L.

The reaction temperature is preferably 10 to 150° C., more preferably 50 to 120° C.

The reaction time is appropriately selected depending on the conditions such as reaction temperature, and satisfactory results are usually obtained when the selected reaction time is about 30 minutes to about 24 hours.

With regard to the aniline derivative represented by Formula (IX), a desired isomer(s) can be obtained by a commonly used technique (for example, optical resolution, diastereomer resolution and the like) as required.

Among the aniline derivatives that are a raw material in Scheme 1, aniline derivatives having a 2,2,2-trifluoro-1-hydroxyethyl group and a cyclic amino substituent as represented by Formula (XI) can be produced by the method shown in Scheme 3.

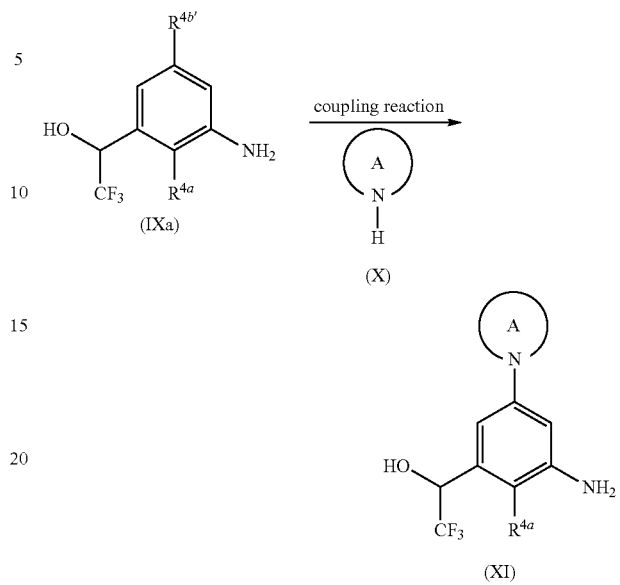

Scheme 3

In Scheme 3, $R^{4b'}$ represents bromo or iodo; the compound containing the A as represented by Formula (X) represents a cyclic secondary amine.

The cyclic amino substituted aniline derivative represented by Formula (XI) can be synthesized by reacting the cyclic secondary amine represented by Formula (X) to the aniline derivative represented by Formula (IXa) in the presence of a metal catalyst, a ligand and a base and in an appropriate solvent.

Examples of the above-mentioned metal catalyst include, for example, palladium catalysts such as tris(dibenzylideneacetone)dipalladium, palladium acetate and tetrakis(triphenylphosphine)palladium; and copper catalysts such as copper oxide and copper iodide, but a copper catalyst is preferable.

The amount of the above-mentioned metal catalyst to be used is preferably 0.001 to 1 mol, more preferably 0.01 to 0.5 mol, with respect to 1 mol of the aniline derivative represented by Formula (IXa).

The ligand of the metal catalyst is appropriately selected according to the metal catalyst. Examples of the ligand for the palladium catalyst include, for example, phosphine derivatives such as triphenylphosphine, 2,2'-bis(diphenylphosphino)-1,1'-binaphthyl and 4,5-bis(diphenylphosphino)-9,9-dimethylxanthene, but 4,5-bis(diphenylphosphino)-9,9-dimethylxanthene is preferable. Examples of the ligand for the copper catalyst include, for example, amino acid derivatives such as proline and N,N-dimethylglycine.

The amount of the above-mentioned ligand to be used is preferably 0.001 to 1 mol, more preferably 0.01 to 0.5 mol, with respect to 1 mol of the aniline derivative represented by Formula (IXa).

Examples of the base to be made to coexist include, for example, alkali metal carbonates such as sodium carbonate and potassium carbonate; alkali metal hydrogen carbonates such as sodium hydrogen carbonate and potassium hydrogen carbonate; alkali metal phosphate salts such as sodium phosphate and potassium phosphate; and alkali metal hydrogen phosphates such as sodium hydrogen phosphate, potassium hydrogen phosphate, sodium dihydrogen phosphate and potassium dihydrogen phosphate, but an alkali metal carbonate is preferable.

The amount of the base to be used to be made to coexist is preferably 1 to 10 mol, more preferably 1 to 5 mol, with respect to 1 mol of the aniline derivative represented by Formula (IXa).

The amount of the above-mentioned cyclic secondary amine to be used is preferably 1 to 20 mol, more preferably 1 to 10 mol, with respect to 1 mol of the aniline derivative represented by Formula (IXa).

Usually, as the reaction solvent, a solvent that does not inhibit the reaction is appropriately selected. Examples thereof include, for example, ether solvents such as THF, 1,4-dioxane and ethylene glycol dimethyl ether; and aprotic polar solvents such as DMF and DMSO, but an aprotic polar solvent is preferable.

The concentration of the aniline derivative represented by Formula (IXa) in the reaction solution is preferably 0.005 to 5 mol/L, more preferably 0.01 to 2 mol/L.

The reaction temperature is preferably 0 to 200° C., more preferably 30 to 150° C.

The reaction time is appropriately selected depending on the conditions such as reaction temperature, and satisfactory results are usually obtained when the selected reaction time is about 1 to 48 hours.

Among the aldehyde derivatives that are a raw material in Scheme 2, benzaldehyde derivatives having a methylcycloalkane as represented by Formula (XVI) can be synthesized according to Scheme 4.

Scheme 4

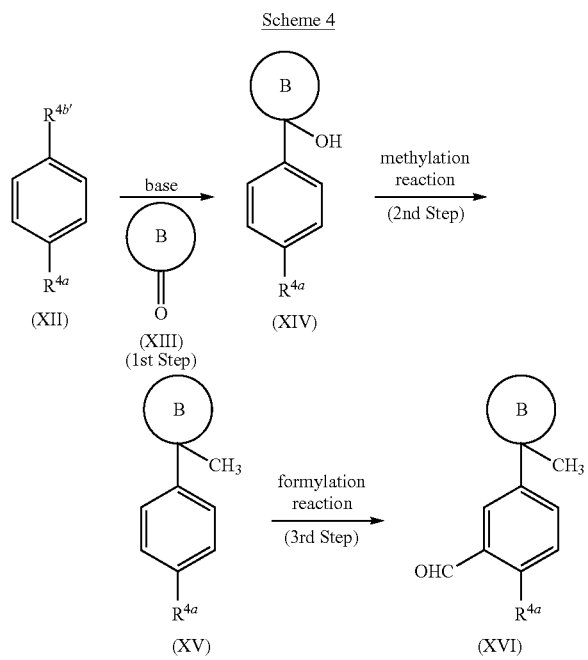

In Scheme 4, $R^{4b'}$ represents bromo or iodo; the compound containing the B as represented by Formula (XIII) represents a cycloalkanone.

1st Step

The hydroxycycloalkane derivative represented by Formula (XIV) can be synthesized by reacting the cycloalkanone represented by Formula (XIII) to an intermediate obtained by reacting a base to the aryl halide compound represented by Formula (XII) in an appropriate solvent.

Examples of the base to be used include, for example, alkyllithiums such as n-butyllithium and sec-butyllithium; alkyl Grignard reagents such as isopropylmagnesium chloride and cyclohexylmagnesium chloride; and alkali metal alkoxides such as potassium tert-butoxide, but an alkyllithium is preferable.

The amount of the base to be used is preferably 0.5 to 10 mol, more preferably 1 to 5 mol, with respect to 1 mol of the aryl halide compound represented by Formula (XII).

The amount of the above-mentioned cycloalkanone is preferably 1 to 20 mol, more preferably 1 to 5 mol, with respect to 1 mol of the aryl halide compound represented by Formula (XII).

Usually, as the reaction solvent, a solvent that does not inhibit the reaction is appropriately selected. Examples thereof include, for example, ether solvents such as THF, 1,4-dioxane and ethylene glycol dimethyl ether, but THF is preferable.

The concentration of the aryl halide compound represented by Formula (XII) in the reaction solution is preferably 0.01 to 5 mol/L, more preferably 0.05 to 3 mol/L.

The reaction temperature is preferably −100 to 50° C., more preferably −80 to 20° C.

The reaction time is appropriately selected depending on the conditions such as reaction temperature, and satisfactory results are usually obtained when the selected reaction time is about 30 minutes to about 12 hours.

2nd Step

The methylcycloalkane derivative represented by Formula (XV) can be synthesized by reacting a methylating agent to the hydroxycycloalkane derivative represented by Formula (XIV) in an appropriate solvent in the presence of a Lewis acid.

Examples of the Lewis acid to be made to coexist include, for example, metal chlorides such as aluminum chloride, titanium chloride and zinc chloride, but titanium chloride is preferable.

The amount of the above-mentioned Lewis acid to be used is preferably 0.5 to 10 mol, more preferably 1 to 5 mol, with respect to 1 mol of the hydroxycycloalkane derivative represented by Formula (XIV).

Examples of the above-mentioned methylating agent include, for example, methyllithium, methylmagnesium bromide and dimethylzinc, but dimethylzinc is preferable.

The amount of the above-mentioned methylating agent to be used is preferably 1 to 20 mol, more preferably 1 to 10 mol, with respect to 1 mol of the hydroxycycloalkane derivative represented by Formula (XIV).

Usually, as the reaction solvent, a solvent that does not inhibit the reaction is appropriately selected. Examples thereof include, for example, halogenated solvents such as dichloromethane, chloroform, 1,2-dichloroethane and carbon tetrachloride; and ether solvents such as THF, 1,4-dioxane and ethylene glycol dimethyl ether, but a halogenated solvent is preferable.

The concentration of the hydroxycycloalkane derivative represented by Formula (XIV) in the reaction solution is preferably 0.01 to 5 mol/L, more preferably 0.05 to 2 mol/L.

The reaction temperature is preferably −100 to 0° C., more preferably −90 to −30° C.

The reaction time is appropriately selected depending on the conditions such as reaction temperature, and satisfactory results are usually obtained when the selected reaction time is about 30 minutes to about 6 hours.

3rd Step

The benzaldehyde derivative represented by Formula (XVI) can be synthesized by reacting a formylating agent to the methylcycloalkane derivative represented by Formula (XV) in an appropriate solvent in the presence of a Lewis acid.

Examples of the Lewis acid to be made to coexist include, for example, metal chlorides such as aluminum chloride, titanium chloride and zinc chloride, but titanium chloride is preferable.

The amount of the above-mentioned Lewis acid to be used is preferably 0.5 to 10 mol, more preferably 1 to 5 mol, with respect to 1 mol of the methylcycloalkane derivative represented by Formula (XV).

As the formylating agent as mentioned above, dichloromethyl methyl ether is preferable.

The amount of the above-mentioned formylating agent to be used is preferably 1 to 20 mol, more preferably 1 to 10 mol, with respect to 1 mol of the methylcycloalkane derivative represented by Formula (XV).

Usually, as the reaction solvent, a solvent that does not inhibit the reaction is appropriately selected. Examples thereof include, for example, halogenated solvents such as dichloromethane, chloroform, 1,2-dichloroethane and carbon tetrachloride; and ether solvents such as THF, 1,4-dioxane and ethylene glycol dimethyl ether, but a halogenated solvent is preferable.

The concentration of the methylcycloalkane derivative represented by Formula (XV) in the reaction solution is preferably 0.01 to 5 mol/L, more preferably 0.05 to 2 mol/L.

The reaction temperature is preferably −100 to 0° C., more preferably −90 to −30° C.

The reaction time is appropriately selected depending on the conditions such as reaction temperature, and satisfactory results are usually obtained when the selected reaction time is about 30 minutes to about 6 hours.

The 2-amino-2,3-dihydro-1H-indene compound represented by Formula (V):

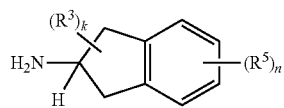

(V)

may be synthesized by the methods as described in documents (for example, *Tetrahedron Letters*, 1993, Vol. 34, No. 52, pp. 8399-8402; YAKUGAKU ZASSHI, 1979, Vol. 99, No. 11, pp. 1111-1115; and *Tetrahedron: Asymmetry*, 1995, Vol. 6, No. 7, pp. 1535-1538).

As required, the compound represented by Formula (V) may also be obtained as an amine that is an optically active substance by performing optical resolution by the methods as described in documents (for example, *Tetrahedron: Asymmetry*, 1995, Vol. 6, No. 7, pp. 1535-1538 or the like) using an optically active acid.

Examples of the above-mentioned optically active acid include carboxylic acids such as lactic acid, tartaric acid, 2-phenylpropionic acid and mandelic acid; acidic amino acids such as glutamic acid and aspartic acid; and sulfonic acids such as camphorsulfonic acid, but satisfactory results are obtained by appropriately selecting depending on the compound.

The effect of Compound (I) or a pharmaceutically acceptable salt thereof on allergic dermatitis may be evaluated based on the inhibitory action on the skin swelling response induced by an antigen by using the methods described in documents concerning a type I allergic dermatitis model (see, for example, *Inflamm. Res.*, 1998, Vol. 47, pp. 506-511), a type IV allergic dermatitis model (see, for example, *Int. Arch. Allergy. Appl. Immunol.*, 1990, Vol. 92, pp. 356-360) or the like. It is known that the dermatitis reaction observed in the models is similar to the swelling response observed when an antigen is applied to a human patient suffering from allergic dermatitis. This method is also used as an animal model of atopic dermatitis.

Compound (I) or a pharmaceutically acceptable salt thereof can be used for ameliorating allergic dermatitis induced by an antigen, more specifically, diffuse neurodermatitis, atopic eczema, atopic neurodermatitis, Besnier's prurigo, acute infantile eczema, flexural eczema, infantile eczema on the limbs, childhood atopic eczema, infantile xerotic eczema, infantile eczema, adult atopic dermatitis, endogenic eczema, infantile dermatitis, chronic infantile eczema and the like.

Examples of the antigen herein include, for example, mite allergens (*Dermatophagoides farinae, Dermatophagoides pteronyssinus* and the like), food allergens (albumen, milk, wheat, soybean, rice, corn, sesame, buckwheat and the like), pollen antigens (ragweed, mugwort, goldenrod, vernal grass, orchard grass, bermuda grass, timothy grass, reed grass and the like), fungus allergens (*Candida, Penicillium, Cladosporium, Aspergillus, Alternaria* and the like), animal epithelium allergens (cat, dog) and hapten antigens (2,4-dinitrofluorobenzene (hereinafter referred to as DNFB), DNP, TNP and the like).

In addition, Compound (I) or a pharmaceutically acceptable salt thereof can be used for ameliorating symptoms associated with allergic dermatitis, more specifically, erythema, papule, scale, incrustation, lichenification, xerosis (dry skin), pruritus, xeroderma, cheilitis, keratosis pilaris, darkening of eyelids, facial pallor, pityriasis alba, food intolerance, white dermographism, delayed blanch response and the like.

The effect of Compound (I) or a pharmaceutically acceptable salt thereof on inflammatory bowel disease may be evaluated based on the inhibitory action on the colonic disorders induced by TNBS or DSS by using the methods described in documents concerning a 2,4,6-trinitrobenzenesulfonic acid (hereinafter referred to as TNBS)-induced colitis model (see, for example, *Gastroenterology*, 1989, Vol. 96, pp. 29-36), a dextran sulfate sodium (hereinafter referred to as DSS)-induced chronic colitis model (see, for example, *Am. J. Physiol. Gastrointest. Liver Physiol.*, 2004, Vol. 287, pp. G115-124) or the like. It is known that the TNBS-induced colitis model is similar to human Crohn's disease and the DSS-induced chronic colitis model is similar to human ulcerative colitis (see, for example, *Gastroenterology*, 2002, Vol. 37, pp. 409-417).

Compound (I) or a pharmaceutically acceptable salt thereof can be used for ameliorating inflammatory bowel disease, more specifically, Crohn's disease, ulcerative colitis and the like.

In addition, Compound (I) or a pharmaceutically acceptable salt thereof can be used for ameliorating symptoms associated with inflammatory bowel disease, more specifically, diarrhea, abdominal pain, fever, blood stool, mucous and blood stool, anorexia, weight loss, anemia, vomiting, melena, abdominal tumor, general malaise and the like.

The effect of Compound (I) or a pharmaceutically acceptable salt thereof on pain may be evaluated based on the inhibitory action on pain induced by administration of an inflammatory agent (for example, carrageenin) or by surgical nerve damage, by using the methods described in documents concerning an inflammatory pain model (see, for example, *Anesth. Analg.*, 2009, Vol. 108, pp. 1680-1687), neuropathic pain models as typified by Bennett model and Chung model (see, for example, *Pain*, 1988, Vol. 33, pp. 87-107; and *Pain*, 1992, Vol. 50, pp. 355-363) or the like.

Compound (I) or a pharmaceutically acceptable salt thereof can be used for ameliorating pain, more specifically, inflammatory pain and neuropathic pain. Examples of the inflammatory pain and neuropathic pain herein include, for example, headache, toothache, chest pain, abdominal pain, arthritis pain, trigeminal neuralgia, sciatic neuralgia, diabetic neuropathic pain, cancer neuropathic pain, HIV-related neuropathic pain, postherpetic neuralgia and post spinal cord injury pain.

Compound (I) or a pharmaceutically acceptable salt thereof can be used as a pharmaceutical for a mammal (for example, mouse, rat, hamster, rabbit, cat, dog, monkey, bovine, sheep or human).

When Compound (I) is used as a pharmaceutical, its free form or a pharmaceutically acceptable salt thereof may be used for systemic or topical action as it is or after blending with a carrier acceptable as a pharmaceutical.

Examples of the form of administration include, for example, oral preparations such as tablets, capsules, granules, fine granules, powders, syrups and liquids; and parenteral preparations such as injection solutions, inhalants, suppositories, nasal drops, eye drops, lotions, ointments, creams, adhesive preparations and patches.

Preparation of a formulation containing Compound (I) or a pharmaceutically acceptable salt thereof may be carried out according to a known production method commonly used in the field of pharmaceutical formulations. In this case, an excipient(s), a binder(s), a lubricant(s), a disintegrator(s), a sweetener(s), a surfactant(s), a suspending agent(s), an emulsifier(s), a pH adjustor(s), a base(s) and/or the like commonly used in the field of pharmaceutical formulations may be contained as required.

Examples of the above-mentioned excipient include, for example, lactose, saccharose, sucrose, sorbitol, mannitol, erythritol, crystalline cellulose, corn starch, gelatin, dextran and low substituted hydroxypropylcellulose.

Examples of the above-mentioned binder include, for example, starch, gum arabic, gelatin, tragacanth, carboxymethylcellulose, methylcellulose, hydroxypropylcellulose, hydroxyl-propylmethylcellulose, polyvinylpyrrolidone, polyvinyl alcohol, sodium alginate and glycerin.

Examples of the above-mentioned lubricant include, for example, magnesium stearate, calcium stearate, stearic acid, sucrose fatty acid ester, light anhydrous silicic acid and talc.

Examples of the above-mentioned disintegrator include, for example, starch, crystalline cellulose, low substituted hydroxypropylcellulose, croscarmellose sodium, crospovidone, carmellose calcium and partially pregelatinized starch.

Examples of the above-mentioned sweetener include, for example, glucose, fructose, invert sugar, sorbitol, xylitol, glycerin and simple syrup.

Examples of the above-mentioned surfactant include, for example, sodium lauryl sulfate, polysorbate 80, sorbitan monofatty acid ester and polyoxyl 40 stearate.

Examples of the above-mentioned suspending agent include, for example, gum arabic, sodium alginate, sodium carboxymethylcellulose, methylcellulose and bentonite.

Examples of the above-mentioned emulsifier include, for example, gum arabic, tragacanth, gelatin and polysorbate 80.

Examples of the above-mentioned pH adjustor include, for example, phosphoric acid, tartaric acid, citric acid, glutamic acid, sodium hydroxide and magnesium oxide.

Examples of the above-mentioned base include, for example, petrolatum, platinum base, polyethyleneglycol, polyethylene oxide, polypropylene glycol, glycerin, liquid paraffin, hydrophilic ointment and absorptive ointment.

When a formulation containing Compound (I) or a pharmaceutically acceptable salt thereof is prepared into a dosage form as mentioned above, a coloring agent(s), a light shading agent(s), a preservative(s), a flavoring agent(s), a corrigent(s), an isotonic agent(s), a stabilizer(s), a solubilizer(s), a thickener(s), a coating agent(s), a sustained release base(s) and/or the like commonly used in the field of pharmaceutical formulations may be used.

The content of the Compound (I) or the pharmaceutically acceptable salt thereof as an effective ingredient in the above formulation is preferably 0.001 to 90% by weight, more preferably 0.01 to 70% by weight.

The dosage of the Compound (I) or the pharmaceutically acceptable salt thereof is appropriately selected depending on the symptom(s), age, body weight and/or sex of the patient, and/or administration method and the like. The amount of the effective ingredient per day for an adult is, in case of an injection solution, preferably 0.01 mg to 25 g, more preferably 0.1 mg to 10 g; and, in case of an oral preparation, preferably 0.1 mg to 50 g, more preferably 1 mg to 20 g. In addition, in case of a topical preparation, the concentration of the effective ingredient to be administered to an affected area in one time or in several times is preferably 0.0001 to 10%, more preferably 0.001 to 5%.

Compound (I) or a pharmaceutically acceptable salt thereof may be used alone, but may be also used after blending with or in combination with an appropriate amount of other agent(s) for treating or preventing a disease, for reducing or suppressing a symptom(s), for complementing or enhancing a prophylactic and/or therapeutic effect(s) or for decreasing the dosage.

Examples of other agents that can be used after blending or in combination include, for example, steroids (such as prednisolone, methylprednisolone, hydrocortisone, betamethasone and budesonide), immunosuppressive agents (such as mercaptopurine, methotrexate, azathioprine, cyclosporine and tacrolimus), petrolatums, urea ointments, zinc oxide ointments, antihistaminic agents (such as chlorpheniramine), antiallergic agents (sodium cromoglycate), Th2 cytokine inhibitors (such as suplatast), NFκB decoy DNAs, adhesion molecule inhibitors, active oxygen scavengers, active oxygen production inhibitors, antibiotics (such as metronidazole), antibacterial agents, aminosalicylic acid preparations (such as salazopyrin and mesalazine) and derivatives thereof, prostaglandin synthetase inhibitors, protease inhibitors (such as ulinastatin), leukotriene production inhibitors, leukotriene receptor antagonists, TNFα antagonists, IL-6 antagonists, 5-lipoxygenase inhibitors, elastase inhibitors, metalloprotease inhibitors, PDE inhibitors, mucosal protective agents, mucosal repairing agents, adrenocorticotropic hormones, antitussives, expectorants, antitussive and expectorant agents, bronchodilators, antipeptic ulcer agents and narcotic analgesics.

EXAMPLES

Our derivatives and methods will now be described concretely by way of Examples below, although they are not restricted thereto.

Example 1

Synthesis of 1-(5-tert-butyl-3-(hydroxymethyl)-2-methoxyphenyl)-3-((1S,2R)-1-hydroxy-2,3-dihydro-1H-indene-2-yl)urea (Compound 1)

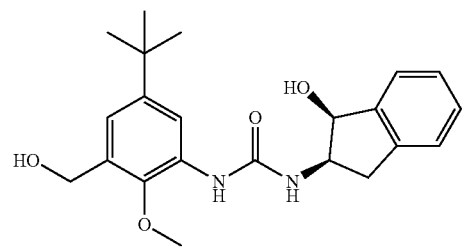 [SMILES: COc1c(CO)cc(C(C)(C)C)cc1NC(=O)N[C@@H]1Cc2ccccc2[C@@H]1O]

1st Step

Synthesis of 5-tert-butyl-2-methoxy-3-nitrobenzaldehyde

A solution of 5-tert-butyl-2-hydroxybenzaldehyde (7.71 g, 43.3 mmol) in acetonitrile (216 mL) was cooled to −40° C., and nitronium tetrafluoroborate (7.47 g, 56.2 mmol) was added thereto. The resulting mixture was stirred for 1 hour while raising the temperature to −20° C. Water was added to the reaction solution and the aqueous layer was extracted with ethyl acetate. The organic layer was washed with saturated brine. The organic layer was dried over anhydrous sodium sulfate and filtered, and then the solvent was evaporated under reduced pressure. To a suspension of the obtained residue (8.35 g) and potassium carbonate (25.9 g, 187 mmol) in DMF (50.0 mL), methyl iodide (8.19 mL, 131 mmol) was added, and the resulting mixture was stirred at room temperature for 15 hours. Water was added to the reaction solution and the resulting mixture was extracted with diethyl ether. The organic layer was washed with water and then with saturated brine. The organic layer was dried over anhydrous sodium sulfate and filtered, and the solvent was evaporated under reduced pressure. The obtained residue was purified by column chromatography (silica gel, hexane/ethyl acetate=100/0-80/20) to obtain 7.49 g of the captioned compound (84% yield in 2 steps).

2nd Step

Synthesis of (5-tert-butyl-2-methoxy-3-nitrophenyl)methanol

A solution of 5-tert-butyl-2-methoxy-3-nitrobenzaldehyde (0.500 g, 2.10 mmol) in methanol (10.5 mL) was cooled to 0° C., and sodium borohydride (0.088 g, 2.31 mmol) was added thereto, followed by stirring the mixture for 15 minutes. Saturated aqueous ammonium chloride solution was added to the reaction solution and the mixture was stirred at room temperature for 10 minutes. The aqueous layer was extracted with ethyl acetate, and the organic layer was washed with saturated brine. The organic layer was dried over anhydrous sodium sulfate and filtered, and then the solvent was evaporated under reduced pressure. The obtained residue was purified by column chromatography (silica gel, hexane/ethyl acetate=10/90-50/50) to obtain 0.486 g of captioned compound (96% yield).

3rd Step

Synthesis of (3-amino-5-tert-butyl-2-methoxyphenyl)methanol

To a solution of (5-tert-butyl-2-methoxy-3-nitrophenyl) methanol (0.250 g, 1.04 mmol) in ethyl acetate (10.4 mL), 10% palladium/activated charcoal (0.025 g) was added and the resulting mixture was stirred at room temperature under hydrogen atmosphere for 14 hours. After completion of the reaction, insoluble materials were filtered through a Celite pad, and the solvent was washed with ethyl acetate. The solvent of the filtrate was evaporated under reduced pressure to obtain 0.219 g (quantitative) of the crude product containing the captioned compound.

4th Step

Synthesis of 2,2,2-trichloroethyl 5-tert-butyl-3-(hydroxymethyl)-2-methoxyphenylcarbamate A solution of (3-amino-5-tert-butyl-2-methoxyphenyl) methanol (1.72 g, 8.23 mmol) and N,N-diisopropylethylamine (2.15 mL, 12.3 mmol) in THF (27.4 mL) was cooled to 0° C., and 2,2,2-trichloroethyl chloroformate (1.24 mL, 9.01 mmol) was added, followed by stirring the mixture for 10 minutes. Water was added to the reaction solution and the aqueous layer was extracted with ethyl acetate and then the organic layer was washed with saturated brine. The organic layer was dried over anhydrous sodium sulfate and filtered, and then the solvent was evaporated under reduced pressure. The obtained residue was purified by column chromatography (silica gel, hexane/ethyl acetate=75/25-50/50) to obtain 2.23 g of the captioned compound (71% yield).

5th Step

Synthesis of 1-(5-tert-butyl-3-(hydroxymethyl)-2-methoxyphenyl)-3-((1S,2R)-1-hydroxy-2,3-dihydro-1H-indene-2-yl)urea (Compound 1)

A suspension of 2,2,2-trichloroethyl 5-tert-butyl-3-(hydroxymethyl)-2-methoxyphenylcarbamate (1.50 g, 3.90 mmol), (1S,2R)-2-amino-2,3-dihydro-1H-indene-1-ol.L-tartaric acid salt (1.28 g, 4.29 mmol) and N,N-diisopropylethylamine (2.37 mL, 13.6 mmol) in acetonitrile (19.5 mL) was heated to reflux. After 17 hours, the mixture was allowed to cool and the reaction solution was concentrated under reduced pressure. The obtained residue was purified by column chromatography (silica gel, hexane/ethyl acetate=50/50-0/100) to obtain 1.09 g of the captioned compound (73% yield).

Example 2

Synthesis of 1-(5-tert-butyl-3-(hydroxymethyl)-2-methoxyphenyl)-3-((1S,2R)-4-fluoro-1-hydroxy-2,3-dihydro-1H-indene-2-yl)urea (Compound 3)

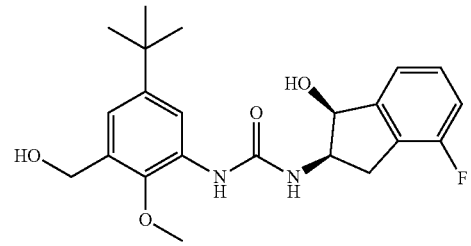 [SMILES: COc1c(CO)cc(C(C)(C)C)cc1NC(=O)N[C@@H]1Cc2c(F)cccc2[C@@H]1O]

Using 2,2,2-trichloroethyl 5-tert-butyl-3-(hydroxymethyl)-2-methoxyphenylcarbamate (0.100 g, 0.260 mmol) and (1S,2R)-2-amino-4-fluoro-2,3-dihydro-1H-indene-1-ol.L-tartaric acid salt (0.091 g, 0.286 mmol), the same reaction as in Example 1 (5th Step) was carried out to obtain 0.034 g of the captioned compound (32% yield).

Example 3

Synthesis of 1-(5-tert-butyl-2-methoxy-3-((S)-2,2,2-trifluoro-1-hydroxyethyl)phenyl)-3-((1S,2R)-1-hydroxy-2,3-dihydro-1H-indene-2-yl)urea (Compound 46a), 1-(5-tert-butyl-2-methoxy-3-((R)-2,2,2-trifluoro-1-hydroxyethyl)phenyl)-3-((1S,2R)-1-hydroxy-2,3-dihydro-1H-indene-2-yl)urea (Compound 46b)

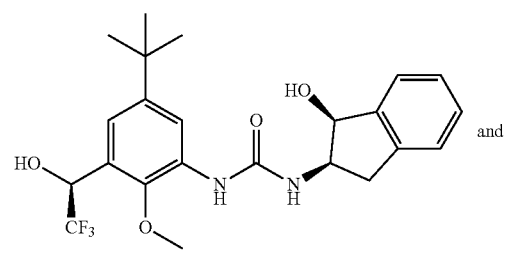

-continued

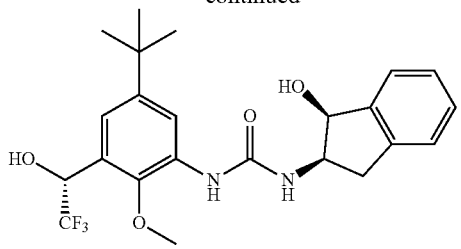

1st Step

Synthesis of 1-(5-tert-butyl-2-methoxy-3-nitrophenyl)-2,2,2-trifluoroethanol

A solution of 5-tert-butyl-2-methoxy-3-nitrobenzaldehyde (13.5 g, 57.1 mmol) in THF (57.1 mL) was cooled to 0° C., and trimethyl(trifluoromethyl)silane (10.9 mL, 74.2 mmol) and a solution of 1.0 mol/L tetra n-butylammonium fluoride in THF (5.71 mL, 5.71 mmol) were added dropwise thereto, respectively. After addition of the reagents, the mixture was heated to room temperature. After stirring the mixture for 3 hours, 1 mol/L hydrochloric acid was added to the reaction solution, and the resulting mixture was stirred at room temperature for 2 hours. The aqueous layer was extracted with ethyl acetate. The organic layer was washed with saturated brine. The organic layer was dried over anhydrous sodium sulfate and filtered, and the solvent was evaporated under reduced pressure. The obtained residue was purified by column chromatography (silica gel, hexane/ethyl acetate=100/0-50/50) to obtain 16.5 g of captioned compound (94% yield).

2nd Step

Synthesis of 1-(3-amino-5-tert-butyl-2-methoxyphenyl)-2,2,2-trifluoroethanol

To a solution of 1-(5-tert-butyl-2-methoxy-3-nitrophenyl)-2,2,2-trifluoroethanol (0.440 g, 1.43 mmol) in ethanol (4.7 mL) and water (2.3 mL), ammonium chloride (0.230 g, 4.30 mmol) and iron powder (0.240 g, 4.30 mmol) were added, and the resulting mixture was heated to reflux for 15 hours. The temperature of the reaction solution was returned to room temperature, the insoluble materials were filtered through a Celite pad. After evaporating the organic solvent under reduced pressure, the aqueous layer was extracted with ethyl acetate, and the organic layer was washed with saturated brine. The organic layer was dried over anhydrous sodium sulfate and filtered, and the solvent was evaporated under reduced pressure to obtain 0.397 g of the crude product containing the captioned compound.

3rd Step

Synthesis of 2,2,2-trichloroethyl 5-tert-butyl-2-methoxy-3-(2,2,2-trifluoro-1-hydroxyethyl)phenylcarbamate A solution of crude product (0.397 g) containing 1-(3-amino-5-tert-butyl-2-methoxyphenyl)-2,2,2-trifluoroethanol and N,N-diisopropylethylamine (0.374 mL, 2.14 mmol) in THF (4.77 mL) was cooled to 0° C., and 2,2,2-trichloroethyl chloroformate (0.217 mL, 1.57 mmol) was added thereto, followed by stirring the mixture for 10 minutes. Water was added to the reaction solution and the aqueous layer was extracted with ethyl acetate and the organic layer was washed with saturated brine. The organic layer was dried over anhydrous sodium sulfate and filtered, and then the solvent was evaporated under reduced pressure. The obtained residue was purified by column chromatography (silica gel, hexane/ethyl acetate=100/0-75/25) to obtain 0.622 g of the captioned compound (96% yield in 2 steps).

4th Step

Synthesis of 1-(5-tert-butyl-2-methoxy-3-((S)-2,2,2-trifluoro-1-hydroxyethyl)phenyl)-3-((1S,2R)-1-hydroxy-2,3-dihydro-1H-inden-2-yl)urea (Compound 46a) and 1-(5-tert-butyl-2-methoxy-3-((R)-2,2,2-trifluoro-1-hydroxyethyl)phenyl)-3-((1S,2R)-1-hydroxy-2,3-dihydro-1H-inden-2-yl)urea (Compound 46b)

A suspension of 2,2,2-trichloroethyl 5-tert-butyl-2-methoxy-3-(2,2,2-trifluoro-1-hydroxyethyl)phenylcarbamate (0.220 g, 0.486 mmol), (1S,2R)-2-amino-2,3-dihydro-1H-indene-1-ol.L-tartaric acid salt (0.189 g, 0.632 mmol) and N,N-diisopropylethylamine (0.423 mL, 2.43 mmol) in acetonitrile (0.486 mL) was heated to reflux. After 14 hours, the mixture was allowed to cool, the reaction solution was concentrated under reduced pressure. The obtained residue was purified by column chromatography (silica gel, hexane/ethyl acetate=67/33-0/100) to obtain 0.095 g of the captioned compound 46a (43% yield) in the low polarity side and 0.095 g of the captioned compound 46b (43% yield) in the high polarity side.

Example 4

Synthesis of 1-(3-(1-amino-2,2,2-trifluoroethyl)-5-tert-butyl-2-methoxyphenyl)-3-((1S,2R)-1-hydroxy-2,3-dihydro-1H-inden-2-yl)urea (Compound 47a, Compound 47b)

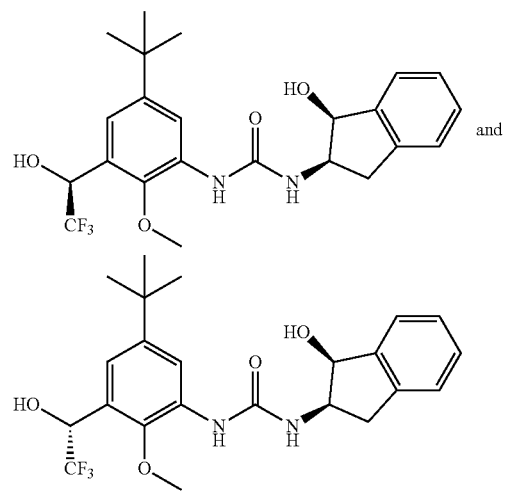

1st Step

Synthesis of tert-butyl 1-(5-tert-butyl-2-methoxy-3-nitrophenyl)-2,2,2-trifluoroethylcarbamate To a solution of 1-(5-tert-butyl-2-methoxy-3-nitrophenyl)-2,2,2-trifluoroethanol (0.500 g, 1.62 mmol) in acetonitrile (13 mL), 1.30 mL (24.4 mmol) of concentrated sulfuric acid was added, and the resulting mixture was heated to reflux for 2 hours. After completion of the reaction, the reaction solution was allowed to cool and added to aqueous saturated sodium hydrogen carbonate solution, and the pH was adjusted to 8.

The aqueous layer was extracted with ethyl acetate. The organic layer was washed with saturated brine, dried over anhydrous sodium sulfate and filtered, and the solvent was evaporated under reduced pressure. To a solution of the obtained residue in THF (20 mL), triethylamine (0.32 mL, 2.31 mmol), di tert-butyldicarbonate (0.510 g, 2.31 mmol) and 4-(dimethylamino)pyridine (0.024 g) were added, and the resulting mixture was stirred at room temperature for 4 hours. After completion of the reaction, methanol was added and the solvent was evaporated under reduced pressure. The obtained residue was purified by column chromatography (silica gel, hexane/ethyl acetate=90/10-0/100) to obtain 0.599 g of the captioned compound (97% yield).

2nd Step

Synthesis of tert-butyl 1-(5-tert-butyl-3-(3-((1S,2R)-1-hydroxy-2,3-dihydro-1H-inden-2-yl)ureido)-2-methoxyphenyl)-2,2,2-trifluoroethylcarbamate To a solution of tert-butyl 1-(5-tert-butyl-2-methoxy-3-nitrophenyl)-2,2,2-trifluoroethyl carbamate (0.645 g, 1.58 mmol) in methanol (20 mL), 10% palladium/activated charcoal (0.130 g) was added and the resulting mixture was stirred at room temperature under hydrogen atmosphere for 3 hours. After completion of the reaction, insoluble materials were filtered through a Celite pad, and the solvent was evaporated under reduced pressure. To a solution of the obtained residue in THF (7.0 mL), N,N-diisopropylethylamine (0.360 mL, 2.06 mmol) was added, and 2,2,2-trichloroethyl chloroformate (0.235 mL, 1.74 mmol) was added under ice cooling. The temperature was returned to room temperature and the mixture was stirred for 30 minutes. After completion of the reaction, methanol was added and the solvent was evaporated under reduced pressure to obtain 0.768 g of an oily product. Using this oily product (0.300 g) and (1S,2R)-2-amino-2,3-dihydro-1H-inden-1-ol.L-tartaric acid salt (0.220 g, 0.735 mmol), the same reaction as in Example 3 (4th Step) was carried out to obtain 0.185 g of the captioned compound (54% yield in 3 steps).

3rd Step

Synthesis of 1-(3-(1-amino-2,2,2-trifluoroethyl)-5-tert-butyl-2-methoxyphenyl)-3-((1S,2R)-1-hydroxy-2,3-dihydro-1H-inden-2-yl)urea (Compound 47a, Compound 47b)

In 10% hydrogen chloride/methanol solution (6.0 mL), tert-butyl 1-(5-tert-butyl-3-(3-((1S,2R)-1-hydroxy-2,3-dihydro-1H-inden-2-yl)ureido)-2-methoxyphenyl)-2,2,2-trifluoroethylcarbamate (0.183 g, 0.332 mmol) was dissolved and the resulting mixture was stirred at room temperature for 28 hours. After completion of the reaction, the solvent was evaporated under reduced pressure. To the obtained residue, ethyl acetate and 1 mol/L aqueous sodium hydroxide solution were added, and the pH was adjusted to 10. The aqueous layer was extracted with ethyl acetate. The organic layer was washed with saturated brine, dried over anhydrous sodium sulfate and filtered, and the solvent was evaporated under reduced pressure. The obtained residue was purified by column chromatography (silica gel, hexane/ethyl acetate=90/10-0/100) to obtain 0.064 g of the captioned compound 47a (43% yield) in the low polarity side and 0.049 g of the captioned compound 47b (33% yield) in the high polarity side.

Example 5

Synthesis of 1-(5-tert-butyl-2-methoxy-3-(2,2,2-trifluoro-1-(methylamino)ethyl)phenyl)-3-((1S,2R)-1-hydroxy-2,3-dihydro-1H-inden-2-yl)urea (Compound 48a, Compound 48b)

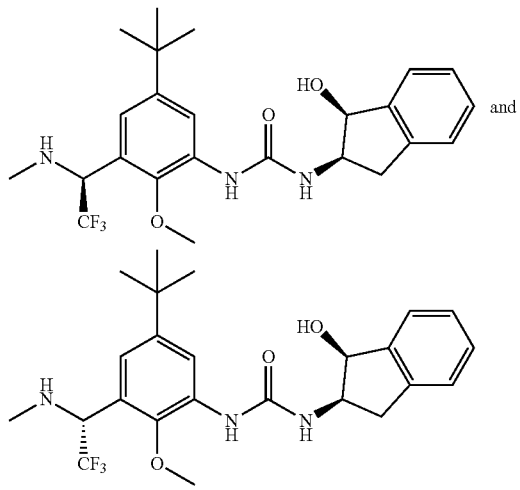

and

1st Step

Synthesis of 1-(5-tert-butyl-2-methoxy-3-nitrophenyl)-2,2,2-trifluoroethanone

To a solution of 1-(5-tert-butyl-2-methoxy-3-nitrophenyl)-2,2,2-trifluoroethanol (2.00 g, 6.51 mmol) in dichloromethane (32.5 mL), Dess-Martin Periodinane (2.90 g, 6.83 mmol) was added, and the resulting mixture was stirred at room temperature for 14 hours. The insoluble materials were filtered through a Celite pad, and the solvent was evaporated under reduced pressure. The obtained residue was purified by column chromatography (amine coated silica gel, hexane/ethyl acetate=75/25-10/90) to obtain 1.81 g of the captioned compound (91% yield).

2nd Step

Synthesis of 1-(5-tert-butyl-2-methoxy-3-nitrophenyl)-2,2,2-trifluoro-N-methylethaneamine To a solution of 145-tert-butyl-2-methoxy-3-nitrophenyl)-2,2,2-trifluoroethanone (0.500 g, 1.63 mmol), methylaminehydrochloride (0.221 g, 3.28 mmol) and triethylamine (0.454 mL, 3.28 mmol) in ethanol (5.0 mL), titanium tetraisopropoxide (0.960 mL, 3.28 mmol) was added dropwise thereto, followed by stirring the mixture overnight at room temperature. The reaction solution was cooled to 0° C. and sodium borohydride (0.062 g, 1.63 mmol) was added thereto. The temperature was returned to room temperature and the mixture was stirred. After completion of the reaction, water was added and the insoluble materials were filtered through a Celite pad, and the solvent was evaporated under reduced pressure. To a solution, chloroform and saturated aqueous sodium hydrogen carbonate solution was added, and aqueous layer was extracted with chloroform. The organic layer was washed with saturated brine, and dried over anhydrous sodium sulfate and filtered, and the solvent was evaporated under reduced pressure. The obtained residue was purified by column chromatography (amine coated silica gel, hexane/ethyl acetate=75/25) to obtain 0.413 g of the captioned compound (78% yield).

3rd Step

Synthesis of 5-tert-butyl-2-methoxy-3-(2,2,2-trifluoro-1-(methylamino)ethyl)aniline To a solution of 1-(5-tert-butyl-2-methoxy-3-nitrophenyl)-2,2,2-trifluoro-N-methylethaneamine (0.413 g, 1.29 mmol) in methanol (12.0 mL), 10% palladium/activated charcoal (0.041 g) was added and the resulting mixture was stirred at room temperature under hydrogen atmosphere for 3 hours. After completion of the reaction, the insoluble materials were filtered through a Celite pad, and the solvent was evaporated under reduced pressure. The obtained residue was purified by column chromatography (amine coated silica gel, hexane/ethyl acetate=90/10-0/100) to obtain 0.215 g of the captioned compound (57% yield).

4th Step

Synthesis of 2,2,2-trichloroethyl 1-(5-tert-butyl-3-(3-((1S,2R)-1-hydroxy-2,3-dihydro-1H-inden-2-yl)ureido)-2-methoxyphenyl)-2,2,2-trifluoroethyl(methyl)carbamate A solution of 5-tert-butyl-2-methoxy-3-(2,2,2-trifluoro-1-(methylamino)ethyl)aniline (0.215 g, 0.741 mmol) and N,N-diisopropylethylamine (0.350 mL, 1.95 mmol) in THF (3.5 mL) was cooled to 0° C., and 2,2,2-trichloroethyl chloroformate (0.220 mL, 1.65 mmol) was added thereto. The temperature was returned to room temperature and the mixture was stirred for 30 minutes. After completion of the reaction, methanol was added and the solvent was evaporated under reduced pressure. The obtained residue was purified by column chromatography (silica gel, hexane/ethyl acetate=50/50-90/10) to obtain 0.312 g of colorless solid. Using this colorless solid (0.312 g) and (1S,2R)-2-amino-2,3-dihydro-1H-inden-1-ol.L-tartaric acid salt (0.190 g, 0.633 mmol), the same reaction as in Example 3 (4th Step) was carried out to obtain 0.284 g of the captioned compound (60% yield in 2 steps).

5th Step

Synthesis of 1-(5-tert-butyl-2-methoxy-3-(2,2,2-trifluoro-1-(methylamino)ethyl)phenyl)-3-((1S,2R)-1-hydroxy-2,3-dihydro-1H-inden-2-yl)urea (Compound 48a, Compound 48b)

To a solution of 2,2,2-trichloroethyl 1-(5-tert-butyl-3-((1S,2R)-1-hydroxy-2,3-dihydro-1H-inden-2-yl)ureido)-2-methoxyphenyl)-2,2,2-trifluoroethyl(methyl)carbamate (0.284 g, 0.443 mmol) in acetic acid (2.2 mL), water (0.44 mL) and zinc (0.087 g, 1.33 mmol) was added, and the resulting mixture was stirred overnight at room temperature. After completion of the reaction, insoluble materials were filtered through a Celite pad. The filtrate was evaporated under reduced pressure. To the obtained residue, ethyl acetate and a solution of 1 mol/L sodium hydroxide was added, and the aqueous layer was extracted with ethyl acetate. The organic layer was washed with saturated brine, dried over anhydrous sodium sulfate and filtered, and the solvent was evaporated under reduced pressure. The obtained residue was purified by column chromatography (silica gel, hexane/ethyl acetate=90/10-0/100) to obtain 0.081 g of the captioned compound 48a (39% yield) in the low polarity side and 0.082 g of the captioned compound 48b (40% yield) in the high polarity side.

Example 6

Synthesis of 1-(5-tert-butyl-2-methoxy-3-(2,2,2-trifluoro-1-hydroxyethyl)phenyl)-3-((1S,2R)-1-hydroxy-4-methyl-2,3-dihydro-1H-inden-2-yl)urea (Compound 49a, Compound 49b)

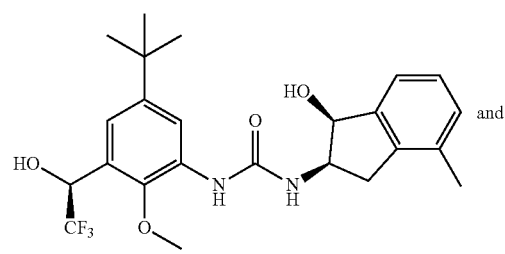
and

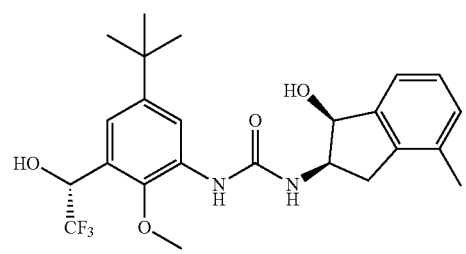

Using 2,2,2-trichloroethyl 5-tert-butyl-2-methoxy-3-(2,2,2-trifluoro-1-hydroxyethyl)phenylcarbamate (0.139 g, 0.308 mmol) and (1S,2R)-2-amino-4-methyl-2,3-dihydro-1H-inden-1-ol.(R)-mandelic acid salt (0.097 g, 0.308 mmol), the same reaction as in Example 3 (4th Step) was carried out to obtain 0.066 g of the captioned compound 49a (46% yield) in the low polarity side and 0.056 g of the captioned compound 49b (39% yield) in the high polarity side.

Example 7

Synthesis of 1-(5-tert-butyl-2-methoxy-3-((R)-2,2,2-trifluoro-1-hydroxyethyl)phenyl)-3-(cis-4-fluoro-1-hydroxy-2,3-dihydro-1H-inden-2-yl)urea (Compound 50a, Compound 50b)

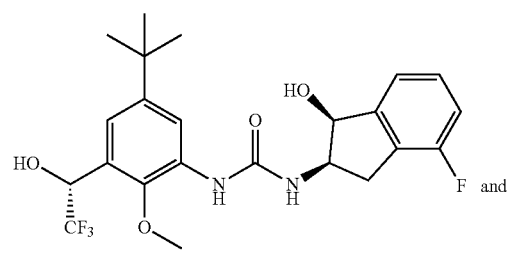
and

-continued

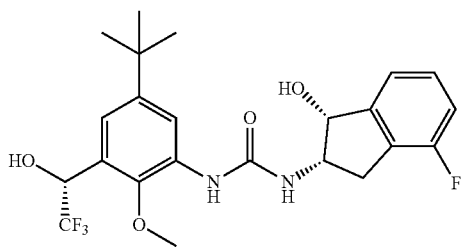

Using (R)-2,2,2-trichloroethyl 5-tert-butyl-2-methoxy-3-(2,2,2-trifluoro-1-hydroxyethyl)phenylcarbamate (0.203 g, 0.449 mmol) and (±)-cis-2-amino-4-fluoro-2,3-dihydro-1H-indene-1-ol (0.090 g, 0.538 mmol), the same reaction as in Example 3 (4th Step) was carried out to obtain 0.081 g of the captioned compound 50a (39% yield) in the low polarity side and 0.075 g of the captioned compound 50b (36% yield) in the high polarity side.

Example 8

Synthesis of 1-(5-tert-butyl-2-methoxy-3-(2,2,2-trifluoro-1-hydroxyethyl)phenyl)-3-(cis-4-chloro-1-hydroxy-2,3-dihydro-1H-indene-2-yl)urea (Compound 51a, Compound 51b)

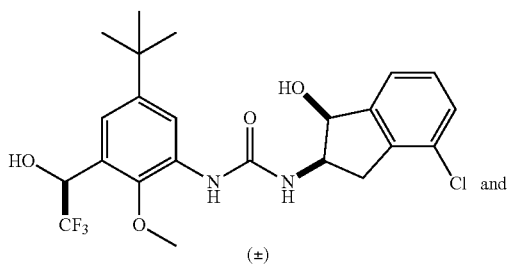

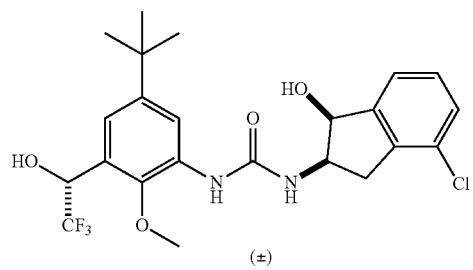

Using 2,2,2-trichloroethyl 5-tert-butyl-2-methoxy-3-(2,2,2-trifluoro-1-hydroxyethyl)phenylcarbamate (0.216 g, 0.477 mmol) and (±)-cis-2-amino-4-chloro-2,3-dihydro-1H-indene-1-ol (0.073 g, 0.398 mmol), the same reaction as in Example 3 (4th Step) was carried out to obtain 0.058 g of the captioned compound 51a (30% yield) in the low polarity side and 0.059 g of the captioned compound 51b (30% yield) in the high polarity side.

Example 9

Synthesis of 1-(5-tert-butyl-2-methoxy-3-(2,2,2-trifluoro-1-hydroxyethyl)phenyl)-3-((1S,2R)-1-hydroxy-4-methoxy-2,3-dihydro-1H-indene-2-yl)urea (Compound 52a, Compound 52b)

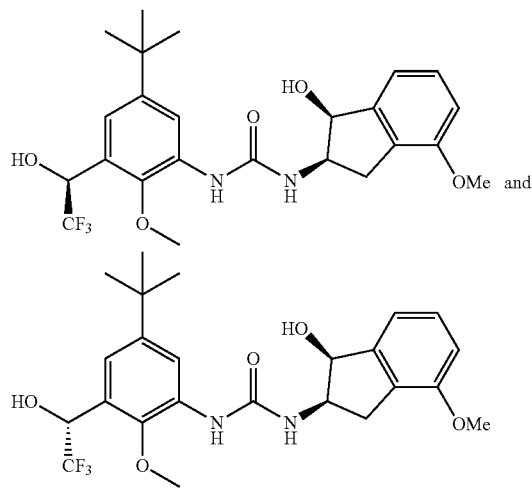

Using 2,2,2-trichloroethyl 5-tert-butyl-2-methoxy-3-(2,2,2-trifluoro-1-hydroxyethyl)phenylcarbamate (0.240 g, 0.530 mmol) and (1S,2R)-2-amino-4-methoxy-2,3-dihydro-1H-indene-1-ol (0.114 g, 0.636 mmol), the same reaction as in Example 3 (4th Step) was carried out to obtain 0.113 g of the captioned compound 52a (44% yield) in the low polarity side and 0.110 g of the captioned compound 52b (43% yield) in the high polarity side.

Example 10

Synthesis of 1-(5-tert-butyl-2-methoxy-3-((R)-2,2,2-trifluoro-1-hydroxyethyl)phenyl)-3-(cis-5-fluoro-1-hydroxy-2,3-dihydro-1H-indene-2-yl)urea (Compound 55a, Compound 55b)

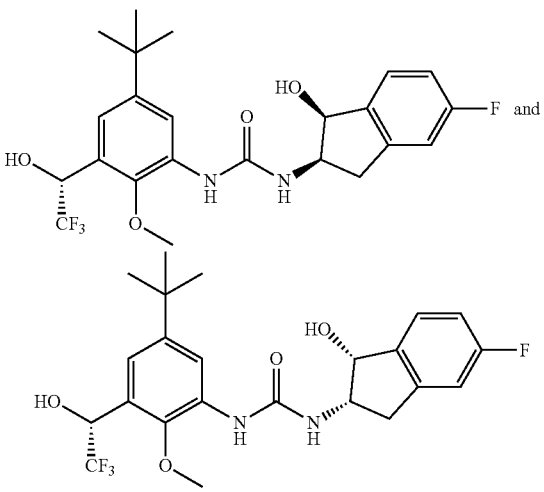

Using (R)-2,2,2-trichloroethyl 5-tert-butyl-2-methoxy-3-(2,2,2-trifluoro-1-hydroxyethyl)phenylcarbamate (0.241 g, 0.532 mmol) and (±)-cis-2-amino-5-fluoro-2,3-dihydro-1H-inden-1-ol (0.080 g, 0.479 mmol), the same reaction as in Example 3 (4th Step) was carried out to obtain 0.093 g of the captioned compound 55a (37% yield) in the low polarity side and 0.092 g of the captioned compound 55b (37% yield) in the high polarity side.

Example 11

Synthesis of 1-(5-tert-butyl-2-methoxy-3-((R)-2,2,2-trifluoro-1-hydroxyethyl)phenyl)-3-(cis-1-hydroxy-5-methoxy-2,3-dihydro-1H-inden-2-yl)urea (Compound 57a, Compound 57b)

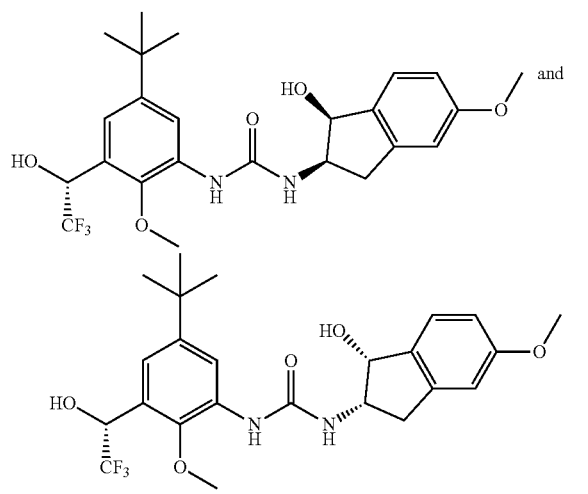

Using (R)-2,2,2-trichloroethyl 5-tert-butyl-2-methoxy-3-(2,2,2-trifluoro-1-hydroxyethyl)phenylcarbamate (0.174 g, 0.384 mmol) and (±)-cis-2-amino-5-methoxy-2,3-dihydro-1H-inden-1-ol (0.062 g, 0.346 mmol), the same reaction as in Example 3 (4th Step) was carried out to obtain 0.015 g of the captioned compound 57a (8% yield) in the low polarity side and 0.042 g captioned compound 57b (23% yield) in the high polarity side.

Example 12

Synthesis of 1-(5-tert-butyl-2-methoxy-3-((R)-2,2,2-trifluoro-1-hydroxyethyl)phenyl)-3-(cis-6-fluoro-1-hydroxy-2,3-dihydro-1H-inden-2-yl)urea (Compound 60a, Compound 60b)

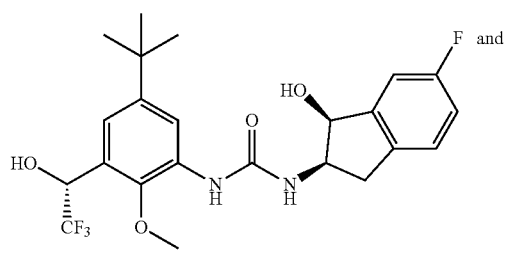

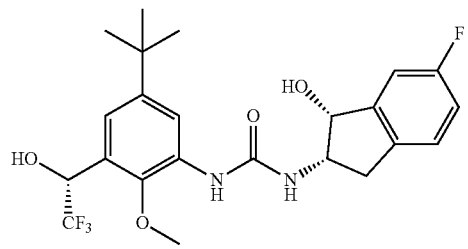

Using (R)-2,2,2-trichloroethyl 5-tert-butyl-2-methoxy-3-(2,2,2-trifluoro-1-hydroxyethyl)phenylcarbamate (0.241 g, 0.532 mmol) and (±)-cis-2-amino-6-fluoro-2,3-dihydro-1H-inden-1-ol (0.080 g, 0.479 mmol), the same reaction as in Example 3 (4th Step) was carried out to obtain 0.040 g of the captioned compound 60a (16% yield) in the low polarity side and 0.043 g of the captioned compound 60b (17% yield) in the high polarity side.

Example 13

Synthesis of 1-(5-tert-butyl-2-methoxy-3-((R)-2,2,2-trifluoro-1-hydroxyethyl)phenyl)-3-(cis-1-hydroxy-6-methoxy-2,3-dihydro-1H-inden-2-yl)urea (Compound 62a, Compound 62b)

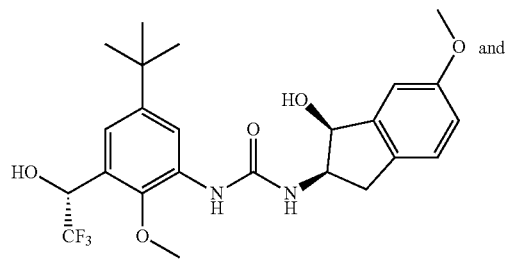

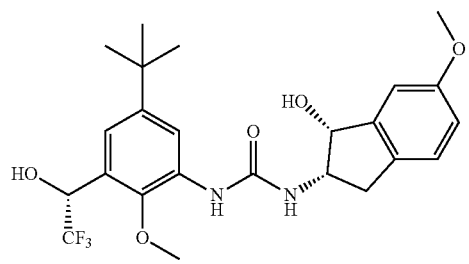

Using (R)-2,2,2-trichloroethyl 5-tert-butyl-2-methoxy-3-(2,2,2-trifluoro-1-hydroxyethyl)phenylcarbamate (0.421 g, 0.930 mmol) and (±)-cis-2-amino-6-methoxy-2,3-dihydro-1H-inden-1-ol (0.200 g, 1.12 mmol), the same reaction as in Example 3 (4th Step) was carried out to obtain 0.121 g of the captioned compound 62a (27% yield) in the low polarity side and 0.211 g of the captioned compound 62b (47% yield) in the high polarity side.

Example 14

Synthesis of 1-(5-tert-butyl-2-methoxy-3-((R)-2,2,2-trifluoro-1-hydroxyethyl)phenyl)-3-(cis-7-fluoro-1-hydroxy-2,3-dihydro-1H-inden-2-yl)urea (Compound 65a, Compound 65b)

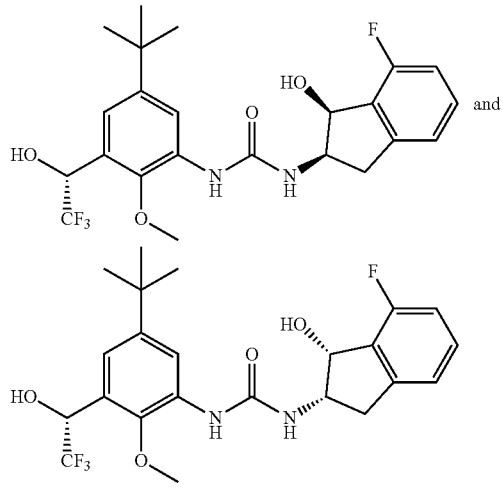

Using (R)-2,2,2-trichloroethyl 5-tert-butyl-2-methoxy-3-(2,2,2-trifluoro-1-hydroxyethyl)phenylcarbamate (0.220 g, 0.485 mmol) and (±)-cis-2-amino-7-fluoro-2,3-dihydro-1H-indene-1-ol (0.073 g, 0.437 mmol), the same reaction as in Example 3 (4th Step) was carried out to obtain 0.010 g of the captioned compound 65a (4% yield) in the low polarity side and 0.019 g of the captioned compound 65b (8% yield) in the high polarity side.

Example 15

Synthesis of 1-(5-tert-butyl-2-methoxy-3-((R)-2,2,2-trifluoro-1-hydroxyethyl)phenyl)-3-(cis-1-hydroxy-7-methoxy-2,3-dihydro-1H-inden-2-yl)urea (Compound 67a, Compound 67b)

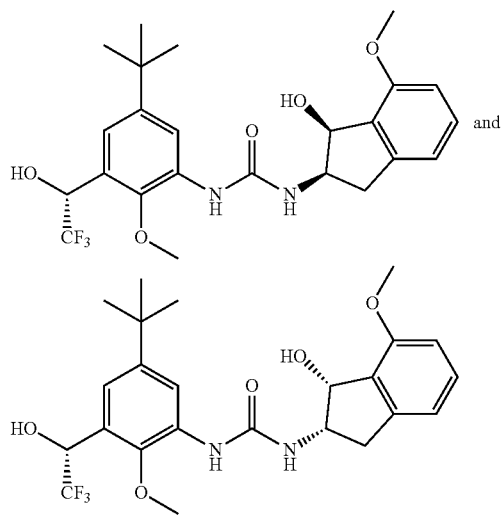

Using (R)-2,2,2-trichloroethyl 5-tert-butyl-2-methoxy-3-(2,2,2-trifluoro-1-hydroxyethyl)phenylcarbamate (0.250 g, 0.552 mmol) and (±)-cis-2-amino-7-methoxy-2,3-dihydro-1H-indene-1-ol (0.129 g, 0.720 mmol), the same reaction as in Example 3 (4th Step) was carried out to obtain 0.086 g of the captioned compound 67a (32% yield) in the low polarity side and 0.085 g of the captioned compound 67b (32% yield) in the high polarity side.

Example 16

Synthesis of 1-(5-tert-butyl-2-methoxy-3-((R)-2,2,2-trifluoro-1-hydroxyethyl)phenyl)-3-(cis-1,7-dihydroxy-2,3-dihydro-1H-inden-2-yl)urea (Compound 68a, Compound 68b)

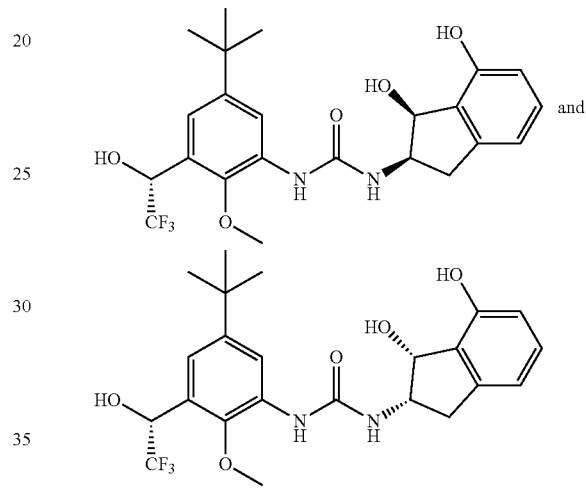

Using (R)-2,2,2-trichloroethyl 5-tert-butyl-2-methoxy-3-(2,2,2-trifluoro-1-hydroxyethyl)phenylcarbamate (0.136 g, 0.300 mmol) and (±)-cis-2-amino-2,3-dihydro-1H-indene-1,7-diol (0.052 g, 0.315 mmol), the same reaction as in Example 3 (4th Step) was carried out to obtain 0.033 g of the captioned compound 68a (23% yield) in the low polarity side and 0.026 g of the captioned compound 68b (19% yield) in the high polarity side.

Example 17

Synthesis of 1-(5-tert-butyl-2-methoxy-3-((R)-2,2,2-trifluoro-1-hydroxyethyl)phenyl)-3-(cis-4,7-difluoro-1-hydroxy-2,3-dihydro-1H-inden-2-yl)urea (Compound 73a, Compound 73b)

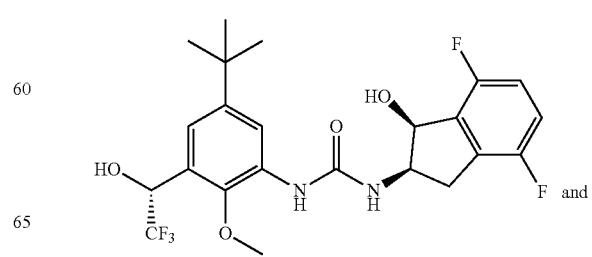

45

-continued

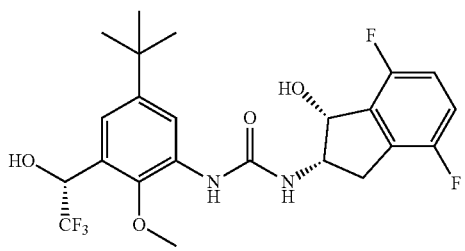

Using (R)-2,2,2-trichloroethyl 5-tert-butyl-2-methoxy-3-(2,2,2-trifluoro-1-hydroxyethyl)phenylcarbamate (0.200 g, 0.442 mmol) and (±)-cis-2-amino-4,7-difluoro-2,3-dihydro-1H-indene-1-ol (0.090 g, 0.486 mmol), the same reaction as in Example 3 (4th Step) was carried out to obtain 0.063 g of the captioned compound 73a (30% yield) in the low polarity side and 0.093 g of the captioned compound 73b (43% yield) in the high polarity side.

Example 18

Synthesis of 1-(5-tert-butyl-2-methoxy-3-((R)-2,2,2-trifluoro-1-hydroxyethyl)phenyl)-3-(cis-1-methoxy-2,3-dihydro-1H-indene-2-yl)urea (Compound 79a, Compound 79b)

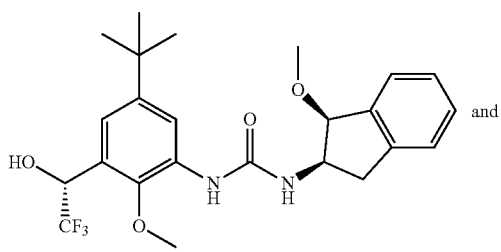

and

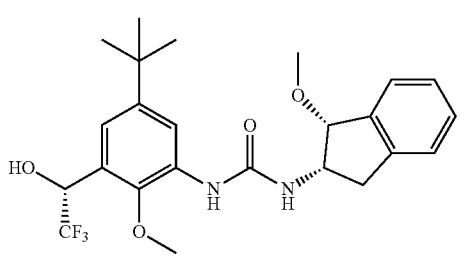

Using (R)-2,2,2-trichloroethyl 5-tert-butyl-2-methoxy-3-(2,2,2-trifluoro-1-hydroxyethyl)phenylcarbamate (0.200 g, 0.442 mmol) and (±)-cis-1-methoxy-2,3-dihydro-1H-indene-2-amine (0.094 g, 0.576 mmol), the same reaction as in Example 3 (4th Step) was carried out to obtain 0.087 g of the captioned compound 79a (42% yield) in the low polarity side and 0.088 g of the captioned compound 79b (43% yield) in the high polarity side.

46

Example 19

Synthesis of 1-(5-bromo-2-methoxy-3-(2,2,2-trifluoro-1-hydroxyethyl)phenyl)-3-((1S,2R)-1-hydroxy-2,3-dihydro-1H-indene-2-yl)urea (Compound 82a, Compound 82b)

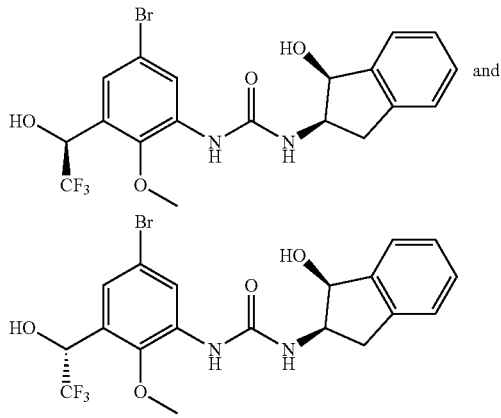

1st Step

Synthesis of 5-bromo-2-methoxy-3-nitrobenzaldehyde

A solution of 5-bromo-2-methoxybenzaldehyde (20.0 g, 93.0 mmol) in sulfuric acid (49.6 mL) was cooled to −15° C., and 60% nitric acid (7.62 mL, 102 mmol) was added thereto, followed by stirring the mixture for 2 hours. To the reaction solution, water was added, and the precipitated solids were collected to obtain to obtain 24.0 g (99% yield) of the captioned compound.

2nd Step

Synthesis of 1-(5-bromo-2-methoxy-3-nitrophenyl)-2,2,2-trifluoroethanol

Using 5-bromo-2-methoxy-3-nitrobenzaldehyde (12.0 g, 46.1 mmol), the same reaction as in Example 3 (1st Step) was carried out to obtain 9.32 g (61% yield) of the captioned compound.

3rd Step

Synthesis of 1-(3-amino-5-bromo-2-methoxyphenyl)-2,2,2-trifluoroethanol

Using 1-(5-bromo-2-methoxy-3-nitrophenyl)-2,2,2-trifluoroethanol (9.32 g, 28.2 mmol), the same reaction as in Example 3 (2nd Step) was carried out to obtain 7.62 g (90% yield) of the captioned compound.

4th Step

Synthesis of 2,2,2-trichloroethyl 5-bromo-2-methoxy-3-(2,2,2-trifluoro-1-hydroxyethyl)phenylcarbamate Using 1-(3-amino-5-bromo-2-methoxyphenyl)-2,2,2-trifluoroethanol (1.78 g, 5.93 mmol), the same reaction as in Example 3 (3rd Step) was carried out to obtain 2.27 g (80% yield) of the captioned compound.

5th Step

Synthesis of 1-(5-bromo-2-methoxy-3-(2,2,2-trifluoro-1-hydroxyethyl)phenyl)-3-((1S,2R)-1-hydroxy-2,3-dihydro-1H-inden-2-yl)urea (Compound 82a, Compound 82b)

Using 2,2,2-trichloroethyl 5-bromo-2-methoxy-3-(2,2,2-trifluoro-1-hydroxyethyl)phenylcarbamate (1.70 g, 3.58 mmol) and (1S,2R)-2-amino-2,3-dihydro-1H-indene-1-ol.L-tartaric acid salt (1.12 g, 3.75 mmol), the same reaction as in Example 3 (4th Step) was carried out to obtain 0.648 g of the captioned compound 82a (38% yield) in the low polarity side and 0.612 g of the captioned compound 82b (36% yield) in the high polarity side.

Example 20

Synthesis of 1-((1S,2R)-1-hydroxy-2,3-dihydro-1H-inden-2-yl)-3-(2-methoxy-5-morpholino-3-(2,2,2-trifluoro-1-hydroxyethyl)phenyl)urea (Compound 83a, Compound 83b)

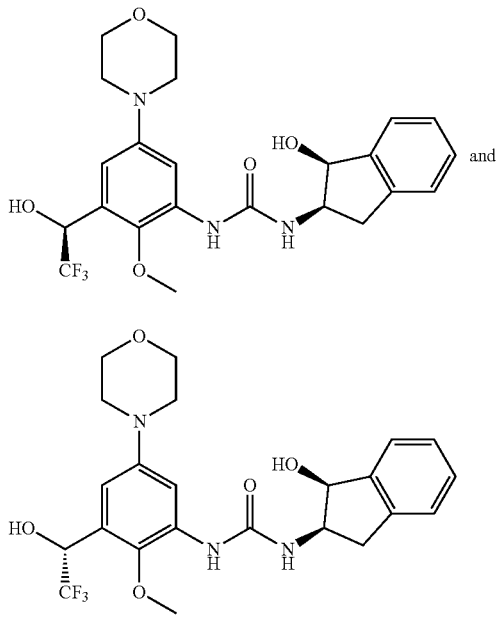

1st Step

Synthesis of 1-(3-amino-2-methoxy-5-morpholinophenyl)-2,2,2-trifluoroethanol To a solution of 1-(3-amino-5-bromo-2-methoxyphenyl)-2,2,2-trifluoroethanol (7.62 g, 25.4 mmol) in DMSO (25.4 mL), morpholine (11.1 mL, 127 mmol), L-proline (1.17 g, 10.1 mmol), potassium carbonate (14.0 g, 102 mmol) and copper iodide (0.967 g, 5.08 mmol) was added, and the mixture was stirred at 110° C. for 17 hours. The temperature of the reaction solution was returned to room temperature. After stopping the reaction by adding saturated aqueous ammonium chloride solution, aqueous layer was extracted with diethyl ether. The organic layer was washed with saturated brine, dried over anhydrous sodium sulfate and filtered, and then the solvent was evaporated under reduced pressure. The obtained residue was purified by column chromatography (silica gel, hexane/ethyl acetate=60/40-30/70) to obtain 5.32 g (68% yield) of the captioned compound.

2nd Step

Synthesis of 2,2,2-trichloroethyl 2-methoxy-5-morpholino-3-(2,2,2-trifluoro-1-hydroxyethyl)phenylcarbamate To a solution of 1-(3-amino-2-methoxy-5-morpholinophenyl)-2,2,2-trifluoroethanol (2.35 g, 7.67 mmol) in THF (20.4 mL), 2,2,2-trichloroethyl chloroformate (1.14 mL, 8.28 mmol), N,N-diisopropylethylamine (4.02 mL, 23.0 mmol) was added, and the mixture was stirred at 0° C. for 15 minutes. Water was added to the reaction solution and the aqueous layer was extracted with ethyl acetate. The organic layer was washed with saturated brine, dried over anhydrous sodium sulfate and filtered, and then the solvent was evaporated under reduced pressure. The obtained residue was purified by column chromatography (silica gel, hexane/ethyl acetate=80/20-60/40) to obtain 3.45 g (93% yield) of the captioned compound.

3rd Step

Synthesis of 1-((1S,2R)-1-hydroxy-2,3-dihydro-1H-inden-2-yl)-3-(2-methoxy-5-morpholino-3-(2,2,2-trifluoro-1-hydroxyethyl)phenyl)urea (Compound 83a, Compound 83b)

Using 2,2,2-trichloroethyl 2-methoxy-5-morpholino-3-(2,2,2-trifluoro-1-hydroxyethyl)phenylcarbamate (0.090 g, 0.187 mmol) and (1S,2R)-2-amino-2,3-dihydro-1H-indene-1-ol.L-tartaric acid salt (0.062 g, 0.206 mmol), the same reaction as in Example 3 (4th Step) was carried out to obtain 0.032 g of the captioned compound 83a (36% yield) in the low polarity side and 0.024 g of the captioned compound 83b (27% yield) in the high polarity side.

Example 21

Synthesis of 1-((1S,2R)-4-fluoro-1-hydroxy-2,3-dihydro-1H-inden-2-yl)-3-(2-methoxy-5-morpholino-3-(2,2,2-trifluoro-1-hydroxyethyl)phenyl)urea (Compound 84a, Compound 84b)

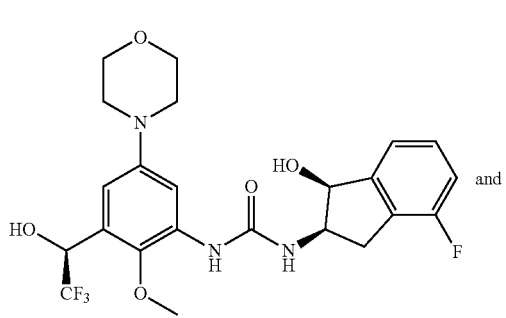

-continued

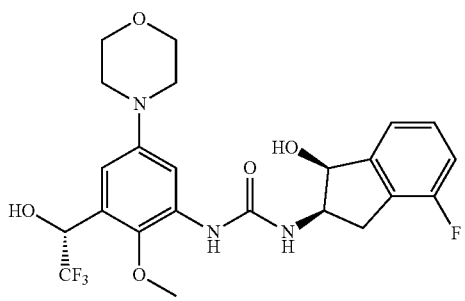

Using 2,2,2-trichloroethyl 2-methoxy-5-morpholino-3-(2,2,2-trifluoro-1-hydroxyethyl)phenylcarbamate (0.175 g, 0.364 mmol) and (1S,2R)-2-amino-4-fluoro-2,3-dihydro-1H-indene-1-ol.L-tartaric acid salt (0.127 g, 0.400 mmol), the same reaction as in Example 3 (4th Step) was carried out to obtain 0.080 g of the captioned compound 84a (44% yield) in the low polarity side and 0.075 g of the captioned compound 84b (41% yield) in the high polarity side.

Example 22

Synthesis of 1-((1S,2R)-1-hydroxy-2,3-dihydro-1H-indene-2-yl)-3-(2-methoxy-5-(pyrrolidine-1-yl)-3-(2,2,2-trifluoro-1-hydroxyethyl)phenyl)urea (Compound 92a, Compound 92b)

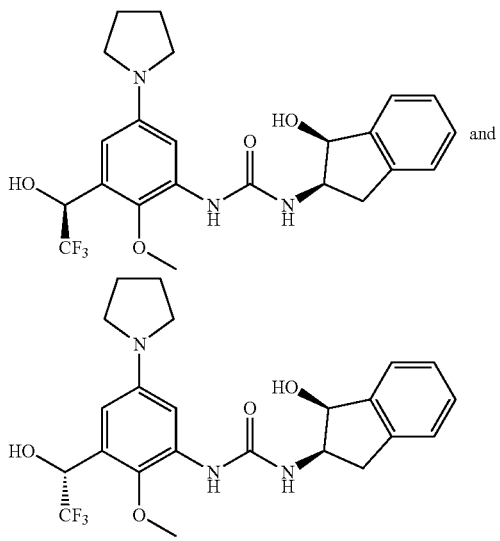

1st Step

Synthesis of 1-(3-amino-2-methoxy-5-(pyrrolidine-1-yl)phenyl)-2,2,2-trifluoroethanol Using 1-(3-amino-5-bromo-2-methoxyphenyl)-2,2,2-trifluoroethanol (0.600 g, 2.00 mmol) and pyrrolidine (0.25 mL, 3.04 mmol), the same reaction as in Example 20 (1st Step) was carried out to obtain 0.253 g of the captioned compound (44% yield).

2nd Step

Synthesis of 2,2,2-trichloroethyl 2-methoxy-5-(pyrrolidine-1-yl)-3-(2,2,2-trifluoro-1-hydroxyethyl)phenylcarbamate Using 1-(3-amino-2-methoxy-5-(pyrrolidine-1-yl)phenyl)-2,2,2-trifluoroethanol (0.253 g, 0.872 mmol), the same reaction as in Example 3 (3rd Step) was carried out to obtain 0.406 g of the captioned compound (99% yield).

3rd Step

Synthesis of 1-((1S,2R)-1-hydroxy-2,3-dihydro-1H-indene-2-yl)-3-(2-methoxy-5-(pyrrolidine-1-yl)-3-(2,2,2-trifluoro-1-hydroxyethyl)phenyl)urea (Compound 92a, Compound 92b)

Using 2,2,2-trichloroethyl 2-methoxy-5-(pyrrolidine-1-yl)-3-(2,2,2-trifluoro-1-hydroxyethyl)phenylcarbamate (0.233 g, 0.500 mmol) and (1S,2R)-2-amino-2,3-dihydro-1H-indene-1-ol.L-tartaric acid salt (0.165 g, 0.551 mmol), the same reaction as in Example 3 (4th Step) was carried out to obtain 0.058 g of the captioned compound 92a (25% yield) in the low polarity side and 0.068 g of the captioned compound 92b (29% yield) in the high polarity side.

Example 23

Synthesis of 1-((1S,2R)-4-fluoro-1-hydroxy-2,3-dihydro-1H-indene-2-yl)-3-(2-methoxy-5-(pyrrolidine-1-yl)-3-(2,2,2-trifluoro-1-hydroxyethyl)phenyl)urea (Compound 93a, Compound 93b)

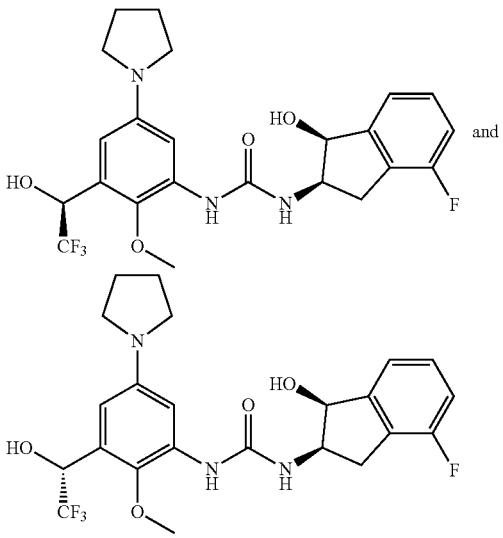

Using 2,2,2-trichloroethyl 2-methoxy-5-(pyrrolidine-1-yl)-3-(2,2,2-trifluoro-1-hydroxyethyl)phenylcarbamate (0.169 g, 0.364 mmol) and (1S,2R)-2-amino-4-fluoro-2,3-dihydro-1H-indene-1-ol.L-tartaric acid salt (0.127 g, 0.400 mmol), the same reaction as in Example 3 (4th Step) was carried out to obtain 0.045 g of the captioned compound 93a (26% yield) in the low polarity side and 0.047 g of the captioned compound 93b (27% yield) in the high polarity side.

Example 24

Synthesis of 1-((1S,2R)-1-hydroxy-2,3-dihydro-1H-indene-2-yl)-3-(2-methoxy-5-(piperidine-1-yl)-3-(2,2,2-trifluoro-1-hydroxyethyl)phenyl)urea (Compound 97a, Compound 97b)

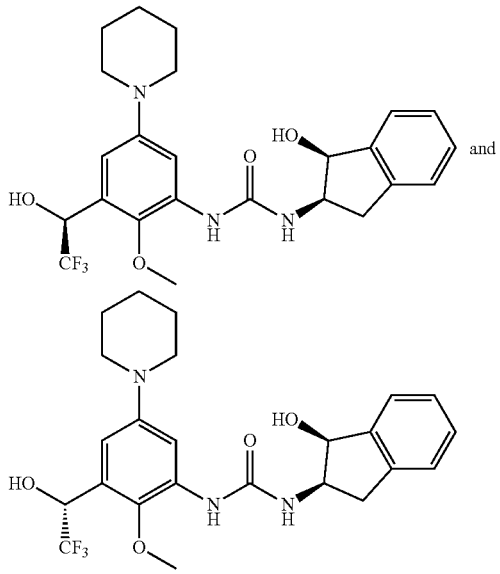

1st Step

Synthesis of 1-(3-amino-2-methoxy-5-(piperidine-1-yl)phenyl)-2,2,2-trifluoroethanol Using 1-(3-amino-5-bromo-2-methoxyphenyl)-2,2,2-trifluoroethanol (0.300 g, 1.00 mmol) and piperidine (0.150 mL, 1.52 mmol), the same reaction as in Example 20 (1st Step) was carried out to obtain 0.091 g of the captioned compound (30% yield).

2nd Step

Synthesis of 2,2,2-trichloroethyl 2-methoxy-5-(piperidine-1-yl)-3-(2,2,2-trifluoro-1-hydroxyethyl)phenylcarbamate Using 1-(3-amino-2-methoxy-5-(piperidine-1-yl)phenyl)-2,2,2-trifluoroethanol (0.080 g, 0.263 mmol), the same reaction as in Example 3 (3rd Step) was carried out to obtain 0.126 g of the captioned compound (99% yield).

3rd Step

Synthesis of 1-((1S,2R)-1-hydroxy-2,3-dihydro-1H-indene-2-yl)-3-(2-methoxy-5-(piperidine-1-yl)-3-(2,2,2-trifluoro-1-hydroxyethyl)phenyl)urea (Compound 97a, Compound 97b)

Using 2,2,2-trichloroethyl 2-methoxy-5-(piperidine-1-yl)-3-(2,2,2-trifluoro-1-hydroxyethyl)phenylcarbamate (0.125 g, 0.261 mmol) and (1S,2R)-2-amino-2,3-dihydro-1H-indene-1-ol.L-tartaric acid salt (0.086 g, 0.287 mmol), the same reaction as in Example 3 (4th Step) was carried out to obtain 0.032 g of the captioned compound 97a (26% yield) in the low polarity side and 0.034 g of the captioned compound 97b (27% yield) in the high polarity side.

Example 25

Synthesis of 1-(5-(azepan-1-yl)-2-methoxy-3-(2,2,2-trifluoro-1-hydroxyethyl)phenyl)-3-((1S,2R)-1-hydroxy-2,3-dihydro-1H-indene-2-yl)urea (Compound 102a, Compound 102b)

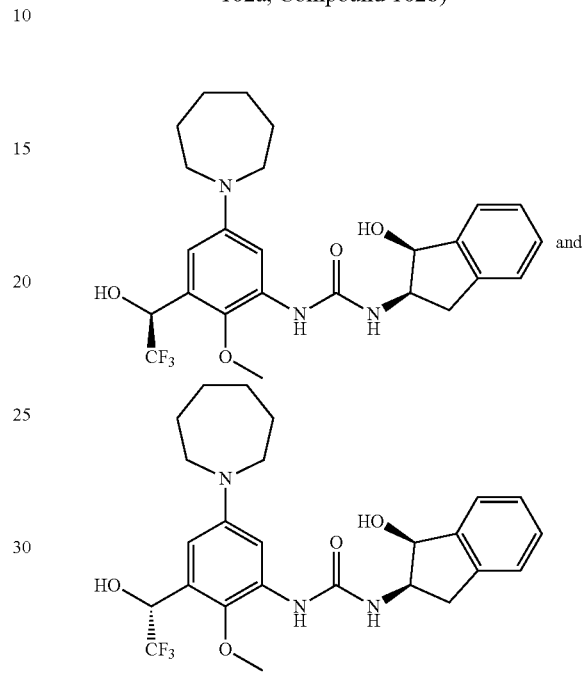

1st Step

Synthesis of 1-(3-amino-5-(azepan-1-yl)-2-methoxyphenyl)-2,2,2-trifluoroethanol

Using 1-(3-amino-5-bromo-2-methoxyphenyl)-2,2,2-trifluoroethanol (0.600 g, 2.00 mmol) and hexamethyleneimine (0.298 g, 3.00 mmol), the same reaction as in Example 20 (1st Step) was carried out to obtain 0.435 g of the captioned compound (68% yield).

2nd Step

Synthesis of 2,2,2-trichloroethyl 5-(azepan-1-yl)-2-methoxy-3-(2,2,2-trifluoro-1-hydroxyethyl)phenylcarbamate Using 1-(3-amino-5-(azepan-1-yl)-2-methoxyphenyl)-2,2,2-trifluoroethanol (0.404 g, 1.27 mmol), the same reaction as in Example 1 (4th Step) was carried out to obtain 0.408 g of the captioned compound (65% yield).

3rd Step

Synthesis of 1-(5-(azepan-1-yl)-2-methoxy-3-(2,2,2-trifluoro-1-hydroxyethyl)phenyl)-3-((1S,2R)-1-hydroxy-2,3-dihydro-1H-indene-2-yl)urea (Compound 102a, Compound 102b)

Using 2,2,2-trichloroethyl 5-(azepan-1-yl)-2-methoxy-3-(2,2,2-trifluoro-1-hydroxyethyl)phenylcarbamate (0.173 g, 0.350 mmol) and (1S,2R)-2-amino-2,3-dihydro-1H-indene-1-ol.L-tartaric acid salt (0.115 g, 0.385 mmol), the same reaction as in Example 3 (4th Step) was carried out to obtain 0.045 g of the captioned compound 102a (26% yield) in the low polarity side and 0.050 g of the captioned compound 102b (29% yield) in the high polarity side.

Example 26

Synthesis of 1-((1S,2R)-1-hydroxy-2,3-dihydro-1H-indene-2-yl)-3-(2-methoxy-5-(4-methyltetrahydro-2H-pyran-4-yl)-3-(2,2,2-trifluoro-1-hydroxyethyl)phenyl)urea (Compound 108a, Compound 108b)

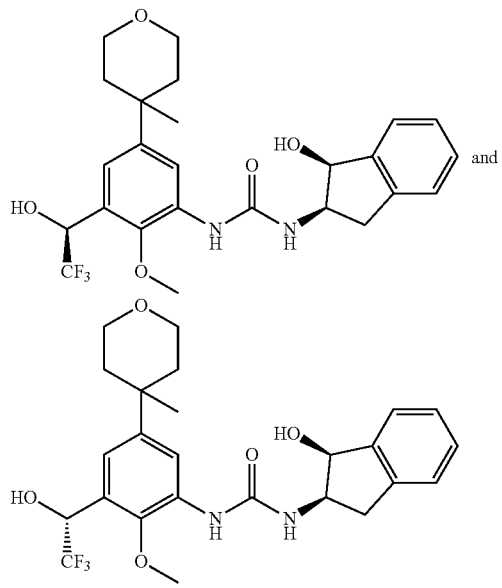

1st Step

Synthesis of 4-(4-methoxyphenyl)tetrahydro-2H-pyran-4-ol

A solution of 4-bromoanisole (1.00 g, 5.35 mmol) in THF (10.0 mL) was cooled to −78° C., and 2.77 mol/L n-butyllithium solution in n-hexane (2.31 mL, 6.42 mmol) was added dropwise thereto. After stirring the mixture for 1 hours, tetrahydro-4H-pyran-4-one (0.595 mL, 6.42 mmol) was added dropwise thereto. After stirring the mixture for 2 hours, acetic acid was added to the reaction solution to stop the reaction. The temperature was returned to room temperature, and the mixture was diluted with ethyl acetate and the organic layer was washed with water. The organic layer was washed with saturated brine, dried over anhydrous sodium sulfate and filtered. The solvent was evaporated under reduced pressure, and the obtained residue was purified by column chromatography (silica gel, hexane/ethyl acetate=20/80-0/100) to obtain 0.680 g of the captioned compound (61% yield).

2nd Step

Synthesis of 4-(4-methoxyphenyl)-4-methyltetrahydro-2H-pyran

A solution of 4-(4-methoxyphenyl)tetrahydro-2H-pyran-4-ol (0.680 g, 3.27 mmol) in dichloromethane (16.0 mL) was cooled to −78° C., and titanium tetrachloride (0.720 mL, 6.53 mmol) was added dropwise thereto. After stirring the mixture for 1 hour, 1.0 mol/L dimethylzinc solution in n-hexane (13.1 mL, 13.1 mmol) was added dropwise thereto. The mixture was stirred for 2 hours, and water was added to stop the reaction. The temperature was returned to room temperature, and the mixture was diluted with ethyl acetate and 1 mol/L hydrochloric acid. The organic layer was washed with water and then with saturated brine, dried over anhydrous sodium sulfate and filtered. The solvent was then evaporated under reduced pressure, and the obtained residue was purified by column chromatography (silica gel, hexane/ethyl acetate=90/10-30/70) to obtain 0.641 g of the captioned compound (95% yield).

3rd Step

Synthesis of 2-methoxy-5-(4-methyltetrahydro-2H-pyran-4-yl)benzaldehyde

A solution of 4-(4-methoxyphenyl)-4-methyltetrahydro-2H-pyran (0.518 g, 2.51 mmol) in dichloromethane (12.0 mL) was cooled to −15° C., and titanium tetrachloride (1.22 mL, 11.0 mmol) was added dropwise thereto. After stirring the mixture for 20 minutes, dichloromethyl methyl ether (0.336 mL, 3.77 mmol) was added dropwise thereto. After stirring the mixture for 1 hour, 1 mol/L hydrochloric acid was added to stop the reaction. The reaction solution was diluted with ethyl acetate, and the organic layer was washed with water and then with saturated brine, dried over anhydrous sodium sulfate and filtered. The solvent was then evaporated under reduced pressure to obtain 0.719 g of the crude product containing the captioned compound.

4th Step

Synthesis of 2-methoxy-5-(4-methyltetrahydro-2H-pyran-4-yl)-3-nitrobenzaldehyde

A solution of the crude product containing 2-methoxy-5-(4-methyltetrahydro-2H-pyran-4-yl)benzaldehyde (0.719 g) in ethyl acetate (10.0 mL) was cooled to −40° C., and nitronium tetrafluoroborate (0.597 g, 4.49 mmol) was added thereto. The resulting mixture was stirred for 2 hours while raising the temperature to −10° C. Water was added to the reaction solution and the resulting solution was diluted with ethyl acetate. The organic layer was washed with water, saturated aqueous sodium hydrogen carbonate solution and saturated brine, dried over anhydrous sodium sulfate and filtered. The solvent was then evaporated under reduced pressure, and the obtained residue was purified by column chromatography (silica gel, hexane/ethyl acetate=90/10-30/70) to obtain 0.644 g of the captioned compound (92% yield in 2 steps).

5th Step

Synthesis of 2,2,2-trifluoro-1-(2-methoxy-5-(4-methyltetrahydro-2H-pyran-4-yl)-3-nitrophenyl)ethanol Using 2-methoxy-5-(4-methyltetrahydro-2H-pyran-4-yl)-3-nitrobenzaldehyde (0.644 g, 2.30 mmol), the same reaction as in Example 3 (1st Step) was carried out to obtain 0.697 g (87% yield) of the captioned compound.

6th Step

Synthesis of 1-(3-amino-2-methoxy-5-(4-methyltetrahydro-2H-pyran-4-yl)phenyl)-2,2,2-trifluoroethanol Using 2,2,2-trifluoro-1-(2-methoxy-5-(4-methyltetrahydro-2H-pyran-4-yl)-3-nitrophenyl)ethanol (0.697 g, 1.99 mmol), the same reaction as in Example 3 (2nd Step) was carried out to obtain 0.698 g of the crude product containing the captioned compound.

7th Step

Synthesis of 2,2,2-trichloroethyl 2-methoxy-5-(4-methyltetrahydro-2H-pyran-4-yl)-3-(2,2,2-trifluoro-1-hydroxyethyl)phenylcarbamate Using the crude product containing 1-(3-amino-2-methoxy-5-(4-methyltetrahydro-2H-pyran-4-yl)phenyl)-2,2,2-trifluoroethanol (0.698 g), the same reaction as in Example 1 (4th Step) was carried out to obtain 0.708 g (72% yield in 2 steps) of the captioned compound.

8th Step

Synthesis of 1-((1S,2R)-1-hydroxy-2,3-dihydro-1H-inden-2-yl)-3-(2-methoxy-5-(4-methyltetrahydro-2H-pyran-4-yl)-3-(2,2,2-trifluoro-1-hydroxyethyl)phenyl)urea (Compound 108a, Compound 108b)

Using 2,2,2-trichloroethyl 2-methoxy-5-(4-methyltetrahydro-1H-pyran-4-yl)-3-(2,2,2-trifluoro-1-hydroxyethyl)phenylcarbamate (0.150 g, 0.303 mmol) and (1S,2R)-2-amino-2,3-dihydro-1H-inden-1-ol.L-tartaric acid salt (0.118 g, 0.394 mmol), the same reaction as in Example 3 (4th Step) was carried out to obtain 0.059 g of the captioned compound 108a (40% yield) in the low polarity side and 0.066 g of the captioned compound 108b (44% yield) in the high polarity side.

Example 27

Synthesis of 1-((1S,2R)-1-hydroxy-2,3-dihydro-1H-inden-2-yl)-3-(2-methoxy-5-tert-pentyl-3-(2,2,2-trifluoro-1-hydroxyethyl)phenyl)urea (Compound 123a, Compound 123b)

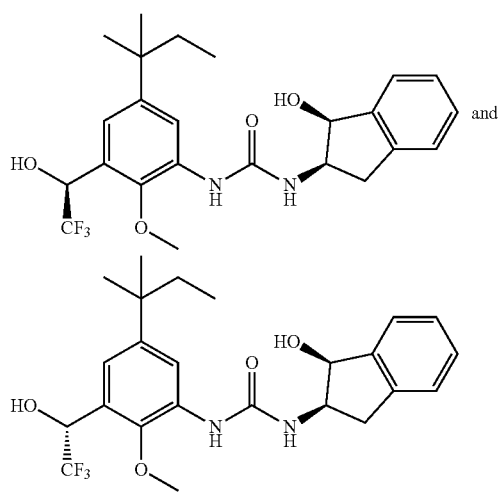

1st Step

Synthesis of 2,2,2-trifluoro-1-(2-methoxy-3-nitro-5-tert-pentylphenyl)ethanol

Using 2-methoxy-3-nitro-5-tert-pentylbenzaldehyde (0.351 g, 1.40 mmol), the same reaction as in Example 3 (1st Step) was carried out to obtain 0.337 g of the captioned compound (75% yield).

2nd Step

Synthesis of 1-(3-amino-2-methoxy-5-tert-pentylphenyl)-2,2,2-trifluoroethanol

Using 2,2,2-trifluoro-1-(2-methoxy-3-nitro-5-tert-pentylphenyl)ethanol (0.334 g, 1.04 mmol), the same reaction as in Example 3 (2nd Step) was carried out to obtain 0.303 g of the crude product containing the captioned compound.

3rd Step

Synthesis of 2,2,2-trichloroethyl 2-methoxy-5-tert-pentyl-3-(2,2,2-trifluoro-1-hydroxyethyl)phenylcarbamate Using the crude product containing 1-(3-amino-2-methoxy-5-tert-pentylphenyl)-2,2,2-trifluoroethanol, the same reaction as in Example 3 (3rd Step) was carried out to obtain 0.208 g of the captioned compound (43% yield in 2 steps).

4th Step

Synthesis of 1-((1S,2R)-1-hydroxy-2,3-dihydro-1H-inden-2-yl)-3-(2-methoxy-5-tert-pentyl-3-(2,2,2-trifluoro-1-hydroxyethyl)phenyl)urea (Compound 123a, Compound 123b)

Using 2,2,2-trichloroethyl 2-methoxy-5-tert-pentyl-3-(2,2,2-trifluoro-1-hydroxyethyl)phenylcarbamate (0.200 g, 0.428 mmol) and (1S,2R)-2-amino-2,3-dihydro-1H-inden-1-ol.L-tartaric acid salt (0.128 g, 0.428 mmol), the same reaction as in Example 3 (4th Step) was carried out to obtain 0.073 g of the captioned compound 123a (36% yield) in the low polarity side and 0.078 g of the captioned compound 123b (39% yield) in the high polarity side.

Example 28

Synthesis of 1-((1S,2R)-1-hydroxy-2,3-dihydro-1H-inden-2-yl)-3-(2-methoxy-5-(1-methylcyclobutyl)-3-(2,2,2-trifluoro-1-hydroxyethyl)phenyl)urea (Compound 135a, Compound 135b)

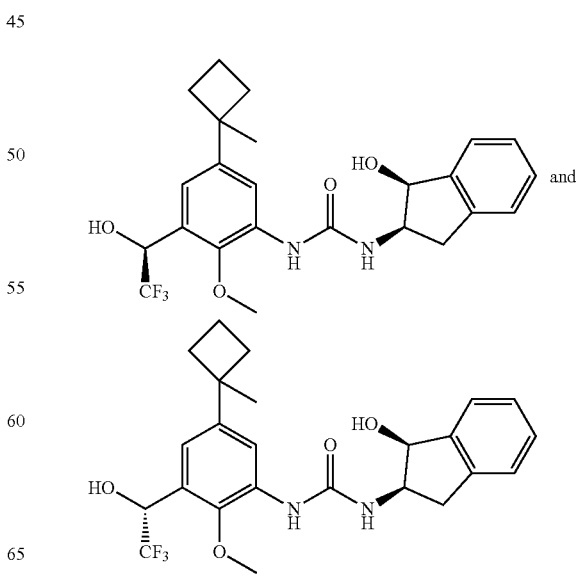

1st Step

Synthesis of 1-(4-methoxyphenyl)cyclobutanol

Using 4-bromoanisole (6.67 g, 35.7 mmol) and cyclobutanone (3.00 g, 42.8 mmol), the same reaction as in Example 26 (1st Step) was carried out to obtain 6.06 g of the captioned compound (95% yield).

2nd Step

Synthesis of 1-methoxy-4-(1-methylcyclobutyl)benzene

Using 1-(4-methoxyphenyl)cyclobutanol (3.00 g, 16.8 mmol), the same reaction as in Example 26 (2nd Step) was carried out to obtain 2.52 g of the captioned compound (85% yield).

3rd Step

Synthesis of 2-methoxy-5-(1-methylcyclobutyl)benzaldehyde

Using 1-methoxy-4-(1-methylcyclobutyl)benzene (1.20 g, 6.81 mmol), the same reaction as in Example 26 (3rd Step) was carried out to obtain 1.39 g of the captioned compound (99% yield).

4th Step

Synthesis of 2-methoxy-5-(1-methylcyclobutyl)-3-nitrobenzaldehyde

Using 2-methoxy-5-(1-methylcyclobutyl)benzaldehyde (1.39 g, 6.80 mmol), the same reaction as in Example 26 (4th Step) was carried out to obtain 1.07 g of the captioned compound (63% yield).

5th Step

Synthesis of 2,2,2-trifluoro-1-(2-methoxy-5-(1-methylcyclobutyl)-3-nitrophenyl)ethanol Using 2-methoxy-5-(1-methylcyclobutyl)-3-nitrobenzaldehyde (1.06 g, 4.25 mmol), the same reaction as in Example 3 (1st Step) was carried out to obtain 1.17 g of the captioned compound (86% yield).

6th Step

Synthesis of 1-(3-amino-2-methoxy-5-(1-methylcyclobutyl)phenyl)-2,2,2-trifluoroethanol Using 2,2,2-trifluoro-1-(2-methoxy-5-(1-methylcyclobutyl)-3-nitrophenyl)ethanol (1.17 g, 3.66 mmol), the same reaction as in Example 3 (2nd Step) was carried out to obtain 0.955 g of the captioned compound (90% yield).

7th Step

Synthesis of 2,2,2-trichloroethyl 2-methoxy-5-(1-methylcyclobutyl)-3-(2,2,2-trifluoro-1-hydroxyethyl)phenylcarbamate Using 1-(3-amino-2-methoxy-5-(1-methylcyclobutyl)phenyl)-2,2,2-trifluoroethanol (0.950 g, 3.28 mmol), the same reaction as in Example 3 (3rd Step) was carried out to obtain 1.268 g of the captioned compound (83% yield).

8th Step

Synthesis of 1-((1S,2R)-1-hydroxy-2,3-dihydro-1H-inden-2-yl)-3-(2-methoxy-5-(1-methylcyclobutyl)-3-(2,2,2-trifluoro-1-hydroxyethyl)phenyl)urea (Compound 135a, Compound 135b)

Using 2,2,2-trichloroethyl 2-methoxy-5-(1-methylcyclobutyl)-3-(2,2,2-trifluoro-1-hydroxyethyl)phenylcarbamate (0.270 g, 0.581 mmol) and (1S,2R)-2-amino-2,3-dihydro-1H-inden-1-ol.L-tartaric acid salt (0.183 g, 0.611 mmol), the same reaction as in Example 3 (4th Step) was carried out to obtain 0.108 g of the captioned compound 135a (40% yield) in the low polarity side and 0.107 g of the captioned compound 135b (40% yield) in the high polarity side.

The physical property data of the Compound (I) synthesized as above are shown in Table 3 below.

TABLE 3

| Compound | NMR | MS |
|---|---|---|
| 1 | 400 MHz, CDCl$_3$<br>δ: 7.87 (1H, d, J = 2.2 Hz), 7.41 (1H, d, J = 6.4 Hz), 7.30-7.22 (3H, m), 7.06 (1H, d, J = 2.2 Hz), 6.89 (1H, brs), 5.67 (1H, d, J = 7.8 Hz), 5.11-5.08 (1H, m), 4.67 (2H, d, J = 6.1 Hz), 4.65-4.58 (1H, m), 3.76 (3H, s), 3.29 (1H, dd, J = 16.1, 7.2 Hz), 2.89 (1H, dd, J = 16.1, 6.6 Hz), 2.40 (1H, d, J = 5.1 Hz), 2.09 (1H, t, J = 6.1 Hz), 1.28 (9H, s). | ESI[M + H]$^+$<br>385 |
| 3 | 400 MHz, CDCl$_3$<br>δ: 7.84-6.95 (6H, m), 5.69 (1H, d, J = 7.8 Hz), 5.11 (1H, brs), 4.67-4.61 (3H, m), 3.77 (3H, s), 3.34 (1H, dd, J = 7.3, 16.3 Hz), 2.87 (1H, dd, J = 16.3, 6.3 Hz), 2.64 (1H, brs), 2.12 (1H, brs), 1.29 (9H, s). | ESI[M + H]$^+$<br>403 |
| 46a | 400 MHz, CDCl$_3$<br>δ: 7.89 (1H, d, J = 2.2 Hz), 7.40 (1H, d, J = 6.5 Hz), 7.27-7.22 (4H, m), 6.82 (1H, s), 5.71 (1H, d, J = 7.8 Hz), 5.33-5.26 (1H, m), 5.09 (1H, dd, J = 5.1, 5.1 Hz), 4.63-4.56 (1H, m), 3.76 (3H, s), 3.43 (1H, d, J = 6.3 Hz), 3.27 (1H, dd, J = 16.0, 7.3 Hz), 2.87 (1H, dd, J = 16.0, 6.7 Hz), 2.43 (1H, d, J = 5.1 Hz), 1.28 (9H, s). | ESI[M + H]$^+$<br>453 |
| 46b | 400 MHz, CDCl$_3$<br>δ: 7.89 (1H, d, J = 2.5 Hz), 7.40 (1H, d, J = 6.3 Hz), 7.28-7.21 (4H, m), 6.86 (1H, brs), 5.77 (1H, d, J = 7.8 Hz), 5.31-5.24 (1H, m), 5.08 (1H, dd, J = 4.9, 4.9 Hz), 4.62-4.55 (1H, m), 3.74 (3H, s), 3.45 (1H, d, J = 6.4 Hz), 3.28 (1H, dd, J = 16.0, 7.2 Hz), 2.88 (1H, dd, J = 16.0, 6.7 Hz), 2.45 (1H, d, J = 4.4 Hz), 1.27 (9H, s). | ESI[M + H]$^+$<br>453 |

TABLE 3-continued

| Compound | NMR | MS |
|---|---|---|
| 47a | 400 MHz, CDCl$_3$<br>δ: 7.90 (1H, d, J = 2.0 Hz), 7.42 (1H, d, J = 6.8 Hz), 7.32-7.20 (4H, m), 6.71 (1H, s), 5.63 (1H, d, J = 8.0 Hz), 5.35-5.27 (1H, m), 5.11 (1H, d, J = 5.6 Hz), 4.67-4.57 (1H, m), 3.79 (3H, s), 3.30 (1H, dd, J = 16.0, 7.2 Hz), 3.26-3.20 (2H, m), 2.90 (1H, dd, J = 6.4, 6.0 Hz), 2.26 (1H, brs), 1.29 (9H, s). | ESI[M + H]$^+$ 452 |
| 47b | 400 MHz, CDCl$_3$<br>δ: 7.91 (1H, d, J = 2.0 Hz), 7.43 (1H, d, J = 7.2 Hz), 7.31-7.20 (4H, m), 6.84 (1H, m), 5.72 (1H, d, J = 8.0 Hz), 5.30 (1H, q, J = 6.4 Hz), 5.12 (1H, d, J = 5.6 Hz), 4.66-4.58 (1H, m), 3.79 (3H, s), 3.32 (1H, dd, J = 16.0, 7.2 Hz), 2.90 (1H, dd, J = 16.0, 5.6 Hz), 1.29 (9H, s). | ESI[M + H]$^+$ 452 |
| 48a | 400 MHz, CDCl$_3$<br>δ: 7.92 (1H, d, J = 2.0 Hz), 7.43 (1H, d, J = 6.4 Hz), 7.33-7.22 (3H, m), 7.13 (1H, d, J = 2.0 Hz), 6.72 (1H, s), 5.59 (1H, d, J = 7.6 Hz), 5.12 (1H, d, J = 5.6 Hz), 4.70-4.60 (1H, m), 4.50-4.40 (1H, m), 3.76 (3H, s), 3.31 (1H, dd, J = 16.0, 6.6 Hz), 2.90 (1H, dd, J = 16.0, 6.8 Hz), 2.39 (3H, s), 1.29 (9H, s). | ESI[M + H]$^+$ 466 |
| 48b | 400 MHz, CDCl$_3$<br>δ: 7.94 (1H, d, J = 2.4 Hz), 7.42 (1H, d, J = 7.2 Hz), 7.33-7.23 (3H, m), 7.12 (1H, d, J = 2.4 Hz), 6.80 (1H, s), 5.65 (1H, d, J = 8.0 Hz), 5.11 (1H, d, J = 5.6 Hz), 4.67-4.58 (1H, m), 4.52-4.43 (1H, m), 3.75 (3H, s), 3.31 (1H, dd, J = 16.0, 7.6 Hz), 2.91 (1H, dd, J = 16.0, 6.4 Hz), 2.40 (3H, s), 1.29 (9H, s). | ESI[M + H]$^+$ 466 |
| 49a | 400 MHz, CDCl$_3$<br>δ: 7.91-6.83 (6H, m), 5.79 (1H, d, J = 7.8 Hz), 5.33-5.27 (1H, m), 5.07 (1H, d, J = 5.6 Hz), 4.62-4.55 (1H, m), 3.77 (3H, s), 3.42 (1H, d, J = 4.9 Hz), 3.27 (1H, dd, J = 16.1, 7.3 Hz), 2.77 (1H, dd, J = 16.1, 6.8 Hz), 2.23 (3H, s), 1.62 (1H, brs), 1.29 (9H, s). | ESI[M + H]$^+$ 467 |
| 49b | 400 MHz, CDCl$_3$<br>δ: 7.93-6.78 (6H, m), 5.78 (1H, d, J = 7.6 Hz), 5.31-5.28 (1H, m), 5.08 (1H, d, J = 5.4 Hz), 4.63-4.56 (1H, m), 3.77 (3H, s), 3.34 (1H, d, J = 5.9 Hz), 3.28 (1H, dd, J = 16.1, 7.3 Hz), 2.77 (1H, dd, J = 16.1, 6.6 Hz), 2.24 (3H, s), 1.60 (1H, brs), 1.29 (9H, s). | ESI[M + H]$^+$ 467 |
| 50a | 400 MHz, CDCl$_3$<br>δ: 7.88 (1H, d, J = 2.5 Hz), 7.26-7.21 (1H, m), 6.99 (1H, dd, J = 5.0, 1.0 Hz), 6.70 (1H, brs), 5.61 (1H, d, J = 7.8 Hz), 5.35-5.28 (1H, m), 5.14-5.12 (1H, m), 4.69-4.62 (1H, m), 3.79 (3H, s), 3.36 (1H, dd, J = 16.2, 7.5 Hz), 3.26 (1H, d, J = 6.1 Hz), 2.88 (1H, dd, J = 16.2, 6.8 Hz), 2.46 (1H, d, J = 4.8 Hz), 1.30 (9H, s). | ESI[M + H]$^+$ 471 |
| 50b | 400 MHz, CDCl$_3$<br>δ: 7.88 (1H, d, J = 2.0 Hz), 7.30-7.19 (3H, m), 7.00-6.96 (1H, m), 6.73 (1H, brs), 5.64 (1H, d, J = 7.3 Hz), 5.32-5.25 (1H, m), 5.14-5.11 (1H, m), 4.68-4.61 (1H, m), 3.78 (3H, s), 3.36 (1H, dd, J = 16.2, 6.8 Hz), 3.26 (1H, d, J = 6.1 Hz), 2.87 (1H, dd, J = 16.2, 6.8 Hz), 2.44 (1H, d, J = 4.9 Hz), 1.29 (9H, s). | ESI[M + H]$^+$ 471 |
| 51a | 400 MHz, CDCl$_3$<br>δ: 7.87 (1H, d, J = 3.2 Hz), 7.31-7.19 (4H, m), 6.79 (1H, brs), 5.68 (1H, d, J = 7.6 Hz), 5.32-5.28 (1H, m), 5.18-5.12 (1H, m), 4.66-4.60 (1H, m), 3.78 (3H, s), 3.39-3.33 (1H, m), 3.30 (1H, d, J = 6.0 Hz), 2.94-2.88 (1H, m), 1.29 (9H, s). | ESI[M + H]$^+$ 487 |
| 51b | 400 MHz, CDCl$_3$<br>δ: 7.89-7.88 (1H, m), 7.38-7.19 (4H, m), 6.59 (1H, brs), 5.52-5.49 (1H, m), 5.32-5.28 (1H, m), 5.18 (1H, d, J = 5.2 Hz), 4.68-4.62 (1H, m), 3.80 (3H, s), 3.43-3.35 (1H, m), 3.10-3.08 (1H, m), 2.94-2.89 (1H, m), 1.30 (9H, s). | ESI[M + H]$^+$ 487 |
| 52a | 400 MHz, CDCl$_3$<br>δ: 7.90 (1H, d, J = 2.8 Hz), 7.23-7.21 (2H, m), 7.02 (1H, d, J = 7.6 Hz), 6.81-6.78 (2H, m), 5.69 (1H, d, J = 7.9 Hz), 5.31-5.28 (1H, m), 5.09-5.07 (1H, m), 4.64-4.56 (1H, m), 3.81 (3H, s), 3.76 (3H, s), 3.40 (1H, d, J = 6.1 Hz), 3.30-3.24 (1H, m), 2.78 (1H, dd, J = 16.5, 6.4 Hz), 2.43-2.42 (1H, m), 1.28 (9H, brs). | ESI[M + H]$^+$ 483 |
| 52b | 400 MHz, CDCl$_3$<br>δ: 7.91 (1H, d, J = 2.4 Hz), 7.24-7.21 (2H, m), 7.04 (1H, d, J = 7.6 Hz), 6.80-6.75 (2H, m), 5.66 (1H, d, J = 7.5 Hz), 5.30 (1H, t, J = 6.6 Hz), 5.11-5.09 (1H, m), 4.64-4.58 (1H, m), 3.81 (3H, s), 3.77 (3H, s), 3.33-3.26 (2H, m), 2.80 (1H, dd, J = 16.1, 5.6 Hz), 2.35 (1H, brs), 1.28 (9H, brs). | ESI[M + H]$^+$ 483 |
| 55a | 400 MHz, CDCl$_3$<br>δ: 7.88 (1H, d, J = 2.4 Hz), 7.37-7.34 (1H, m), 7.24 (1H, brs), 6.97-6.91 (2H, m), 6.76 (1H, brs), 5.70 (1H, d, J = 8.0 Hz), 5.34-5.28 (1H, m), 5.05 (1H, brs), 4.65-4.60 (1H, m), 3.78 (3H, s), 3.30-3.24 (2H, m), 2.91-2.85 (1H, m), 2.32 (1H, brs), 1.29 (9H, brs). | ESI[M + H]$^+$ 471 |
| 55b | 400 MHz, CDCl$_3$<br>δ: 7.89 (1H, d, J = 2.4 Hz), 7.24-7.20 (2H, m), 7.02-6.69 (1H, m), 6.60 (1H, brs), 5.55-5.53 (1H, m), 5.34-5.31 (1H, m), 5.15 (1H, d, J = 8.0 Hz), 3.80 (3H, s), 4.65-4.60 (1H, m), 3.41 (1H, dd, J = 6.8, 5.8 Hz), 3.11-3.09 (2H, m), 2.92 (1H, dd, J = 6.4, 5.7 Hz), 2.31 (1H, brs), 1.34 (1H, brs). | ESI[M + H]$^+$ 471 |
| 57a | 400 MHz, CDCl$_3$<br>δ: 7.92-7.88 (1H, m), 7.58 (1H, brs), 7.32-7.30 (1H, m), 7.25-7.23 (1H, m), 6.80-6.73 (2H, m), 5.75-5.71 (1H, m), 5.33-5.28 (1H, m), 5.03 (1H, brs), 4.63-4.57 (1H, m), 3.87 (3H, s), 3.79 (3H, s), 3.30-3.21 (2H, m), 2.89 (1H, dd, J = 15.2, 7.2 Hz), 2.29-2.26 (1H, m), 1.30 (9H, s). | ESI[M + H]$^+$ 483 |

TABLE 3-continued

| Compound | NMR | MS |
|---|---|---|
| 57b | 400 MHz, CDCl$_3$<br>δ: 7.91 (1H, d, J = 2.8 Hz), 7.32-7.30 (1H, m), 7.22-7.20 (1H, m), 6.83-6.77 (2H, m), 6.73-6.70 (1H, m), 5.76 (1H, d, J = 7.8 Hz), 5.32-5.28 (1H, m), 5.04-5.01 (1H, m), 4.63-4.56 (1H, m), 3.79 (3H, s), 3.78 (3H, s), 3.31-3.22 (2H, m), 2.89 (1H, dd, J = 16.0, 7.2 Hz), 2.32 (1H, d, J = 4.8 Hz), 1.30 (9H, s). | ESI[M + H]$^+$<br>483 |
| 60a | 400 MHz, CDCl$_3$<br>δ: 7.86-7.84 (1H, m), 7.25-7.22 (1H, m), 7.18-7.08 (1H, m), 7.00-6.95 (1H, m), 6.85-6.77 (1H, m), 5.67 (1H, brs), 5.32-5.23 (1H, m), 5.09 (1H, d, J = 5.6 Hz), 4.65 (1H, brs), 3.78 (3H, s), 3.26-3.22 (2H, m), 2.87 (1H, dd, J = 6.4, 5.4 Hz), 2.25 (1H, brs), 1.27 (9H, brs). | ESI[M + H]$^+$<br>471 |
| 60b | 400 MHz, CDCl$_3$<br>δ: 7.86 (1H, d, J = 2.4 Hz), 7.24-7.21 (1H, m), 7.18-7.15 (1H, m), 7.11-7.08 (1H, m), 7.00-6.95 (1H, m), 6.79 (1H, brs), 5.67 (1H, brs), 5.31-5.26 (1H, m), 5.09 (1H, d, J = 5.6 Hz), 4.63 (1H, brs), 3.78 (3H, s), 3.26-3.20 (2H, m), 2.86 (1H, dd, J = 6.4, 5.4 Hz), 2.24 (1H, brs), 1.27 (9H, brs). | ESI[M + H]$^+$<br>471 |
| 62a | 400 MHz, CDCl$_3$<br>δ: 7.89 (1H, d, J = 2.4 Hz), 7.23 (1H, brs), 7.12 (1H, d, J = 8.4 Hz), 6.94 (1H, m), 6.89-6.82 (2H, m), 5.72-5.69 (1H, m), 5.32-5.28 (1H, m), 5.06 (1H, d, J = 5.4 Hz), 4.62-4.57 (1H, m), 3.78 (3H, s), 3.76 (3H, s), 3.46 (1H, brs), 3.23-3.17 (1H, m), 2.82-2.76 (1H, m), 2.54 (1H, brs), 1.28 (9H, s). | ESI[M + H]$^+$<br>483 |
| 62b | 400 MHz, CDCl$_3$<br>δ: 7.91 (1H, d, J = 2.8 Hz), 7.21 (1H, brs), 7.15 (1H, d, J = 8.4 Hz), 6.97 (1H, d, J = 2.4 Hz), 6.86 (1H, dd, J = 8.4, 2.6 Hz), 6.67 (1H, brs), 5.61 (1H, d, J = 7.6 Hz), 5.34-5.26 (1H, m), 5.09 (1H, t, J = 5.0 Hz), 4.64-4.59 (1H, m), 3.80 (3H, s), 3.78 (3H, s), 3.27-3.21 (2H, m), 2.86 (1H, dd, J = 15.6, 6.2 Hz), 2.32 (1H, d, J = 4.8 Hz), 1.27 (9H, brs). | ESI[M + H]$^+$<br>483 |
| 65a | 400 MHz, CDCl$_3$<br>δ: 7.93-7.90 (1H, m), 7.59-7.27 (2H, m), 7.04 (1H, d, J = 7.2 Hz), 6.94 (1H, t, J = 8.0 Hz), 6.64 (1H, brs), 5.77-5.73 (1H, m), 5.34-5.29 (1H, m), 4.64-4.59 (1H, m), 3.80 (3H, s), 3.35-3.31 (1H, m), 3.20-3.18 (2H, m), 2.96 (1H, dd, J = 14.8, 5.6 Hz), 2.31-2.26 (1H, m), 1.31 (9H, brs). | ESI[M + H]$^+$<br>471 |
| 65b | 400 MHz, CDCl$_3$<br>δ: 7.93-7.90 (1H, m), 7.59-7.27 (2H, m), 7.04 (1H, d, J = 7.2 Hz), 6.94 (1H, t, J = 8.0 Hz), 6.64 (1H, brs), 5.77-5.73 (1H, m), 5.34-5.29 (1H, m), 4.64-4.59 (1H, m), 3.80 (3H, s), 3.35-3.31 (1H, m), 3.20-3.18 (2H, m), 2.96 (1H, dd, J = 14.8, 5.6 Hz), 2.31-2.26 (1H, m), 1.31 (9H, brs). | ESI[M + H]$^+$<br>471 |
| 67a | 400 MHz, CDCl$_3$<br>δ: 7.91 (1H, d, J = 2.4 Hz), 7.26 (1H, brs), 7.12-7.10 (1H, m), 6.81-6.79 (1H, m), 6.75 (1H, d, J = 8.0 Hz), 6.59-6.58 (1H, m), 5.84-5.78 (1H, m), 5.32-5.28 (1H, m), 5.06 (1H, d, J = 5.4 Hz), 4.61-4.55 (1H, m), 3.83 (3H, s), 3.79 (3H, s), 3.30 (1H, brs), 3.23-3.17 (1H, m), 2.82-2.76 (1H, m), 2.32 (1H, brs), 1.28 (9H, s). | ESI[M + H]$^+$<br>483 |
| 67b | 400 MHz, CDCl$_3$<br>δ: 7.98 (1H, d, J = 2.4 Hz), 7.29-7.28 (1H, m), 7.20 (1H, brs), 6.86 (1H, d, J = 6.8 Hz), 6.75 (1H, d, J = 8.2 Hz), 6.62 (1H, brs), 5.83-5.81 (1H, m), 5.31-5.29 (2H, m), 4.64-4.56 (1H, m), 3.86 (3H, s), 3.79 (3H, s), 3.35 (1H, dd, J = 16.0, 7.2 Hz), 3.22-3.20 (1H, m), 2.97 (1H, dd, J = 16.4, 7.6 Hz), 2.37 (1H, brs), 1.27 (9H, s). | ESI[M + H]$^+$<br>483 |
| 68a | 400 MHz, CD$_3$OD<br>δ: 8.15-6.63 (5H, m), 5.37 (1H, q, J = 7.2 Hz), 5.15 (1H, d, J = 5.9 Hz), 4.38 (1H, ddd, J = 9.1, 7.7, 5.9 Hz), 3.75 (3H, s), 3.14 (1H, dd, J = 15.0, 7.7 Hz), 2.90 (1H, dd, J = 15.0, 9.1 Hz), 1.32 (9H, s). | ESI[M + H]$^+$<br>469 |
| 68b | 400 MHz, CD$_3$OD<br>δ: 8.15-6.63 (5H, m), 5.37 (1H, q, J = 7.2 Hz), 5.14 (1H, d, J = 5.4 Hz), 4.38 (1H, ddd, J = 9.1, 7.2, 5.4 Hz), 3.75 (3H, s), 3.14 (1H, dd, J = 15.0, 7.2 Hz), 2.90 (1H, dd, J = 15.0, 9.1 Hz), 1.32 (9H, s). | ESI[M + H]$^+$<br>469 |
| 73a | 400 MHz, CDCl$_3$<br>δ: 7.88 (1H, d, J = 2.4 Hz), 7.25 (1H, brs), 6.99-6.86 (1H, m), 6.84 (1H, brs), 5.85 (1H, d, J = 8.0 Hz), 5.55-5.53 (1H, m), 5.37-5.27 (2H, m), 4.68-4.60 (1H, m), 3.80 (3H, s), 3.42-3.36 (1H, m), 2.86 (1H, dd, J = 16.0, 8.0 Hz), 2.64 (1H, brs), 1.30 (9H, s). | ESI[M + H]$^+$<br>489 |
| 73b | 400 MHz, CDCl$_3$<br>δ: 7.88 (1H, d, J = 2.4 Hz), 7.25 (1H, brs), 7.00-6.86 (1H, m), 5.91 (1H, d, J = 8.0 Hz), 5.55-5.53 (1H, m), 5.34-5.27 (2H, m), 4.67-4.59 (1H, m), 3.78 (3H, s), 3.43 (1H, dd, J = 16.0, 7.6 Hz), 2.88 (1H, dd, J = 16.0, 8.0 Hz), 2.70 (1H, brs), 1.26 (9H, s). | ESI[M + H]$^+$<br>489 |
| 79a | 400 MHz, CDCl$_3$<br>δ: 7.97 (1H, d, J = 1.9 Hz), 7.37 (1H, d, J = 7.4 Hz), 7.32-7.19 (4H, m), 6.52 (1H, s), 5.67 (1H, d, J = 7.1 Hz), 5.34-5.29 (1H, m), 4.70-4.65 (1H, m), 4.60 (1H, d, J = 5.7 Hz), 3.79 (3H, s), 3.40 (3H, s), 3.27 (1H, dd, J = 15.3, 6.8 Hz), 3.21 (1H, brs), 2.97 (1H, dd, J = 15.3, 7.1 Hz), 1.30 (9H, s). | ESI[M + H]$^+$<br>467 |
| 79b | 400 MHz, CDCl$_3$<br>δ: 7.96 (1H, d, J = 2.2 Hz), 7.37 (1H, d, J = 7.5 Hz), 7.32-7.19 (4H, m), 6.53 (1H, s), 5.68 (1H, d, J = 7.5 Hz), 5.31 (1H, dd, J = 6.8, 6.8 Hz), 4.72-4.65 (1H, m), 4.59 (1H, d, J = 5.4 Hz), 3.79 (3H, s), 3.40 (3H, s), 3.26 (1H, dd, J = 15.8, 7.3 Hz), 3.16 (1H, d, J = 6.3 Hz), 2.94 (1H, dd, J = 15.9, 7.1 Hz), 1.30 (9H, s). | ESI[M + H]$^+$<br>467 |

TABLE 3-continued

| Compound | NMR | MS |
|---|---|---|
| 82a | 400 MHz, CDCl$_3$<br>δ: 8.31-6.88 (7H, m), 5.64 (1H, d, J = 7.6 Hz), 5.32-5.26 (1H, m), 5.13 (1H, brs), 4.62-4.55 (1H, m), 3.76 (3H, s), 3.32 (1H, dd, J = 15.9, 6.8 Hz), 3.19 (1H, brs), 2.91 (1H, dd, J = 15.9, 6.8 Hz), 2.28 (1H, brs). | ESI[M + H]$^+$ 475 |
| 82b | 400 MHz, CDCl$_3$<br>δ: 8.27-6.98 (7H, m), 5.72 (1H, d, J = 7.6 Hz), 5.32-5.26 (1H, m), 5.10 (1H, brs), 4.59-4.52 (1H, m), 3.74 (3H, s), 3.35 (1H, brs), 3.29 (1H, dd, J = 16.1, 7.3 Hz), 2.89 (1H, dd, J = 16.1, 6.6 Hz), 2.43 (1H, brs). | ESI[M + H]$^+$ 475 |
| 83a | 400 MHz, CDCl$_3$<br>δ: 7.61-6.71 (7H, m), 5.66 (1H, d, J = 7.8 Hz), 5.32-5.24 (1H, m), 5.10 (1H, d, J = 5.6 Hz), 4.62-4.55 (1H, m), 3.84-3.80 (4H, m), 3.72 (4H, s), 3.28 (1H, dd, J = 16.1, 7.1 Hz), 3.10-3.07 (4H, m), 2.89 (1H, dd, J = 16.1, 6.3 Hz), 2.51 (1H, brs). | ESI[M + H]$^+$ 482 |
| 83b | 400 MHz, CDCl$_3$<br>δ: 7.62-6.68 (7H, m), 5.79 (1H, d, J = 7.1 Hz), 5.30-5.25 (1H, m), 5.12 (1H, d, J = 5.1 Hz), 4.61-4.55 (1H, m), 3.82-3.78 (4H, m), 3.72 (1H, brs), 3.70 (3H, s), 3.25 (1H, dd, J = 16.1, 6.6 Hz), 3.09-3.00 (4H, m), 2.84 (1H, dd, J = 16.1, 6.6 Hz), 2.50 (1H, brs). | ESI[M + H]$^+$ 482 |
| 84a | 400 MHz, CDCl$_3$<br>δ: 7.58-6.71 (5H, m), 6.39 (1H, brs), 5.66 (1H, d, J = 7.8 Hz), 5.29-5.23 (1H, m), 5.11 (1H, d, J = 5.1 Hz), 4.64-4.57 (1H, m), 3.89 (1H, brs), 3.84-3.79 (4H, m), 3.72 (3H, s), 3.33 (1H, dd, J = 16.3, 7.3 Hz), 3.10-3.06 (4H, m), 2.87 (1H, dd, J = 16.3, 6.3 Hz), 2.66 (1H, brs). | ESI[M + H]$^+$ 500 |
| 84b | 400 MHz, CDCl$_3$<br>δ: 7.54-6.69 (6H, m), 5.77 (1H, d, J = 7.8 Hz), 5.29-5.24 (1H, m), 5.12 (1H, d, J = 4.6 Hz), 4.63-4.57 (1H, m), 3.89 (1H, brs), 3.83-3.78 (4H, m), 3.69 (3H, s), 3.30 (1H, dd, J = 16.3, 7.3 Hz), 3.08-2.96 (4H, m), 2.83 (1H, dd, J = 16.3, 6.1 Hz), 2.70 (1H, brs). | ESI[M + H]$^+$ 500 |
| 92a | 400 MHz, CDCl$_3$<br>δ: 7.42-6.71 (6H, m), 6.32 (1H, brs), 5.68 (1H, d, J = 7.3 Hz), 5.30-5.23 (1H, m), 5.09 (1H, brs), 4.64-4.57 (1H, m), 3.71 (3H, s), 3.43 (1H, brs), 3.27 (1H, dd, J = 16.1, 7.6 Hz), 3.24-3.20 (4H, m), 2.88 (1H, dd, J = 16.1, 6.8 Hz), 2.49 (1H, brs), 1.99-1.95 (4H, m). | ESI[M + H]$^+$ 466 |
| 92b | 400 MHz, CDCl$_3$<br>δ: 7.43-6.70 (6H, m), 6.31 (1H, brs), 5.70 (1H, d, J = 7.8 Hz), 5.28-5.21 (1H, m), 5.11 (1H, d, J = 4.6 Hz), 4.65-4.58 (1H, m), 3.71 (3H, s), 3.39 (1H, brs), 3.27 (1H, dd, J = 16.1, 7.1 Hz), 3.24-3.21 (4H, m), 2.88 (1H, dd, J = 16.1, 6.6 Hz), 2.41 (1H, brs), 1.99-1.95 (4H, m). | ESI[M + H]$^+$ 466 |
| 93a | 400 MHz, CDCl$_3$<br>δ: 7.25-6.73 (5H, m), 6.34 (1H, brs), 5.67 (1H, d, J = 7.8 Hz), 5.30-5.24 (1H, m), 5.11 (1H, brs), 4.68-4.61 (1H, m), 3.72 (3H, s), 3.37 (1H, d, J = 6.1 Hz), 3.33 (1H, dd, J = 16.1, 7.1 Hz), 3.24-3.20 (4H, m), 2.86 (1H, dd, J = 16.1, 6.6 Hz), 2.64 (1H, brs), 1.99-1.96 (4H, m). | ESI[M + H]$^+$ 484 |
| 93b | 400 MHz, CDCl$_3$<br>δ: 7.25-6.73 (5H, m), 6.33 (1H, brs), 5.67 (1H, d, J = 8.0 Hz), 5.28-5.22 (1H, m), 5.13 (1H, brs), 4.68-4.61 (1H, m), 3.72 (3H, s), 3.36 (1H, brs), 3.33 (1H, dd, J = 16.3, 7.6 Hz), 3.24-3.21 (4H, m), 2.86 (1H, dd, J = 16.3, 6.6 Hz), 2.62 (1H, brs), 1.99-1.96 (4H, m). | ESI[M + H]$^+$ 484 |
| 97a | 400 MHz, CDCl$_3$<br>δ: 7.51-6.73 (7H, m), 5.58 (1H, d, J = 7.3 Hz), 5.29-5.22 (1H, m), 5.11 (1H, d, J = 5.4 Hz), 4.62-4.55 (1H, m), 3.72 (3H, s), 3.48 (1H, brs), 3.28 (1H, dd, J = 16.1, 7.3 Hz), 3.10-3.07 (4H, m), 2.89 (1H, dd, J = 16.1, 6.3 Hz), 2.49 (1H, brs), 1.69-1.57 (6H, m). | ESI[M + H]$^+$ 480 |
| 97b | 400 MHz, DMSO-d$_6$<br>δ: 8.28-7.19 (7H, m), 6.66 (1H, d, J = 4.6 Hz), 6.57 (1H, brs), 5.46 (1H, brs), 5.22 (1H, brs), 4.87 (1H, brs), 4.29 (1H, brs), 3.58 (3H, s), 3.08-2.74 (6H, m), 1.61-1.50 (6H, m). | ESI[M + H]$^+$ 480 |
| 102a | 400 MHz, CDCl$_3$<br>δ: 7.42-6.67 (6H, m), 6.45 (1H, brs), 5.64 (1H, d, J = 7.8 Hz), 5.28-5.22 (1H, m), 5.09 (1H, brs), 4.64-4.57 (1H, m), 3.72 (3H, s), 3.41-3.38 (4H, m), 3.35 (1H, brs), 3.27 (1H, dd, J = 16.2, 7.3 Hz), 2.88 (1H, dd, J = 16.2, 6.6 Hz), 2.43 (1H, brs), 1.76 (4H, brs), 1.52 (4H, brs). | ESI[M + H]$^+$ 494 |
| 102b | 400 MHz, CDCl$_3$<br>δ: 7.42-6.73 (6H, m), 6.44 (1H, brs), 5.70 (1H, d, J = 7.8 Hz), 5.25-5.19 (1H, m), 5.09 (1H, brs), 4.64-4.57 (1H, m), 3.70 (3H, s), 3.42 (1H, brs), 3.40-3.37 (4H, m), 3.26 (1H, dd, J = 16.1, 7.3 Hz), 2.87 (1H, dd, J = 16.1, 6.6 Hz), 2.44 (1H, brs), 1.75 (4H, brs), 1.54-1.50 (4H, m). | ESI[M + H]$^+$ 494 |
| 108a | 400 MHz, CDCl$_3$<br>δ: 8.00 (1H, d, J = 2.0 Hz), 7.45-7.22 (4H, m), 7.16 (1H, d, J = 2.0 Hz), 6.59 (1H, s), 5.56-5.45 (1H, m), 5.37-5.30 (1H, m), 5.15-5.10 (1H, m), 4.65-4.60 (1H, m), 3.82 (3H, s), 3.80-3.55 (4H, m), 3.37-3.30 (1H, m), 3.05-2.90 (1H, m), 1.80-1.65 (4H, m), 1.26 (3H, s). | ESI[M + H]$^+$ 495 |
| 108b | 400 MHz, CDCl$_3$<br>δ: 7.86 (1H, d, J = 2.0 Hz), 7.41 (1H, d, J = 6.8 Hz), 7.32-7.22 (3H, m), 7.16 (1H, d, J = 2.0 Hz), 6.87 (1H, s), 5.85-5.78 (1H, m), 5.37-5.28 (1H, m), 5.10 (1H, d, J = 5.6 Hz), 4.65-4.55 (1H, m), 3.74 (3H, s), 3.71-3.55 (4H, m), 3.27 (1H, dd, J = 16.0, 6.0 Hz), 2.89 (1H, dd, J = 16.0, 6.0 Hz), 2.01-1.55 (4H, m), 1.22 (3H, s). | ESI[M + H]$^+$ 495 |

TABLE 3-continued

| Compound | NMR | MS |
|---|---|---|
| 123a | 400 MHz, CDCl$_3$<br>δ: 7.85 (1H, d, J = 3.6 Hz), 7.43-7.40 (1H, m), 7.29-7.25 (2H, m), 7.17 (1H, brs), 6.64 (1H, brs), 5.60 (1H, d, J = 7.8 Hz), 5.33-5.30 (1H, m), 5.12 (1H, t, J = 7.6 Hz), 4.65-4.61 (1H, m), 3.80 (3H, s), 3.34-3.24 (2H, m), 2.93 (1H, q, J = 3.9 Hz), 2.24 (1H, d, J = 7.8 Hz), 1.28-1.24 (8H, m), 1.28 (3H, t, J = 6.4 Hz). | ESI[M + H]$^+$<br>467 |
| 123b | 400 MHz, CDCl$_3$<br>δ: 7.85 (1H, d, J = 3.6 Hz), 7.41-7.40 (1H, m), 7.28-7.24 (2H, m), 7.19 (1H, brs), 6.67 (1H, brs), 5.60-5.57 (1H, m), 5.33-5.30 (1H, m), 5.12 (1H, t, J = 7.6 Hz), 4.65-4.62 (1H, m), 3.81 (3H, s), 3.34-3.24 (2H, m), 2.93-2.85 (1H, m), 2.24 (1H, d, J = 7.4 Hz), 1.30-1.24 (8H, m), 1.26 (3H, t, J = 6.0 Hz). | ESI[M + H]$^+$<br>467 |
| 135a | 400 MHz, CDCl$_3$<br>δ: 7.68-6.75 (7H, m), 5.64 (1H, d, J = 8.0 Hz), 5.34-5.26 (1H, m), 5.10 (1H, brs), 4.64-4.58 (1H, m), 3.81 (3H, s), 3.54 (1H, brs), 3.30 (1H, dd, J = 15.9, 7.3 Hz), 2.90 (1H, dd, J = 15.9, 6.6 Hz), 2.35-1.75 (7H, m), 1.42 (3H, s). | ESI[M + H]$^+$<br>465 |
| 135b | 400 MHz, CDCl$_3$<br>δ: 7.70-6.73 (7H, m), 5.61 (1H, d, J = 8.0 Hz), 5.32-5.25 (1H, m), 5.10 (1H, brs), 4.66-4.58 (1H, m), 3.80 (3H, s), 3.55 (1H, brs), 3.30 (1H, dd, J = 15.9, 6.8 Hz), 2.89 (1H, dd, J = 15.9, 6.8 Hz), 2.35-1.76 (7H, m), 1.42 (3H, s). | ESI[M + H]$^+$<br>465 |

Comparative Example 1

Synthesis of 1-(5-tert-butyl-2-methoxy-3-(2,2,2-trifluoro-1-hydroxyethyl)phenyl)-3-(2,3-dihydro-1H-inden-2-yl)urea (Comparative Compound 1)

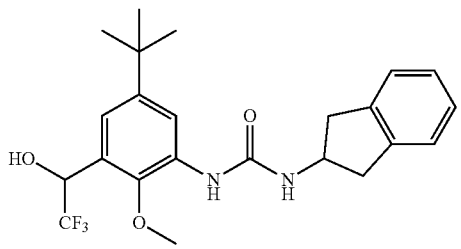 [SMILES: COc1c(NC(=O)NC2Cc3ccccc3C2)cc(C(C)(C)C)cc1C(O)C(F)(F)F]

To a solution of 2,2,2-trichloroethyl 5-tert-butyl-2-methoxy-3-(2,2,2-trifluoro-1-hydroxyethyl)phenylcarbamate (0.150 g, 0.331 mmol) and 2-aminoindane (0.053 g, 0.398 mmol) in acetonitrile (1.0 mL), N,N-diisopropylethylamine (0.173 mL, 0.994 mmol) was added, and the mixture was stirred at 110° C. for 18 hours. The reaction mixture was evaporated under reduced pressure. The obtained residue was purified by silica gel column chromatography (ethyl acetate/n-hexane=0/100-60/40) to obtain 0.133 g of the captioned compound (92% yield).

$^1$H-NMR (400MHz, CDCl$_3$) δ: 7.85 (1H, d, J=2.1 Hz), 7.23-7.15 (5H, m), 6.67 (1H, s), 5.29-5.23 (2H, m), 4.67-4.61 (1H, m), 3.72 (3H, s), 3.32 (2H, dd, J=16.1, 6.9 Hz), 3.26 (1H, d, J=6.3 Hz), 2.83 (2H, td, J=16.1, 4.6 Hz), 1.26 (9H, s).

MS (ESI): 437 ([M+H]$^+$).

Comparative Example 2

Synthesis of 1-(5-tert-butyl-3-(hydroxymethyl)-2-methoxyphenyl)-3-(2,3-dihydro-1H-inden-2-yl)urea (Comparative Compound 2)

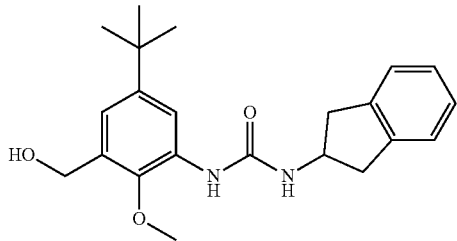 [SMILES: COc1c(CO)cc(C(C)(C)C)cc1NC(=O)NC1Cc2ccccc2C1]

To a solution of 2,2,2-trichloroethyl 5-tert-butyl-3-(hydroxymethyl)-2-methoxyphenylcarbamate (0.096 g, 0.250 mmol) and 2-aminoindane (0.033 g, 0.248 mmol) in acetonitrile (1.0 mL), N,N-diisopropylethylamine (0.065 mL, 0.38 mmol) was added, and the mixture was stirred at 70° C. for 12 hours. The reaction mixture was evaporated under reduced pressure. The obtained residue was purified by silica gel column chromatography (ethyl acetate/n-hexane=0/100-60/40) to obtain 0.092 g (quantitative) of the captioned compound.

$^1$H-NMR (400MHz, CDCl$_3$) δ: 7.84-6.90 (7H, m), 5.34 (1H, d, J=6.8 Hz), 4.65-4.64 (3H, m), 3.72 (3H, s), 3.35-3.29 (2H, m), 2.87-2.82 (2H, m), 2.09 (1H, brs), 1.26 (9H, s).

MS (ESI): 369 ([M+H]$^+$).

Comparative Example 3

Synthesis of 1-(5-tert-butyl-3-(2-cyanopropan-2-yl)-2-methoxyphenyl)-3-((1S,2R)-1-hydroxy-2,3-dihydro-1H-inden-2-yl)urea (Comparative Compound 3)

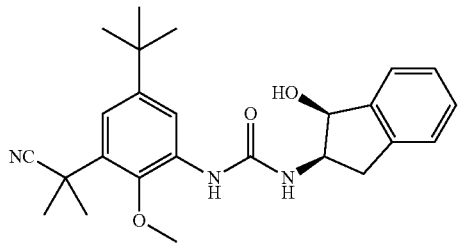 [SMILES: COc1c(NC(=O)N[C@@H]2Cc3ccccc3[C@@H]2O)cc(C(C)(C)C)cc1C(C)(C)C#N]

1st Step

Synthesis of 5-tert-butyl-1-(chloromethyl)-2-methoxy-3-nitrobenzene

To a solution of (5-tert-butyl-2-methoxy-3-nitrophenyl)methanol (4.59 g, 19.2 mmol) in chloroform (20 mL), thionyl chloride (2.80 mL, 38.4 mmol) was added, and the mixture was stirred overnight under reflux. After cooling the mixture to room temperature and evaporated under reduced pressure and water was added to the residue. The resultant was extracted with ethyl acetate and then dried over anhydrous sodium sulfate, evaporated under reduced pressure. The obtained residue was purified by silica gel column chromatography (ethyl acetate/n-hexane=0/100-30/70) to obtain 1.95 g (39% yield) of the captioned compound.

2nd Step

Synthesis of 2-(5-tert-butyl-2-methoxy-3-nitrophenyl)acetonitrile

To a mixed solution of 5-tert-butyl-1-(chloromethyl)-2-methoxy-3-nitrobenzene (1.93 g, 7.49 mmol) in dioxane (5.0 mL), ethanol (5.0 mL) and water (2.5 mL), potassium cyanide (0.980 g, 15.0 mmol) was added, and the mixture was stirred for 2 hours under reflux. After cooling the mixture to room temperature and evaporated under reduced pressure and water was added to the residue. The resultant was extracted with ethyl acetate and then dried over anhydrous sodium sulfate, evaporated under reduced pressure. The obtained residue was purified by silica gel column chromatography (ethyl acetate/n-hexane=0/100-30/70) to obtain 1.84 g of the captioned compound (99% yield).

3rd Step

Synthesis of 2-(5-tert-butyl-2-methoxy-3-nitrophenyl)-2-methylpropanenitrile To a suspension of sodium hydroxide (60%) (0.097 g, 2.42 mmol) in THF (3.2 mL), 2-(5-tert-butyl-2-methoxy-3-nitrophenyl)acetonitrile (0.200 g, 0.806 mmol) was added, and the mixture was stirred at room temperature for 20 minutes. To this mixture, methyl iodide (0.121 mL, 1.93 mmol) was added and stirred overnight at room temperature. Water was added to the reaction mixture and the mixture was extracted with ethyl acetate. The filtrate was dried over anhydrous sodium sulfate and then evaporated under pressure. The obtained residue was purified by silica gel column chromatography (ethyl acetate/n-hexane=0/100-30/70) to obtain 0.088 g of the captioned compound (39% yield).

4th Step

Synthesis of 2-(3-amino-5-tert-butyl-2-methoxyphenyl)-2-methylpropanenitrile To a solution of 2-(5-tert-butyl-2-methoxy-3-nitrophenyl)-2-methylpropanenitrile (0.086 g, 0.311 mmol) in ethanol (3.1 mL), iron (0.087 g, 1.56 mmol), ammonium chloride (0.083 g, 1.56 mmol) and water (1.6 mL) were added, and the mixture was stirred for 3 hours under reflux. The reaction mixture was filtered and washed with ethanol. The obtained filtrate was evaporated under reduced pressure and the residue was dissolved in dichloromethane. After washing this solution with water and then saturated brine, the solution was dried over anhydrous sodium sulfate. The solvent was evaporated under reduced pressure and the obtained residue was purified by silica gel column chromatography (ethyl acetate/n-hexane=0/100-30/70) to obtain 0.051 g of the captioned compound (67% yield).

5th Step

Synthesis of 2,2,2-trichloroethyl 5-tert-butyl-3-(2-cyanopropan-2-yl)-2-methoxyphenylcarbamate To a solution of 2-(3-amino-5-tert-butyl-2-methoxyphenyl)-2-methylpropanenitrile (0.050 g, 0.202 mmol) in THF (0.6 mL), 2,2,2-trichloroethyl chloroformate (0.052 g, 0.245 mmol) and N,N-diisopropylethylamine (0.053 mL, 0.304 mmol) was added, and the mixture was stirred at room temperature for 2 hours. The reaction solution was evaporated under reduced pressure, and the obtained residue was purified by silica gel column chromatography (ethyl acetate/n-hexane=0/100-30/70) to obtain 0.086 g (quantitative) of the captioned compound.

6th Step

Synthesis of 1-(5-tert-butyl-3-(2-cyanopropan-2-yl)-2-methoxyphenyl)-3-((1S,2R)-1-hydroxy-2,3-dihydro-1H-inden-2-yl)urea (Comparative Compound 3)

To a solution of 2,2,2-trichloroethyl 5-tert-butyl-3-(2-cyanopropan-2-yl)-2-methoxyphenylcarbamate (0.086 g, 0.203 mmol) and (1S,2R)-2-amino-2,3-dihydro-1H-indene-1-ol.L-tartaric acid salt (0.067 g, 0.223 mmol) in acetonitrile (0.8 mL), N,N-diisopropylethylamine (0.058 mL, 0.333 mmol) was added, the mixture was stirred overnight at 110° C. The reaction mixture was evaporated under reduced pressure and the obtained residue was purified by silica gel column chromatography (ethyl acetate/n-hexane=10/90-60/40) to obtain 0.044 g of the captioned compound (51% yield).

$^1$H-NMR (400MHz, CDCl$_3$) δ: 7.64-7.06 (6H, m), 6.40 (1H, s), 5.66 (1H, d, J=8.0 Hz), 5.11 (1H, dd, J=5.4, 5.1 Hz), 4.68-4.61 (1H, m), 3.93 (3H, s), 3.32 (1H, dd, J=15.9, 7.3 Hz), 2.89 (1H, dd, J=15.9, 6.6 Hz), 2.14 (1H, d, J=5.1 Hz), 1.74 (3H, s), 1.73 (3H, s), 1.29 (9H, s).

MS (ESI): 422 ([M+H]$^+$).

Comparative Example 4

Synthesis of 1-(3-tert-butyl-1-p-tolyl-1H-pyrazol-5-yl)-3-(4-(2-morpholinoethoxy)naphthalen-1-yl)urea (Comparative Compound 4) and 1-(3-tert-butyl-1-p-tolyl-1H-pyrazol-5-yl)-3-(4-(2-morpholinoethoxy)naphthalen-1-yl)urea.hydrochloride (Comparative Compound 4c)

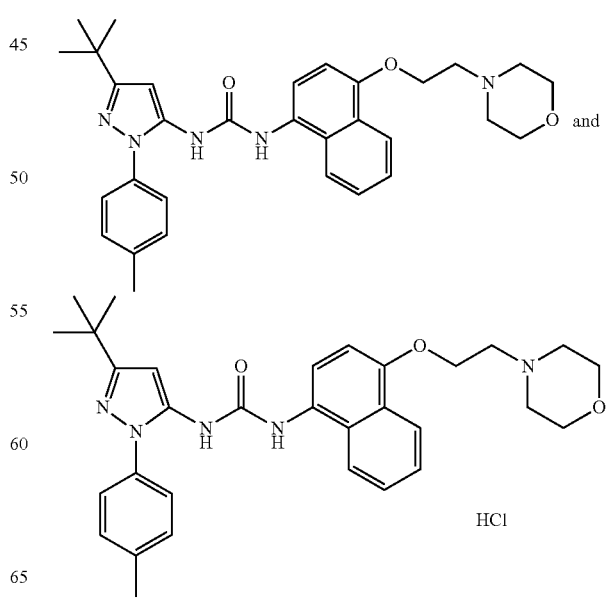

1st Step

Synthesis of 3-tert-butyl-1-p-tolyl-1H-pyrazol-5-amine.hydrochloride

A solution of p-tolylhydrazine.hydrochloride (76.0 g, 479 mmol) and pivaloylacetonitrile (85.0 g, 679 mmol) in methanol (350 mL) was heated to reflux. After 15 hours, the mixture was allowed to cool to room temperature and then methanol was evaporated under reduced pressure. To the obtained residue, diethyl ether was added, followed by recrystallizing the resultant to obtain 108.2 g of the captioned compound (85% yield).

2nd Step

Synthesis of 2,2,2-trichloroethyl 3-tert-butyl-1-p-tolyl-1H-pyrazol-5-yl carbamate A suspension of 3-tert-butyl-1-p-tolyl-1H-pyrazol-5-amine.hydrochloride (75.0 g, 282 mmol) in ethyl acetate (500 mL) was cooled to 0° C., and aqueous solution (250 mL) of sodium hydroxide (30.0 g, 750 mmol) was added dropwise thereto for 30 minutes. After stirring the resulting mixture for further 30 minutes, 2,2,2-trichloroethyl chloroformate (55.2 mL, 401 mmol) was added dropwise thereto for 30 minutes. After completion of the dropping, the resulting mixture was stirred at room temperature for 1.5 hours, and the organic layer was separated. The aqueous layer was extracted with ethyl acetate, and the resultant was combined with the organic layer, followed by washing the organic layer sequentially with water, aqueous saturated sodium bicarbonate solution, water and with saturated brine. The organic layer was dried over anhydrous sodium sulfate and filtered, and the solvent was evaporated under reduced pressure. To the obtained residue, n-hexane was added and the generated precipitates were collected by filtration to obtain 97.81 g of the captioned compound (85% yield).

3rd Step

Synthesis of 4-(2-(4-nitronaphthalen-1-yloxy)ethyl)morpholine

A suspension of 4-nitronaphthalen-1-ol (10.1 g, 53.4 mmol), 4-(2-chloroethyl)morpholine.hydrochloride (14.0 g, 75.2 mmol), sodium hydroxide (3.11 g, 77.8 mmol) and potassium carbonate (17.5 g, 127 mmol) in 1-methylpyrrolidine-2-one (180 mL) was stirred at 100° C. After 3 hours, the reaction solution was cooled to 0° C., water (200 mL) was added thereto, followed by stirring the mixture. The precipitated crystals were collected by filtration to obtain 14.31 g of the captioned compound (88% yield).

4th Step

Synthesis of 1-(3-tert-butyl-1-p-tolyl-1H-pyrazol-5-yl)-3-(4-(2-morpholinoethoxy)naphthalen-1-yl)urea (Comparative Compound 4)

To a mixed solution of 4-(2-(4-nitronaphthalen-1-yloxy)ethyl)morpholine (11.18 g, 36.9 mmol) in methanol (90 mL) and THF (30 mL), 5% palladium/activated charcoal (0.500 g) was added and the resulting mixture was stirred at room temperature under hydrogen atmosphere. After 23 hours, the insoluble materials were filtered and the solvent was evaporated under reduced pressure. To the obtained residue, 2,2,2-trichloroethyl 3-tert-butyl-1-p-tolyl-1H-pyrazol-5-yl carbamate (16.1 g, 39.7 mmol), N,N-diisopropylethylamine (8.50 mL) and DMSO (30 mL) was added and the mixture was stirred at 60° C. After 18 hours, the temperature of the reaction solution was returned to room temperature and saturated brine was added thereto. The aqueous layer was extracted with ethyl acetate and then dried over anhydrous sodium sulfate and the solvent was evaporated under reduced pressure. The obtained residue was purified by silica gel column chromatography (ethyl acetate/n-hexane=50/50-ethyl acetate/methanol=90/10) to obtain 13.58 g of the captioned compound (69% yield).

5th Step

Synthesis of 1-(3-tert-butyl-1-p-tolyl-1H-pyrazol-5-yl)-3-(4-(2-morpholinoethoxy)naphthalen-1-yl)urea.hydrochloride (Comparative Compound 4c)

To 1-(3-tert-butyl-1-p-tolyl-1H-pyrazol-5-yl)-3-(4-(2-morpholinoethoxy)naphthalen-1-yl)urea (6.38 g, 12.1 mmol), 0.1N hydrochloric acid (121 mL) and water (150 mL) was added and dissolved therein. The solvent was removed by lyophilization method to obtain 6.91 g (quantitative) of the captioned compound.

$^1$H-NMR (400MHz, DMSO-$d_6$) δ: 10.95 (1H, s), 8.96 (1H, s), 8.79 (1H, s), 8.30 (1H, d, J=7.6 Hz), 7.99 (1H, d, J=7.6 Hz), 7.68 (1H, d, J=8.3 Hz), 7.61-7.54 (2H, m), 7.46 (2H, d, J=8.4 Hz), 7.35 (2H, d, J=8.4 Hz), 7.01 (1H, d, J=8.3 Hz), 6.35 (1H, s), 4.58-4.55 (2H, m), 4.01-3.98 (2H, m), 3.83-3.77 (2H, m), 3.73-3.71 (2H, m), 3.57-3.54 (2H, m), 3.33-3.28 (2H, m), 2.39 (3H, s), 1.28 (9H, s).

Comparative Example 5

4-(4-(4-fluorophenyl)-2-(4-(methylsulfinyl)phenyl)-1H-imidazol-5-yl)pyridine (Comparative Compound 5)

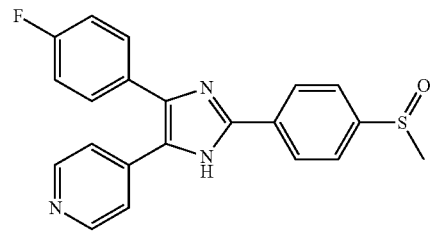 [SMILES: CS(=O)c1ccc(-c2nc(-c3ccc(F)cc3)c(-c3ccncc3)[nH]2)cc1]

The captioned compound was purchased from a commercially available reagent (Sigma-Aldrich).

1) Evaluation of p38 MAPK Inhibitory Activity by Compound

Using human p38 MAPK α, the p38 MAPK inhibitory activity of Compound (I) was studied by a method partially modified from the method described in *Current Medicinal Chemistry* (2004, No. 11, pp. 721-730).

A solution of each test compound solution in 100% DMSO and a p38α/SAPK2a solution (Final Concentration: 1.5 nM) (Invitrogen) were added to a 384-well plate, and then the plate was incubated at room temperature in a dark place for 1 hour. Thereafter, ATP (Final Concentration: 100 μM), which is a phosphate donor, and biotinylated ATF2 (Final Concentration: 30 nM) (upstate), which is a substrate, were added, and the resulting mixture was allowed to react at room temperature in a dark place for 1 hour (the final concentration of DMSO was 0.25%). After the reaction, an anti-phosphorylated ATF2 antibody (Final Concentration: 1 nM) (Cell Signaling), anti-IgG acceptor beads (Final Concentration: 20

µg/mL) (PerkinElmer) and streptavidin donor beads (Final Concentration: 20 µg/mL) (PerkinElmer) were added, and the resultant was incubated at room temperature in a dark place for 1 hour. Using a microplate analyzer (Fusion-α, Packard) in Alpha Screen method (Amplified Luminescent Proximity Homogeneous Assay), the light emission was detected. The $IC_{50}$ value of each compound was calculated by sigmoidal dose-response regression using Prism 4.02 (GraphPad Software, Inc.). The results are shown in Table 4. As a comparative control compound, Comparative Compound 1 was used.

TABLE 4

| Compound | p38 MAPK inhibitory activity $IC_{50}$ (nM) |
|---|---|
| 3 | 3 |
| 46b | 15 |
| 47b | 18 |
| 50b | 35 |
| 52b | 24 |
| 84b | 16 |
| 92b | 51 |
| 108b | 13 |
| 123b | 29 |
| Comparative Compound 1 | 117 |

As is apparent from the results in Table 4, Compound (I) exhibited a markedly higher p38 MAPK inhibitory activity than the comparative control compound.

2) Evaluation of Cytokine Production Suppressing Activity by Compound Using Human Whole Blood Using human whole blood, the inhibitory action of Compound (I) on the TNFα production by LPS stimulation was studied by a method partially modified from the method described in *Journal of Medicinal Chemistry* (2003, Vol. 46, pp. 4676-4686).

A solution of each test compound in 100% DMSO and human blood were mixed in a 96-well flat-bottom plate. Thereafter, LPS (Final Concentration: 200 ng/mL) was added, and the resulting mixture was allowed to react at 37° C. for 5 hours (the final concentration of DMSO was 0.2%). After the reaction, the resultant was centrifuged for 20 minutes at room temperature, and the supernatant was collected. For the measurement of the TNFα amount in the supernatant, a human cytokine kit (CIS bio international) was used. The results are shown in Table 5. As a comparative control compound, Comparative Compound 2 was used.

TABLE 5

| Compound | TNFα production suppressing activity $IC_{50}$ (nM) |
|---|---|
| 3 | 235 |
| 46b | 508 |
| 50b | 46 |
| 52b | 109 |
| 60b | 182 |
| 84b | 115 |
| Comparative Compound 2 | 5190 |

As is apparent from the results in Table 5, Compound (I) markedly suppressed the TNFα production compared to the comparative control compound.

3) Evaluation of Compound in Mouse LPS-Induced Cytokine Production Model

The action of Compound (I) on the TNFα production induced by LPS administration in a mouse was studied by a method partially modified from the method described in *Journal of Immunology* (1992, Vol. 148, pp. 1890-1897).

To each BALB/c mouse (male, 7 to 9-week old, Charles River Laboratories Japan, Inc.), LPS (0111:B4, SIGMA) was intraperitoneally administered at a dose of 1 mg/kg. Sixty minutes after the LPS administration, blood was collected from the abdominal vena cava under anesthesia and centrifuged for 15 minutes at 4° C. to obtain a serum. For the measurement of TNF-α in the serum, ELISA Development System (R&D Systems) was used. Each test compound was dissolved in DMSO (Final Concentration: 2%), and then the obtained solution was dissolved in a 27% aqueous solution of 2-hydroxypropyl-β-cyclodextrin (hereinafter referred to as "HP-β-CD"; Nihon Shokuhin Kako Co., Ltd.). Thirty minutes before the LPS administration, the resulting solution was orally administered at 50 mg/kg. As a result, the TNFα production by the oral administration of Compound 46b described in the Examples was significantly suppressed compared to the solvent-administered group (Suppression Ratio: 100.0%, Welch's test (Significance Level: less than 5%)).

As a comparative control compound, Comparative Compound 3 was used. The suppression ratio of the TNFα production by Comparative Compound 3 was 17.0%.

As is apparent from the results, Compound (I) exhibited a markedly higher oral activity than the comparative control compound.

4) Pharmacokinetic Evaluation of Compound in Mouse

Each test compound was dissolved in 10% HP-β-CD (Nihon Shokuhin Kako Co., Ltd.) to prepare a solution to be administered (0.08 mg/mL, as a solution to be administered for oral administration). To each BALB/c mouse (male, 7-week old, Charles River Laboratories Japan, Inc.), each compound was orally administered at a dose of 0.8 mg/kg. Blood was collected from the jugular vein or heart with time up to 24 hours after the administration. The obtained blood was centrifuged to collect blood plasma. The blood plasma was pretreated by methanol extraction method, and the concentration of the compound was analyzed by LC/MS/MS (ESI positive mode).

The obtained pharmacokinetic parameters were summarized in Table 6. As comparative control compounds, Comparative Compound 2 and Comparative Compound 5 were used.

TABLE 6

| Compound | $C_{max}$ (ng/mL) | $AUC_{0-\infty}$ (ng · hr/mL) |
|---|---|---|
| 46b | 561 | 588 |
| Comparative Compound 2 | 79.7 | 116 |
| Comparative Compound 5 | 11.4 | 59.8 |

In this table, $C_{max}$ represents a maximum plasma concentration; and $AUC_{0-\infty}$ represents an area under the curve of the plasma concentration of the compound from after the compound administration to infinite time.

As is apparent from the results in Table 6, Compound (I) exhibited a markedly higher $C_{max}$ and a markedly higher $AUC_{0-\infty}$ than these comparative control compounds, and exhibited an excellent in vivo pharmacokinetics when orally administered.

5) Evaluation of Metabolic Stability of Compound in Human CYP (Cytochrome P450)

Each test compound was mixed at a concentration of 2 µM with a phosphate buffer solution containing Human liver microsomes (Xenotech) in an amount of 0.5 mg/mL. Thereafter, NADPH was added thereto, and the obtained mixture was allowed to react at 37° C. for up to 30 minutes. The reaction was terminated by adding acetonitrile, and then the resultant was centrifuged for 10 minutes at 4° C. to collect a supernatant. The supernatant was pretreated by methanol extraction method, and the concentration of the compound was analyzed by LC/MS/MS (ESI positive mode). The compound remaining rate was calculated from the obtained concentration of the compound. The intrinsic clearances ($CL_{int}$) obtained from the changes of the compound remaining rates are shown in Table 7. As comparative control compounds, Comparative Compound 3 and Comparative Compound 4c were used (5 μM).

TABLE 7

| Compound | $CL_{int}$ (mL/min/mg) |
| --- | --- |
| 46b | 0.094 |
| Comparative Compound 3 | 0.450 |
| Comparative Compound 4c | 0.321 |

As is apparent from the results in Table 7, Compound (I) had a lower intrinsic clearance than the comparative control compounds, and therefore exhibited an excellent metabolic stability.

6) Evaluation of Ability to Induce Drug-induced Phospholipidosis by Compound

Whether an ability to induce phospholipidosis by Compound (I) was observed or not was studied. The evaluation of Compound 46b described in the Examples was carried out by a method partially modified from the method described in *Experimental and Toxicologic Pathology* (2007, Vol. 58, pp. 375-382).

Each test compound and HCS Lipid TOX Green Phospholipidosis Detection Regent (Invitrogen), which is a phospholipid staining solution, were mixed with HepG2 cells, which are a cell line derived from human hepatoma, and the cells were cultured in the presence of 5% $CO_2$ at 37° C. for 48 hours. The culture supernatant after the culturing was removed, and Hoechest 33258 (Invitrogen), which is a nucleic acid staining solution, was added, followed by allowing the resulting mixture to react in the dark at room temperature for 20 minutes. The resultant was washed with PBS solution. Then the fluorescence intensity was measured with a microplate analyzer (Fusion-α, Packard), and FLA (a relative value when taking amiodarone hydrochloride (10 μM) as 1, the amiodarone hydrochloride being a positive control substance) was calculated according to the following equations. The case where FLA was less than 1 was judged as negative, and the case where FLA was not less than 1 was judged as positive. Each test compound was dissolved in DMSO before use, and the resulting solution was added to the cells such that the final concentration of DMSO was 1%.

$FLR=(FLL-FLLB)/(FLH-FLHB)$ $FLA=(FLR/FLR(\text{amiodarone hydrochloride}))$

FLL: phospholipid fluorescence intensity
FLLB: blank value when measuring the phospholipid fluorescence
FLH: nucleic acid fluorescence intensity
FLHB: blank value when measuring the nucleic acid fluorescence As a result, Compound 46b described in the Examples had a FLA value of less than 1 even at a concentration up to 10 μM, and therefore this was judged as negative.

The evaluation of Comparative Compound 4c, which was a comparative control compound, was carried out by a method partially modified from the method described in *Cell Biology and Toxicology* (2003, Vol. 19, pp. 161-176).

Each test compound was mixed with U937 cells, which are a cell line derived from human monocytes, and the cells were cultured in the presence of 5% $CO_2$ at 37° C. for 48 hours. The cell suspension after the culturing was replaced with a PBS solution containing Nile red (Invitrogen) which is a phospholipid staining solution, and the resulting mixture was allowed to react in the dark at room temperature for 10 minutes. After centrifugal washing with PBS solution, the fluorescence intensity was measured with a flow cytometer (Becton Dickinson) (Excitation Wavelength: 488 nm, Detection Region: 515-545 nm). As a negative control substance, valproic acid (300 μM) was used. The case where the fluorescence intensity was significantly increased compared to valproic acid was judged as positive, and the case where the fluorescence intensity was not significantly increased compared to valproic acid was judged as negative. Each test compound was dissolved in DMSO before use, and the resulting solution was added to the cells such that the final concentration of DMSO was 1%.

As a result, Comparative Compound 4c showed a significantly increased fluorescence intensity (Dunnett's test (Significance Level: less than 5%)) at a concentration of 20 μM, and therefore this was judged as positive.

From these results, it was proved that the comparative control compound had an ability to induce phospholipidosis and that Compound (I) did not have an ability to induce phospholipidosis.

7) Evaluation of Hepatotoxicity of Compound in Mouse

Compound (I) was suspended in 0.5% methylcellulose (Wako Pure Chemical Industries, Ltd.) to prepare a 50 mg/mL solution to be administered. To each ICR mouse (male, 7-week old, Charles River Laboratories Japan, Inc.), each compound was orally administered at a dose of 500 mg/kg. On the day after the administration, blood was collected from the posterior vena cava, and the obtained blood was centrifuged to collect blood plasma. AST (aspartate aminotransferase) value, which is a marker of hepatic disorders in blood plasma, was measured with a biochemistry automatic analyzer (Hitachi 7070, Hitachi, Ltd.). Comparative Compound 4 was suspended in 0.5% sodium carboxymethylcellulose (Wako Pure Chemical Industries, Ltd.) before use.

As a result, the AST value of the solvent-administered group was 34 to 40 U/L; the AST value of Compound 46b described in the Examples was 47 U/L and there was almost no change compared to that of the solvent-administered group; and the AST value of Comparative Compound 4 was 145 U/L and a statistically significantly increase was observed.

As is apparent from the results, Compound (I) had a markedly lower hepatotoxicity than the comparative control compound.

8) Evaluation of Compound in Allergic Dermatitis Models

The action of Compound (I) on skin swelling response in mouse allergic dermatitis models was studied. As the allergic dermatitis models, models partially modified from a type I allergic dermatitis model and a type IV allergic dermatitis model described in documents (*Inflamm. Res.*, 1998, Vol. 47, pp. 506-511 and *Int. Arch. Allergy. Appl. Immunol.*, 1990, Vol. 92, pp. 356-360) were used.

(1) Action on Skin Swelling Response in Type I Allergic Dermatitis Model

To each BALB/c mouse (female, 7-week old, Charles River Laboratories Japan, Inc.), mouse IgE anti-DNP antibody (0.05 mg/body, SEIKAGAKU CORPORATION) was intravenously administered to passively sensitize the mouse. Twenty four hours after the sensitization, 20 μL of 0.38%

DNFB (SIGMA) dissolved in acetone:olive oil (4:1) was applied to the auricle of the mouse to induce inflammation. From after the induction to 24 hours, the thickness of the auricle was measured with time using a Digimatic Indicator (Mitutoyo). Each test compound was dissolved in ethanol, and 20 μL of 0.5 w/v % solution was applied to the auricle at 1 hour before the induction.

The swelling ratio of the auricle was calculated according to the following equation. In addition, for each of the auricular swelling ratios between 0 and 4 hours after the induction and the auricular swelling ratios between 5 and 10 hours after the induction, AUC (which is an area under the curve when taking the time after the induction along the abscissa and taking the auricular swelling ratio along the ordinate, %·hr) was calculated. The AUC between 0 and 4 hours after the induction was considered as an immediate response, and the AUC between 5 and 10 hours after the induction was considered as a late response.

Auricular Swelling Ratio(%)=$(A-B)/B \times 100$

A: Thickness of the auricle after the induction
B: Thickness of the auricle before the induction As a result, both Compounds 46b and 50b described in the Examples suppressed both of immediate and late auricula swellings (the suppression ratios of Compounds 46b and 50b on immediate response were 94.4% and 33.4%, respectively; and the suppression ratios on late response were 93.1% and 50.2%, respectively).

(2) Action on Skin Swelling Response in Type IV Allergic Dermatitis Model

To the back of each BALB/c mouse (female, 7-week old, Charles River Laboratories Japan, Inc.), 25 μL of 0.5% DNFB solution dissolved in acetone:olive oil (4:1) was applied. On the next day, the same operations were repeated to actively sensitize the mouse. Four days after the sensitization, 20 μL of 0.2% DNFB solution dissolved in acetone:olive oil (4:1) was applied to the auricle of the sensitized mouse to induce inflammation. Twenty four hours after the induction, the thickness of the auricle was measured using a Digimatic Indicator (Mitutoyo). Each test compound was dissolved in ethanol and 20 μL of 0.5 w/v % solution was applied to the auricle at 1 hour before the induction; or each test compound was suspended in 0.5% methylcellulose (Wako Pure Chemical Industries, Ltd.) and the resulting solution was orally administered at 30 mg/kg at 1 hour before the induction. The swelling ratio of the auricle was calculated according to the following equation:

Auricular Swelling Ratio(%)=$(A-B)/B \times 100$

A: Thickness of the auricle after the induction
B: Thickness of the auricle before the induction.

As a result, both Compounds 46b and 50b described in the Examples suppressed the auricular swelling in both administration routes of oral administration and auricular application (the suppression ratios of Compounds 46b and 50b in oral administration were 37.7% and 54.4%, respectively; and the suppression ratios in auricular application were 49.2% and 48.0%, respectively).

As is apparent from the results, Compound (I) exhibited an excellent therapeutic effect on allergic dermatitis by orally administering or applying.

9) Evaluation of Compound in Inflammatory Bowel Disease Models

The action of Compound (I) on colonic disorders in inflammatory bowel disease models was studied. As the inflammatory bowel disease models, models partially modified from a TNBS-induced colitis model and a DSS-induced chronic colitis model described in documents (*Gastroenterology*, 1989, Vol. 96, pp. 29-36 and *Am. J. Physiol. Gastrointest. Liver Physiol.*, 2004, Vol. 287, pp. G115-124) were used.

(1) Action on Colonic Disorders in TNBS-induced Colitis Model

To each Slc:Wistar rat (male, 12-week old, Japan SLC, Inc.), TNBS (Wako Pure Chemical Industries, Ltd.) dissolved in ethanol was rectally administered under anesthesia, and the TNBS solution was held in the rectum for 1 hour to produce the colitis model. These rats had been fasted from 2 days before the TNBS administration to the day of the TNBS administration. Five days after the TNBS administration, the colon was isolated from the each rat, and the macroscopic damage score (which is a total of adhesion score, diarrhea score and ulcer score) was recorded as an index of damage in the colon. The macroscopic damage score was calculated based on the scores of Dubigeon et al. (*Eur. J. Pharmacol.*, 2001, Vol. 431, pp. 103-110) and the scores of Venkova et al. (*J. Pharmacol. Exp. Ther.*, 2004, Vol. 308, pp. 206-213).

Each of Compounds 46b and 50b described in the Examples was suspended in 0.5 w/v % methylcellulose (Wako Pure Chemical Industries, Ltd.), and the obtained solution was orally administered at 3 mg/kg once on the day of the TNBS administration and at 3 mg/kg twice a day for 4 days from the next day of the TNBS administration. The administration of these compounds on the day of the TNBS administration was carried out 30 minutes to 1 hour before the TNBS administration.

As a result, while the macroscopic damage score of the solvent-administered group was 6.0±0.9, the macroscopic damage score of Compound 46b described in the Examples was 3.3±0.7 and was statistically significantly decreased compared to the solvent-administered group (Wilcoxon test (Significance Level: less than 5%)).

In another experiment, while the macroscopic damage score of the solvent-administered group was 6.9±1.1, the macroscopic damage score of Compound 50b described in the Examples was a low value of 5.2±1.1.

(2) Action on Colonic Disorders in DSS-induced Chronic Colitis Model

To each BALB/cCrSlc mouse (female, 9-week old, Japan SLC, Inc.), DSS (Molecular Weight: 36-50 kDa; MP Biomedicals) dissolved in sterile ultrapure water was administered via free drinking for 5 days from the day of the start of the administration via drinking water (this day was considered as Day 0 after the start of the administration via drinking water), and then switched to administration of sterile ultrapure water via free drinking for 5 days. This cycle was repeated again, and DSS was further administered via free drinking for another 7 days to produce the colitis model. As an index of colitis symptoms, stool consistency scores were used. The stool consistency scores were based on the following criteria: normal stool was defined as score 0; loose stool was defined as score 2; and diarrhea was defined as score 4. On Day 27 after the start of the administration via drinking water, the onset of colitis was confirmed by the stool consistency score, and thereafter the DSS administration was switched to administration of sterile ultrapure water via free drinking The stool consistency scores were recorded every day for 5 days between Day 28 and Day 32 after the start of the administration via drinking water, and the total of the stool consistency scores for the 5 days was defined as a "stool consistency score (total)." Each test compound was suspended in 0.5 w/v % methylcellulose (Wako Pure Chemical Industries, Ltd.), and the obtained solution was orally administered at 10 mg/kg once on Day 27 after the start of the administration via drinking water and at 10 mg/kg twice a day between Day 28 and Day 31 after the start of the administration via drinking water.

As a result, while the stool consistency score (total) of the solvent-administered group was 9.5±0.8, the stool consistency scores (total) of Compounds 46b and 50b described in the Examples were each 5.7±0.8 and 6.5±0.6, and were both statistically significantly decreased compared to the solvent-administered group (Wilcoxon test (Significance Level: less than 1%)).

As is apparent from these results, Compound (I) exhibited an excellent therapeutic effect on inflammatory bowel disease by orally administering.

10) Evaluation of Compound in Pain Models

The action of Compound (I) on hyperalgesia in pain models was studied. As the pain models, models partially modified from an inflammatory pain model (a carrageenin paw edema pain model) and neuropathic pain models (Bennett model and Chung model) described in documents (*Anesth. Analg.*, 2009, Vol. 108, pp. 1680-1687; *Pain*, 1988, Vol. 33, pp. 87-107; and *Pain*, 1992, Vol. 50, pp. 355-363) were used.

(1) Action on Hyperalgesia in Inflammatory Pain Model (Carrageenin Paw Edema Pain Model)

To the footpad of the left hind limb of each Crl:CD (SD) rat (male, 6-week old, Charles River Laboratories Japan, Inc.), an 1 w/v % suspension of carrageenin (Zushi Kagaku Laboratory, Inc.) in physiological saline was subcutaneously administered at 0.1 mL/body to produce the carrageenin paw edema pain model. Ninety minutes after the administration of the 1 w/v % suspension of carrageenin in physiological saline, the pain threshold (mmHg) of the footpad of the left hind limb was measured using Analgesy Meter (TK-201, Unicom) wherein the stimulating pressure was set so as to rise from 0 mmHg to 100 mmHg for 10 seconds. Each test compound was suspended in 0.5 w/v % methylcellulose (Wako Pure Chemical Industries, Ltd.), and the obtained solution was orally administered 30 minutes before the administration of the 1 w/v % suspension of carrageenin in physiological saline. Compound 46b described in the Examples was administered at a dose of 100 mg/kg; Comparative Compound 4 was administered as a comparative control compound at a dose of 100 mg/kg; and diclofenac sodium (Sigma-Aldrich), which is a nonsteroidal anti-inflammatory agent, was administered as a comparative control agent at a dose of 3 mg/kg.

The results are shown in FIG. 1. The symbols "*", "#" and "†" in the figure indicate statistical significance based on the comparison with the solvent-administered group (Student's t-test) (***: P<0.001, significant difference between the solvent-administered group and Compound 46b-administered group; #: P<0.05, significant difference between the solvent-administered group and Comparative Compound 4-administered group; and, ††: P<0.01, significant difference between the solvent-administered group and diclofenac sodium-administered group).

As shown in FIG. 1, the pain threshold (mmHg) of Compound 46b-administered group was significantly elevated compared to the pain threshold (mmHg) of the solvent-administered group (Student's t-test (Significance Level: less than 0.1%)). In addition, the pain threshold (mmHg) of Compound 46b-administered group was higher than the pain thresholds (mmHg) of Comparative Compound 4-administered group and diclofenac sodium-administered group.

As is apparent from the results, Compound (I) exhibited an excellent therapeutic effect on inflammatory pain compared to the comparative control compound and the comparative control agent by orally administering.

(2) Action on Hyperalgesia in Neuropathic Pain Models (Bennett Model and Chung Model)

The Bennett model was produced by lightly ligating the sciatic nerve in the left thigh of each Crl:CD (SD) rat (male, 6-week old, Charles River Laboratories Japan, Inc.) at 4 points with chromic catgut (4-0). Fourteen days after the Bennett model was produced, each test compound was orally administered, and plantar test was performed 90 minutes after the administration. The plantar test was carried out by measuring the pain threshold (sec) of the left footpad (model foot) using a plantar thermal stimulation device (Plantar test 7370, Ugo Basile) wherein the thermal stimulus intensity was set to 60. Each test compound was suspended in 0.5 w/v % methylcellulose (Wako Pure Chemical Industries, Ltd.) and the obtained solution was orally administered. Compound 46b described in the Examples was administered at a dose of 100 mg/kg, and gabapentin (Toronto Research Chemicals), which is an anticonvulsant, was administered as a comparative control agent at a dose of 100 mg/kg.

The Chung model was produced by completely ligating the L5 and L6 spinal nerves of each Crl:CD (SD) rat (male, 6-week old, Charles River Laboratories Japan, Inc.) with a silk suture (5-0). Seven days after the Chung model was produced, each test compound was orally administered, and von Frey test was performed 90 minutes after the administration. In addition, fifteen days after the Chung model was produced, each test compound was orally administered, and plantar test was performed 90 minutes after the administration. The von Frey test was carried out by measuring the pain threshold (g) of the left footpad (model foot) using Dynamic Plantar Aesthesiometer (37400, Ugo Basile) wherein the maximum pressure was set to 30.0 g and the time required to reach the maximum pressure was set to 40 seconds. The plantar test was carried out by the method described above. Each test compound was suspended in 0.5 w/v % methylcellulose (Wako Pure Chemical Industries, Ltd.), and the obtained solution was orally administered. Compound 46b described in the Examples was administered at a dose of 100 mg/kg, and gabapentin (Toronto Research Chemicals), which is an anticonvulsant, was administered as a comparative control agent at a dose of 100 mg/kg.

Figure 2:
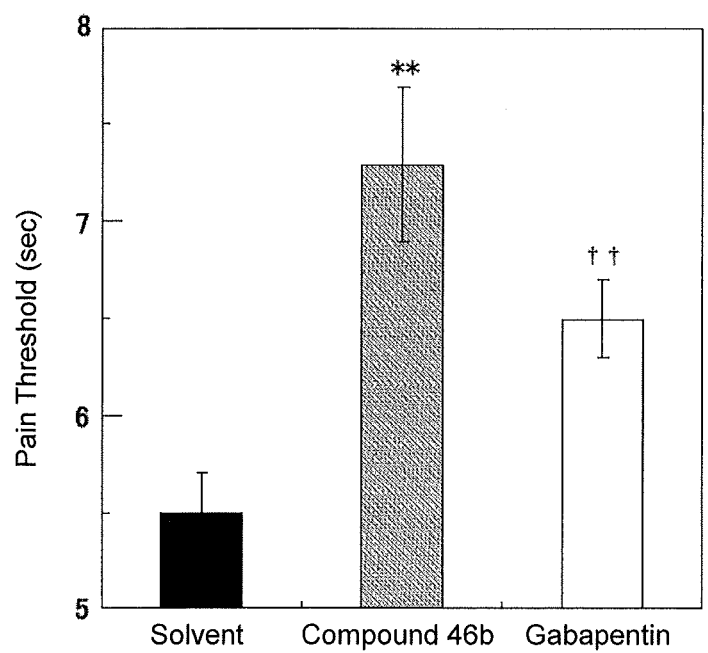
FIG. 2 is a diagram showing the effect of Compound 46b on hyperalgesia in a neuropathic pain model (Bennett model).

The results of the plantar test in the Bennett model are shown in FIG. 2. The symbols "*" and "†" in the figure indicate statistical significance based on the comparison with the solvent-administered group (Student's t-test) (**: P<0.01, significant difference between the solvent-administered group and Compound 46b-administered group; and, ††: P<0.01, significant difference between the solvent-administered group and gabapentin-administered group).

As shown in FIG. 2, the pain threshold (sec) of Compound 46b-administered group was significantly elevated compared to the pain threshold (sec) of the solvent-administered group (Student's t-test (Significance Level: less than 1%)). In addition, the pain threshold (sec) of Compound 46b-administered group was higher than the pain threshold (sec) of gabapentin-administered group.

As a result of the von Frey test in the Chung model, while the pain threshold of the solvent-administered group was 5.8±0.1 g, the pain threshold in case of Compound 46b described in the Examples was 7.0±0.3 g, and was statistically significantly elevated compared to the solvent-administered group (Student's t-test (Significance Level: less than 1%)).

Figure 3:
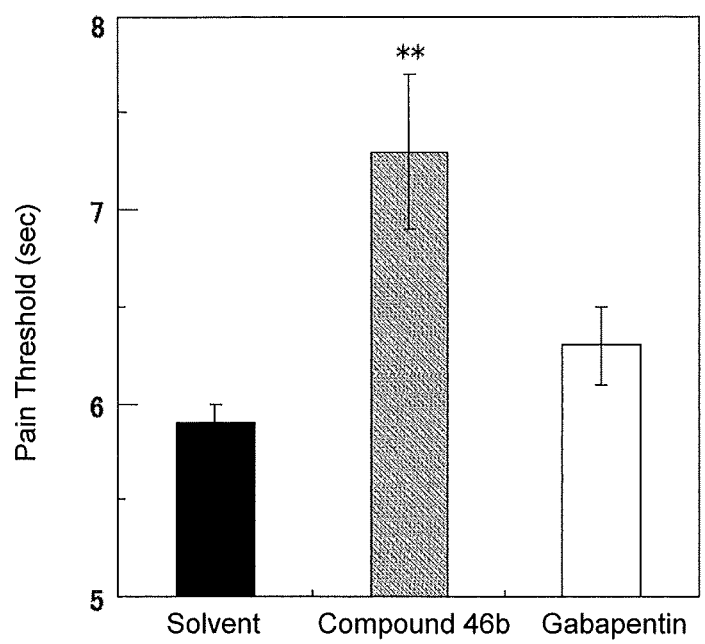
FIG. 3 is a diagram showing the effect of Compound 46b on hyperalgesia in a neuropathic pain model (Chung model).

The results of the plantar test in the Chung model are shown in FIG. 3. The symbols "*" in the figure indicate statistical significance based on the comparison with the solvent-administered group (Student's t-test) (**: P<0.01, significant difference between the solvent-administered group and Compound 46b-administered group).

As shown in FIG. 3, the pain threshold (sec) of Compound 46b-administered group was significantly elevated compared to the pain threshold (sec) of the solvent-administered group (Student's t-test (Significance Level: less than 1%)). In addition, the pain threshold (sec) of Compound 46b-administered group was higher than the pain threshold (sec) of gabapentin-administered group.

As is apparent from these results, Compound (I) exhibited an excellent therapeutic effect on neuropathic pain compared to the comparative control agent by orally administering.

INDUSTRIAL APPLICABILITY

A novel 2,3-dihydro-1H-indene-2-yl urea derivative and a pharmaceutically acceptable salt thereof, can be used as pharmaceuticals comprising them as an effective ingredient.

The invention claimed is:
1. A 2,3-dihydro-1H-indene-2-yl urea compound represented by Formula (Ia) or a pharmaceutically acceptable salt thereof:

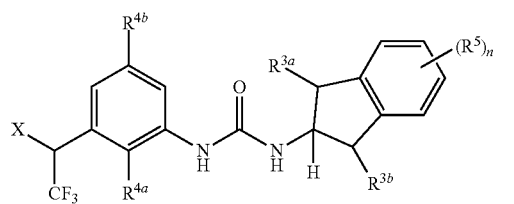

(Ia)

wherein, n represents an integer of 0 to 4; $R^{3a}$ represents $R^6O$— or $(R^6)_2N$—; $R^{3b}$ represents hydrogen, $R^6O$— or $(R^6)_2N$—; $R^{4a}$ represents alkyl of 1 to 6 carbon atoms (which may be substituted with 1 or more halogen, $R^6O$— and/or $(R^6)_2N$—), $R^6O$—, $(R^6)_2N$— or halogen; $R^{4b}$ represents alkyl of 1 to 6 carbon atoms (which may be substituted with 1 or more halogen, $R^6O$— and/or $(R^6)_2N$—), cycloalkyl of 3 to 8 carbon atoms (which may be substituted with 1 to 3 $R^6$ that are each independent; wherein 1 to 3 methylenes constituting a ring may be substituted with each independently —O—, —S—, —C(O)— or —N($R^6$)—; and wherein a carbon atom directly bound to a benzene ring may be substituted with a nitrogen atom), $R^6O$—, $(R^6)_2N$— or halogen; $R^5$ each independently represents alkyl of 1 to 6 carbon atoms (which may be substituted with 1 or more halogen, $R^6O$— and/or $(R^6)_2N$—), cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom), $R^6O$—, $(R^6)_2N$—, $R^6C(O)NH$—, $R^6S(O)_2NH$—, $R^6C(O)$—, $R^6OC(O)$—, $(R^6)_2NC(O)$—, cyano or halogen; $R^6$ each independently represents hydrogen or alkyl of 1 to 6 carbon atoms (which may be substituted with 1 or more halogen); and X represents $R^6O$— or $(R^6)_2N$—.

2. The 2,3-dihydro-1H-indene-2-yl urea compound or the pharmaceutically acceptable salt thereof according to claim 1, wherein
$R^{3b}$ is hydrogen;
$R^{3a}$ and $R^{4a}$ are $R^6O$—;
$R^{4b}$ is alkyl of 3 to 6 carbon atoms, cycloalkyl of 3 to 8 carbon atoms (which may be substituted with 1 to 3 $R^6$ that are each independent; wherein 1 to 3 methylenes constituting a ring may be each independently substituted with —O—, —S—, —C(O)— or —N($R^6$)—; and wherein a carbon atom directly bound to a benzene ring may be substituted with a nitrogen atom) or halogen; and
$R^5$ is each independently $R^6O$— or halogen.

3. The 2,3-dihydro-1H-indene-2-yl urea compound or the pharmaceutically acceptable salt thereof according to claim 1, wherein
$R^{3a}$ is hydroxy;
$R^{4a}$ is methoxy or ethoxy;
$R^{4b}$ is 2-propyl, 2-butyl, 2-methyl-2-propyl, 2-methyl-2-butyl, pyrrolidinyl, piperidinyl, azepanyl, morpholinyl or bromo;
$R^5$ is hydroxy, methoxy, ethoxy, fluoro, chloro or bromo; and
X is hydroxy, amino, methylamino or dimethylamino.

4. The 2,3-dihydro-1H-indene-2-yl urea compound or the pharmaceutically acceptable salt thereof according to claim 1, wherein
$R^{4a}$ is methoxy;
$R^{4b}$ is 2-methyl-2-propyl; and
X is hydroxy.

5. A pharmaceutical comprising the 2,3-dihydro-1H-indene-2-yl urea compound or the pharmaceutically acceptable salt thereof according to claim 1 as an effective ingredient.

6. A therapeutic agent for allergic dermatitis comprising the 2,3-dihydro-1H-indene-2-yl urea compound or the pharmaceutically acceptable salt thereof according to claim 1 as an effective ingredient.

7. A therapeutic agent for inflammatory bowel disease comprising the 2,3-dihydro-1H-indene-2-yl urea compound or the pharmaceutically acceptable salt thereof according to claim 1 as an effective ingredient.

8. A therapeutic agent for pain comprising the 2,3-dihydro-1H-indene-2-yl urea compound or the pharmaceutically acceptable salt thereof according to claim 1 as an effective ingredient.

9. The 2,3-dihydro-1H-indene-2-yl urea compound or the pharmaceutically acceptable salt thereof according to claim 2, wherein
$R^{3a}$ is hydroxy;
$R^{4a}$ is methoxy or ethoxy;
$R^{4b}$ is 2-propyl, 2-butyl, 2-methyl-2-propyl, 2-methyl-2-butyl, pyrrolidinyl, piperidinyl, azepanyl, morpholinyl or bromo;
$R^5$ is hydroxy, methoxy, ethoxy, fluoro, chloro or bromo; and
X is hydroxy, amino, methylamino or dimethylamino.

10. The 2,3-dihydro-1H-indene-2-yl urea compound or the pharmaceutically acceptable salt thereof according to claim 2, wherein
$R^{4a}$ is methoxy;
$R^{4b}$ is 2-methyl-2-propyl; and
X is hydroxy.

11. The 2,3-dihydro-1H-indene-2-yl urea compound or the pharmaceutically acceptable salt thereof according to claim 3, wherein
$R^{4a}$ is methoxy;
$R^{4b}$ is 2-methyl-2-propyl; and
X is hydroxy.

12. A pharmaceutical comprising the 2,3-dihydro-1H-indene-2-yl urea compound or the pharmaceutically acceptable salt thereof according to claim 2 as an effective ingredient.

13. A pharmaceutical comprising the 2,3-dihydro-1H-indene-2-yl urea compound or the pharmaceutically acceptable salt thereof according to claim 3 as an effective ingredient.

14. A pharmaceutical comprising the 2,3-dihydro-1H-indene-2-yl urea compound or the pharmaceutically acceptable salt thereof according to claim 4 as an effective ingredient.

15. A therapeutic agent for allergic dermatitis comprising the 2,3-dihydro-1H-indene-2-yl urea compound or the pharmaceutically acceptable salt thereof according to claim 2 as an effective ingredient.

16. A therapeutic agent for allergic dermatitis comprising the 2,3-dihydro-1H-indene-2-yl urea compound or the pharmaceutically acceptable salt thereof according to claim 3 as an effective ingredient.

17. A therapeutic agent for allergic dermatitis comprising the 2,3-dihydro-1H-indene-2-yl urea compound or the pharmaceutically acceptable salt thereof according to claim 4 as an effective ingredient.

18. A therapeutic agent for allergic dermatitis comprising the 2,3-dihydro-1H-indene-2-yl urea compound or the pharmaceutically acceptable salt thereof as an effective ingredient.

19. A method for therapy of allergic dermatitis comprising administering an effective amount of said, 2, 3-dihydro-1H-inden-2-yl urea compound or the pharmaceutically acceptable salt thereof according to claim 1.

20. A method for therapy of Crohn's disease or ulcerative colitis comprising administering an effective amount of said 2, 3-dihydro-1H-inden-2-yl urea compound or the pharmaceutically acceptable salt thereof according to claim 1.

21. A method for therapy of inflammatory pain or neuropathic pain comprising administering an effective amount of said 2, 3-dihydro-1H-inden-2-yl urea compound or the pharmaceutically acceptable salt thereof according to claim 1.

* * * * *